(12) United States Patent
Racenet et al.

(10) Patent No.: US 8,424,739 B2
(45) Date of Patent: Apr. 23, 2013

(54) SURGICAL STAPLING DEVICE WITH INDEPENDENT TIP ROTATION

(75) Inventors: David C. Racenet, Litchfield, CT (US); Ralph Stearns, Bozrah, CT (US); Philip Roy, Hamden, CT (US); John W. Beardsley, Hamden, CT (US); Lee Ann Olson, Wallingford, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 13/233,299

(22) Filed: Sep. 15, 2011

(65) Prior Publication Data

US 2012/0000962 A1    Jan. 5, 2012

Related U.S. Application Data

(63) Continuation of application No. 10/968,525, filed on Oct. 18, 2004.

(60) Provisional application No. 60/512,481, filed on Oct. 17, 2003.

(51) Int. Cl.
    *A61B 17/06813*    (2006.01)
(52) U.S. Cl.
    USPC .................. 227/177.1; 227/19; 227/176.1
(58) Field of Classification Search ........... 227/19, 227/175.1, 176.1, 177.1, 178.1; 606/219
    See application file for complete search history.

(56) References Cited

U.S. PATENT DOCUMENTS

| | | |
|---|---|---|
| 3,079,606 A | 3/1963 | Bobrov et al. |
| 3,490,675 A | 1/1970 | Green et al. |
| 4,429,695 A | 2/1984 | Green |
| 4,505,414 A | 3/1985 | Filipi |
| 4,580,712 A | 4/1986 | Green |
| 4,589,413 A | 5/1986 | Malyshev et al. |
| 4,602,634 A | 7/1986 | Barkley |
| 4,608,981 A | 9/1986 | Rothfuss et al. |
| 4,610,383 A | 9/1986 | Rothfuss et al. |
| 4,633,861 A | 1/1987 | Chow et al. |
| 4,633,874 A | 1/1987 | Chow et al. |
| 4,671,445 A | 6/1987 | Barker et al. |
| 4,703,887 A | 11/1987 | Clanton et al. |

(Continued)

FOREIGN PATENT DOCUMENTS

| | | |
|---|---|---|
| DE | 2744824 | 4/1978 |
| DE | 2903159 | 1/1980 |

(Continued)

OTHER PUBLICATIONS

European Search Report for EP 04795759.2-2310 date of completion is Apr. 8, 2010 (3 pages).

(Continued)

*Primary Examiner* — M. Alexandra Elve
*Assistant Examiner* — Nathaniel Chukwurah

(57) ABSTRACT

A surgical stapling device is disclosed which includes a handle assembly, an endoscopic body portion and a tool assembly. The tool assembly is rotatably and pivotally supported on a distal end of the endoscopic body portion. A tool assembly rotation mechanism is provided which includes a rotation knob, a substantially rigid tube and a flexible member interconnecting the rigid tube to the tool assembly. The substantially rigid tube translates rotation of the rotation knob to rotation of the flexible member and provides a channel for passage of other components of the surgical stapling device.

19 Claims, 40 Drawing Sheets

U.S. PATENT DOCUMENTS

| | | |
|---|---|---|
| 4,728,020 A | 3/1988 | Green et al. |
| 4,784,137 A | 11/1988 | Kulik et al. |
| 4,863,088 A | 9/1989 | Redmond et al. |
| 4,892,244 A | 1/1990 | Fox et al. |
| 4,991,764 A | 2/1991 | Mericle |
| 5,040,715 A | 8/1991 | Green et al. |
| 5,065,929 A | 11/1991 | Schulze et al. |
| 5,074,454 A | 12/1991 | Peters |
| 5,083,695 A | 1/1992 | Foslien et al. |
| 5,111,987 A | 5/1992 | Moeinzadeh et al. |
| 5,129,570 A | 7/1992 | Schulze et al. |
| 5,141,144 A | 8/1992 | Foslien et al. |
| 5,170,925 A | 12/1992 | Madden et al. |
| RE34,519 E | 1/1994 | Fox et al. |
| 5,307,976 A | 5/1994 | Olson et al. |
| 5,312,023 A | 5/1994 | Green et al. |
| 5,318,221 A | 6/1994 | Green et al. |
| 5,326,013 A | 7/1994 | Green et al. |
| 5,330,502 A | 7/1994 | Hassler et al. |
| 5,332,142 A | 7/1994 | Robinson et al. |
| 5,364,002 A | 11/1994 | Green et al. |
| 5,364,003 A | 11/1994 | Williamson, IV |
| 5,376,095 A | 12/1994 | Ortiz |
| 5,381,943 A | 1/1995 | Allen et al. |
| 5,383,880 A | 1/1995 | Hooven |
| 5,395,033 A | 3/1995 | Byrne et al. |
| 5,395,034 A | 3/1995 | Allen et al. |
| 5,397,046 A | 3/1995 | Savage et al. |
| 5,397,324 A | 3/1995 | Carroll et al. |
| 5,407,293 A | 4/1995 | Crainich |
| 5,415,334 A | 5/1995 | Williamson, IV et al. |
| 5,415,335 A | 5/1995 | Knodell, Jr. |
| 5,417,361 A | 5/1995 | Williamson, IV |
| 5,431,323 A | 7/1995 | Smith et al. |
| 5,433,721 A | 7/1995 | Hooven et al. |
| 5,447,265 A | 9/1995 | Vidal et al. |
| 5,452,837 A | 9/1995 | Williamson, IV et al. |
| 5,464,300 A | 11/1995 | Crainich |
| 5,465,895 A | 11/1995 | Knodel et al. |
| 5,467,911 A | 11/1995 | Tsuruta et al. |
| 5,470,007 A | 11/1995 | Plyley et al. |
| 5,470,010 A | 11/1995 | Rothfuss et al. |
| 5,474,566 A | 12/1995 | Alesi et al. |
| 5,478,003 A | 12/1995 | Green et al. |
| 5,484,451 A | 1/1996 | Akopov et al. |
| 5,485,947 A | 1/1996 | Olson et al. |
| 5,487,500 A | 1/1996 | Knodel et al. |
| 5,489,058 A | 2/1996 | Plyley et al. |
| 5,518,163 A | 5/1996 | Hooven |
| 5,518,164 A | 5/1996 | Hooven |
| 5,529,235 A | 6/1996 | Boiarski et al. |
| 5,531,744 A | 7/1996 | Nardella et al. |
| 5,535,934 A | 7/1996 | Boiarski et al. |
| 5,535,937 A | 7/1996 | Boiarski et al. |
| 5,549,637 A | 8/1996 | Crainich |
| 5,551,622 A | 9/1996 | Yoon |
| 5,553,765 A | 9/1996 | Knodel et al. |
| 5,562,239 A | 10/1996 | Boiarski et al. |
| 5,562,241 A | 10/1996 | Knodel et al. |
| 5,562,682 A | 10/1996 | Oberlin et al. |
| 5,564,615 A | 10/1996 | Bishop et al. |
| 5,573,543 A | 11/1996 | Akopov et al. |
| 5,577,654 A | 11/1996 | Bishop |
| 5,586,711 A | 12/1996 | Plyley et al. |
| 5,588,580 A | 12/1996 | Paul et al. |
| 5,588,581 A | 12/1996 | Conlon et al. |
| 5,597,107 A | 1/1997 | Knodel et al. |
| 5,601,224 A | 2/1997 | Bishop et al. |
| 5,607,095 A | 3/1997 | Smith et al. |
| 5,624,452 A | 4/1997 | Yates |
| 5,626,587 A | 5/1997 | Bishop et al. |
| 5,628,446 A | 5/1997 | Geiste et al. |
| 5,630,539 A | 5/1997 | Plyley et al. |
| 5,630,540 A | 5/1997 | Blewett |
| 5,630,541 A | 5/1997 | Williamson et al. |
| 5,632,432 A | 5/1997 | Schulze et al. |
| 5,634,584 A | 6/1997 | Okorocha et al. |
| 5,636,780 A | 6/1997 | Green et al. |
| 5,645,209 A | 7/1997 | Green et al. |
| 5,647,526 A | 7/1997 | Green et al. |
| 5,651,491 A | 7/1997 | Heaton et al. |
| 5,653,374 A | 8/1997 | Young et al. |
| 5,653,721 A | 8/1997 | Knodel et al. |
| 5,655,698 A | 8/1997 | Yoon |
| 5,657,921 A | 8/1997 | Young et al. |
| 5,658,300 A | 8/1997 | Bito et al. |
| 5,662,258 A | 9/1997 | Knodel et al. |
| 5,662,259 A | 9/1997 | Yoon |
| 5,662,260 A | 9/1997 | Yoon |
| 5,662,662 A | 9/1997 | Bishop et al. |
| 5,662,666 A | 9/1997 | Onuki et al. |
| 5,667,517 A | 9/1997 | Hooven |
| 5,669,544 A | 9/1997 | Schulze et al. |
| 5,673,840 A | 10/1997 | Schulze et al. |
| 5,673,841 A | 10/1997 | Schulze et al. |
| 5,673,842 A | 10/1997 | Bittner et al. |
| 5,676,674 A | 10/1997 | Botanos et al. |
| 5,680,982 A | 10/1997 | Schulze et al. |
| 5,690,269 A | 11/1997 | Bolanos et al. |
| 5,692,668 A | 12/1997 | Schulze et al. |
| 5,697,542 A | 12/1997 | Knodel et al. |
| 5,704,534 A | 1/1998 | Huitema et al. |
| 5,709,334 A | 1/1998 | Sorrentino et al. |
| 5,711,472 A | 1/1998 | Bryan |
| 5,713,505 A | 2/1998 | Huitema |
| 5,716,366 A | 2/1998 | Yates |
| 5,728,110 A | 3/1998 | Vidal et al. |
| 5,735,848 A | 4/1998 | Yates et al. |
| 5,743,456 A | 4/1998 | Jones et al. |
| 5,749,893 A | 5/1998 | Vidal et al. |
| 5,752,644 A | 5/1998 | Bolanos et al. |
| 5,762,255 A | 6/1998 | Chrisman et al. |
| 5,762,256 A | 6/1998 | Mastri et al. |
| 5,769,303 A | 6/1998 | Knodel et al. |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A | 7/1998 | Koukline |
| 5,797,536 A | 8/1998 | Smith et al. |
| 5,797,537 A | 8/1998 | Oberlin et al. |
| 5,797,538 A * | 8/1998 | Heaton et al. .............. 227/176.1 |
| 5,810,811 A | 9/1998 | Yates et al. |
| 5,810,855 A | 9/1998 | Rayburn et al. |
| 5,816,471 A | 10/1998 | Plyley et al. |
| 5,817,109 A | 10/1998 | McGarry et al. |
| 5,820,009 A | 10/1998 | Melting et al. |
| 5,823,066 A | 10/1998 | Huitema et al. |
| 5,826,776 A | 10/1998 | Schulze et al. |
| 5,829,662 A | 11/1998 | Allen et al. |
| 5,833,695 A | 11/1998 | Yoon |
| 5,836,147 A | 11/1998 | Schnipke |
| 5,862,972 A | 1/1999 | Green et al. |
| 5,865,361 A | 2/1999 | Mitliman et al. |
| 5,871,135 A | 2/1999 | Williamson, IV et al. |
| 5,897,562 A | 4/1999 | Bolanos et al. |
| 5,901,895 A | 5/1999 | Heaton et al. |
| 5,911,353 A | 6/1999 | Bolanos et al. |
| 5,918,791 A | 7/1999 | Sorrentino et al. |
| 5,954,259 A | 9/1999 | Viola et al. |
| 6,004,335 A | 12/1999 | Vaitekunas et al. |
| 6,010,054 A | 1/2000 | Johnson et al. |
| 6,032,849 A | 3/2000 | Mastri et al. |
| 6,079,606 A | 6/2000 | Milliman et al. |
| 6,109,500 A | 8/2000 | Alli et al. |
| 6,197,017 B1 | 3/2001 | Brock et al. |
| 6,202,914 B1 | 3/2001 | Geiste et al. |
| 6,241,139 B1 | 6/2001 | Milliman et al. |
| 6,250,532 B1 | 6/2001 | Green et al. |
| 6,264,086 B1 | 7/2001 | McGuckin, Jr. |
| 6,264,087 B1 | 7/2001 | Whitman |
| 6,269,977 B1 | 8/2001 | Moore |
| 6,315,183 B1 | 11/2001 | Piraka |
| 6,315,184 B1 | 11/2001 | Whitman |
| 6,325,810 B1 | 12/2001 | Hamilton et al. |
| 6,330,965 B1 | 12/2001 | Milliman et al. |
| 6,439,446 B1 | 8/2002 | Perry et al. |

| | | |
|---|---|---|
| 6,443,973 B1 | 9/2002 | Whitman |
| 6,488,196 B1 | 12/2002 | Fenton, Jr. |
| 6,503,257 B2 | 1/2003 | Grant et al. |
| 6,505,768 B2 | 1/2003 | Whitman |
| 6,544,274 B2 | 4/2003 | Danitz et al. |
| 6,554,844 B2 | 4/2003 | Lee et al. |
| 6,565,554 B1 | 5/2003 | Niemeyer |
| 6,587,750 B2 | 7/2003 | Gerbi et al. |
| 6,592,597 B2 | 7/2003 | Grant et al. |
| 6,594,552 B1 | 7/2003 | Nowlin et al. |
| 6,602,252 B2 | 8/2003 | Mollenauer |
| 6,656,193 B2 | 12/2003 | Grant et al. |
| 6,698,643 B2 | 3/2004 | Whitman |
| 6,722,552 B2 | 4/2004 | Fenton, Jr. |

FOREIGN PATENT DOCUMENTS

| | | |
|---|---|---|
| DE | 3114135 | 10/1982 |
| DE | 4213426 | 10/1992 |
| DE | 4300307 | 7/1994 |
| EP | 0041022 | 12/1981 |
| EP | 0136950 | 4/1985 |
| EP | 0140552 | 5/1985 |
| EP | 0156774 | 10/1985 |
| EP | 0216532 | 4/1987 |
| EP | 0220029 | 4/1987 |
| EP | 0213817 | 11/1987 |
| EP | 0273468 | 7/1988 |
| EP | 0324166 | 7/1989 |
| EP | 0324635 | 7/1989 |
| EP | 0324637 | 7/1989 |
| EP | 0324638 | 7/1989 |
| EP | 0369324 | 5/1990 |
| EP | 0373762 | 6/1990 |
| EP | 0380025 | 8/1990 |
| EP | 0399701 | 11/1990 |
| EP | 0449394 | 10/1991 |
| EP | 0484677 | 5/1992 |
| EP | 0489436 | 6/1992 |
| EP | 0503662 | 9/1992 |
| EP | 0514139 | 11/1992 |
| EP | 0536903 | 4/1993 |
| EP | 0537572 | 4/1993 |
| EP | 0539762 | 5/1993 |
| EP | 0545029 | 6/1993 |
| EP | 0552050 | 7/1993 |
| EP | 0552423 | 7/1993 |
| EP | 0579038 | 1/1994 |
| EP | 0589306 | 3/1994 |
| EP | 0591946 | 4/1994 |
| EP | 0592243 | 4/1994 |
| EP | 0592244 | 4/1994 |
| EP | 0593920 | 4/1994 |
| EP | 0598202 | 5/1994 |
| EP | 0598579 | 5/1994 |
| EP | 0621006 | 10/1994 |
| EP | 0621009 | 10/1994 |
| EP | 0625335 | 11/1994 |
| EP | 0656188 | 6/1995 |
| EP | 0365153 | 8/1995 |
| EP | 0666057 | 8/1995 |
| EP | 0705570 | 4/1996 |
| EP | 0705571 | 4/1996 |
| FR | 2542188 | 9/1984 |
| FR | 2660851 | 10/1991 |
| FR | 2681775 | 10/1991 |
| GB | 1352554 | 4/1971 |
| GB | 1452185 | 10/1976 |
| GB | 1555455 | 11/1979 |
| GB | 2048685 | 12/1980 |
| GB | 2070499 | 9/1981 |
| GB | 2141066 | 12/1984 |
| GB | 2165559 | 4/1986 |
| RU | 728848 | 5/1977 |
| RU | 659146 | 4/1979 |
| RU | 980703 | 12/1982 |
| RU | 990220 | 1/1983 |
| WO | WO 83/02247 | 7/1983 |
| WO | WO 89/10094 | 11/1989 |
| WO | WO 92/10976 | 7/1992 |
| WO | WO 9308754 | 5/1993 |
| WO | WO 9314706 | 8/1993 |
| WO | WO 2004/032762 | 4/2004 |

OTHER PUBLICATIONS

European Search Report for EP 10007905.2 dated Sep. 30, 2010.
European Search Report for EP 10007933.4 dated Sep. 30, 2010.

* cited by examiner

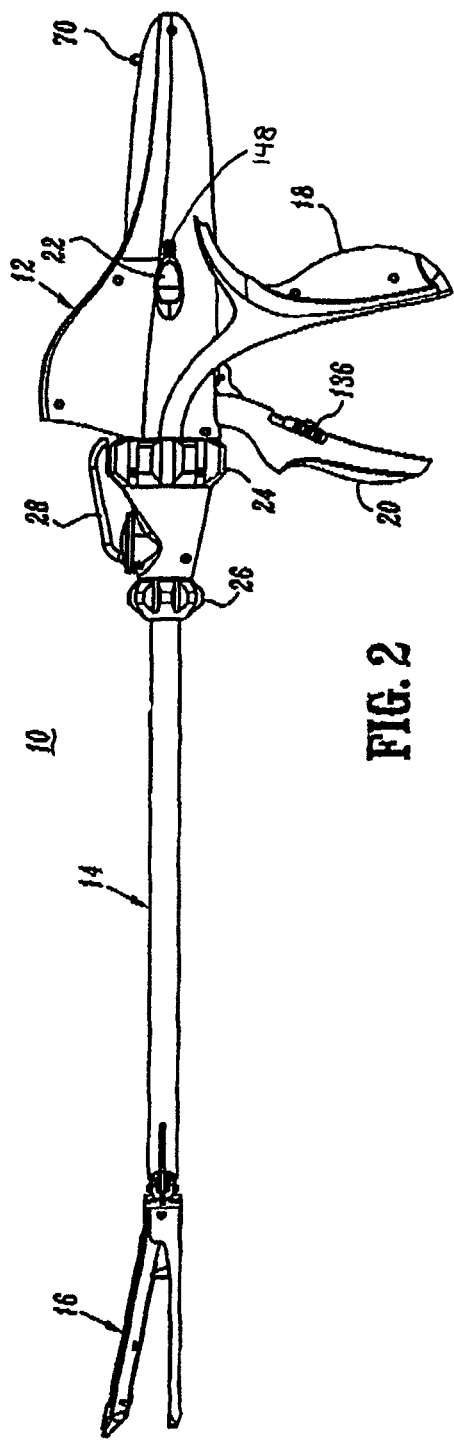
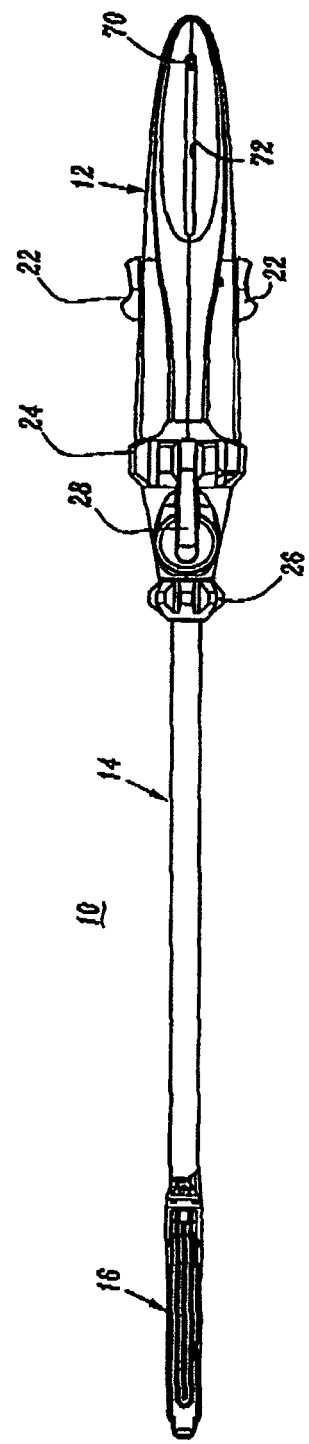

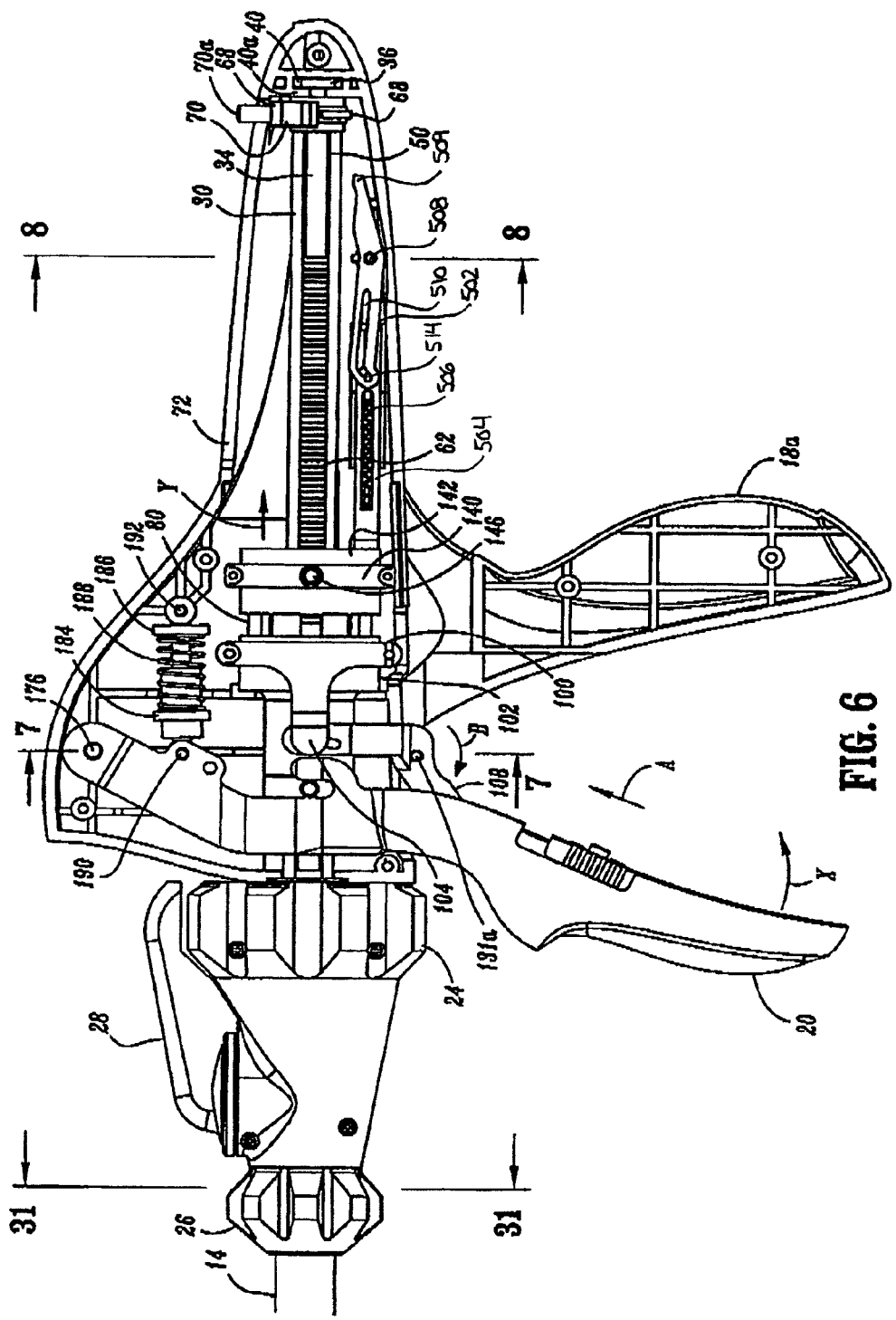

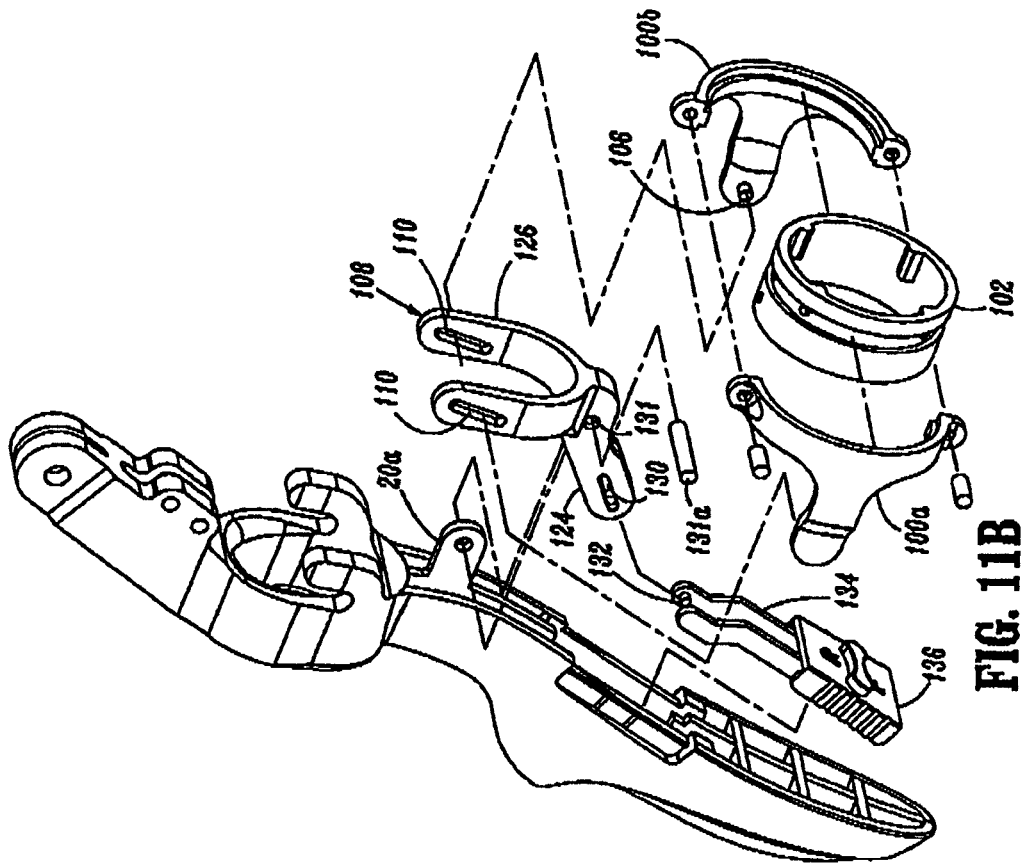
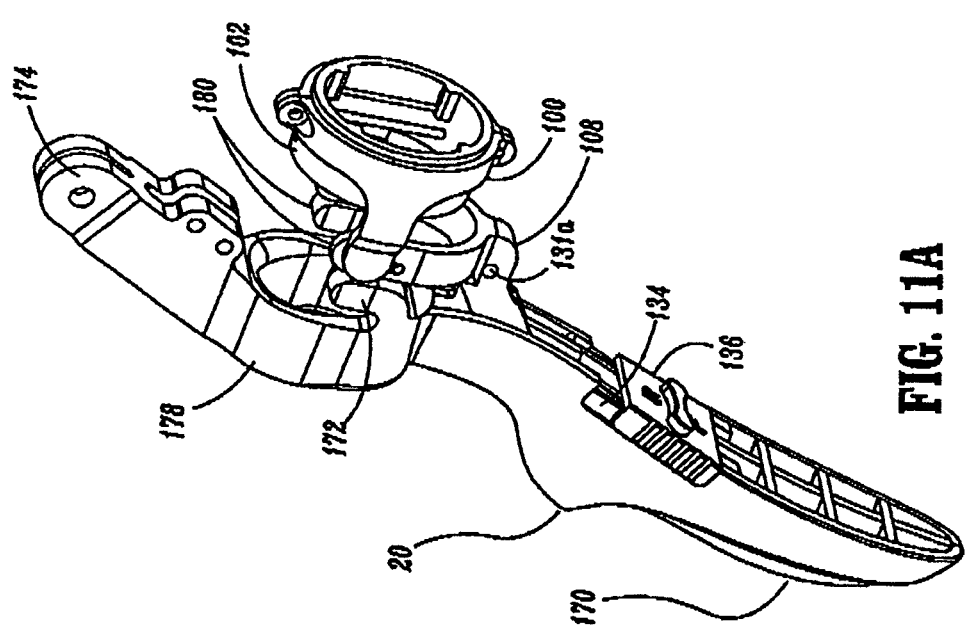
FIG. 11B
FIG. 11A

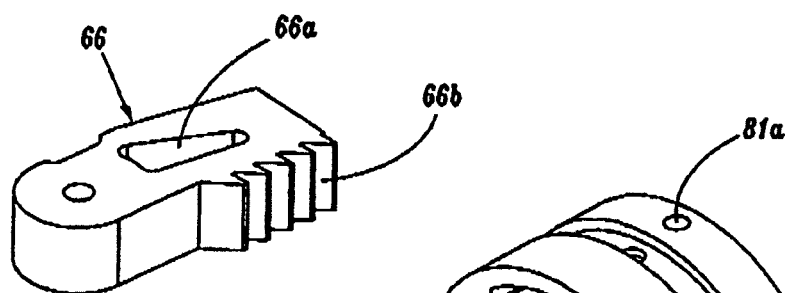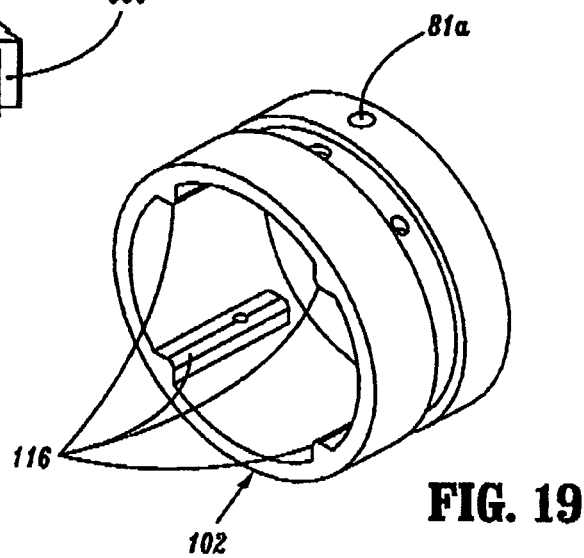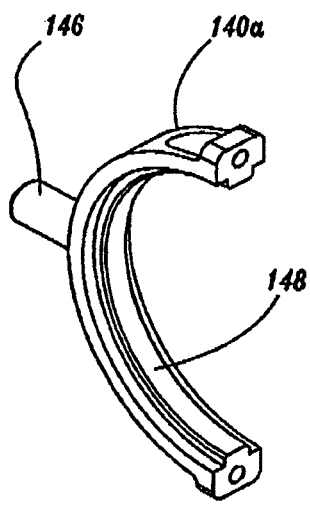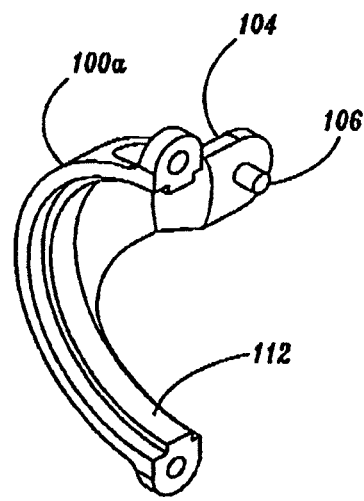
FIG. 18
FIG. 19
FIG. 20
FIG. 21

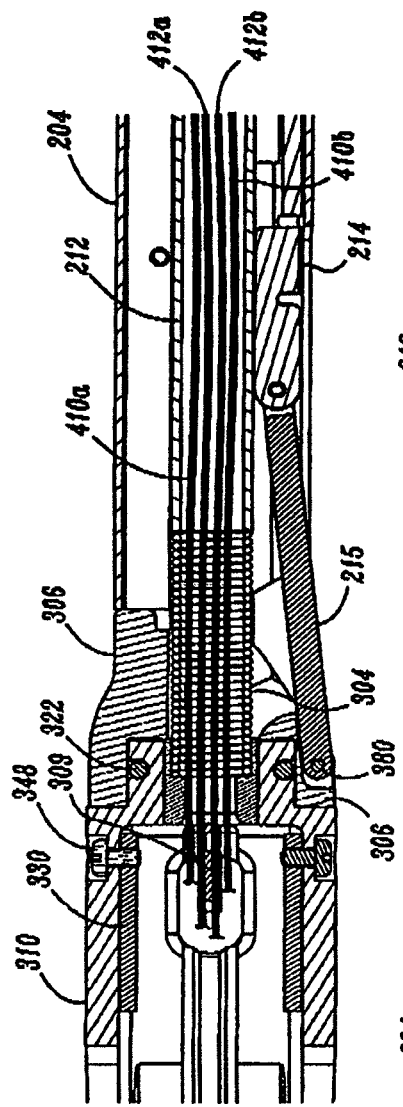
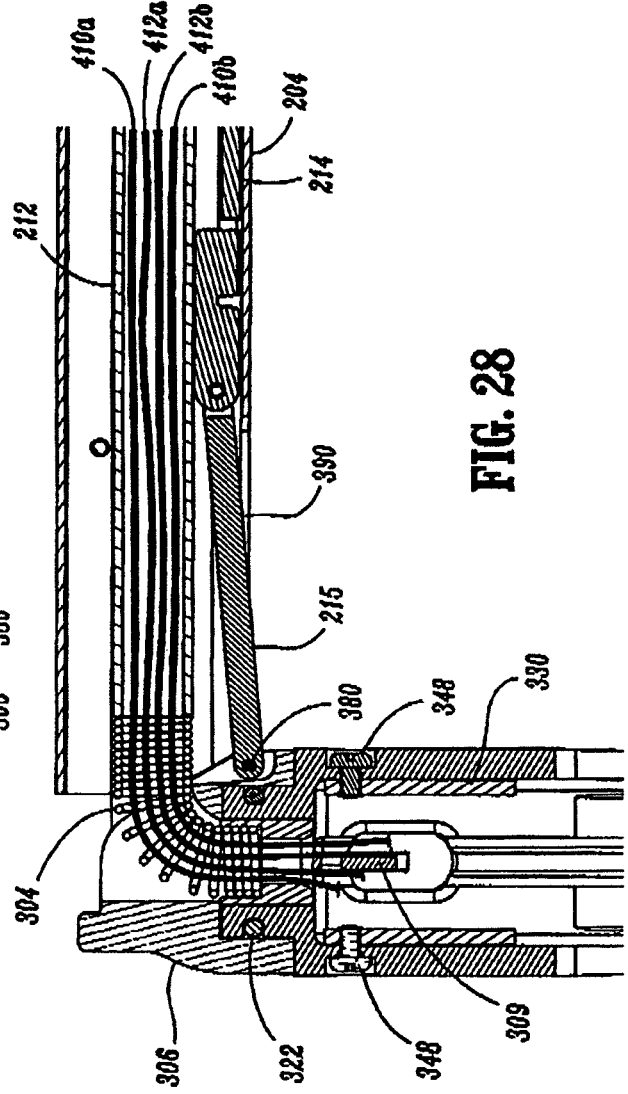
FIG. 27
FIG. 28

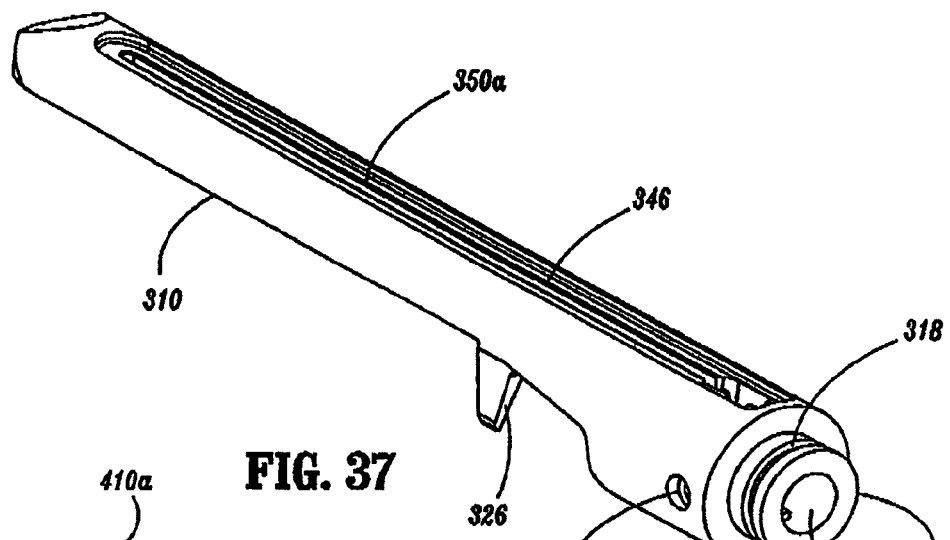
FIG. 37
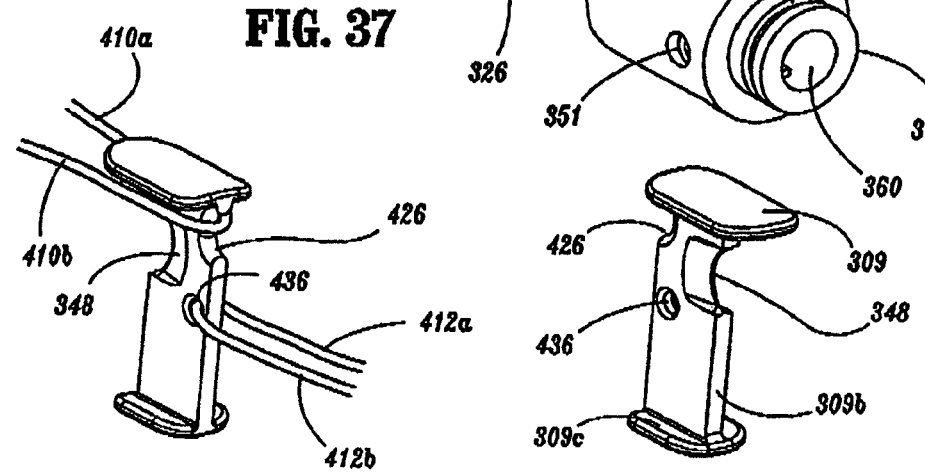
FIG. 38    FIG. 39
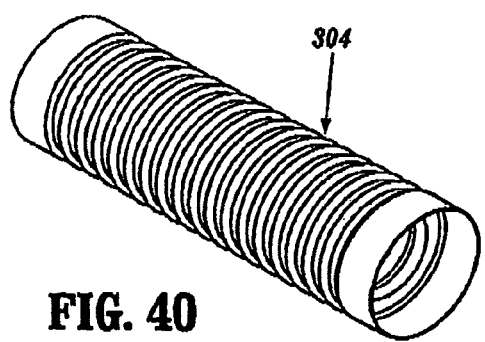
FIG. 40
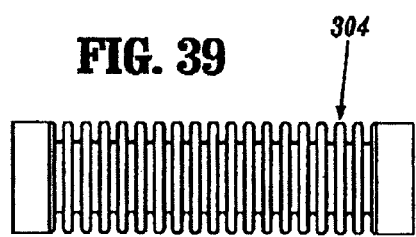
FIG. 41
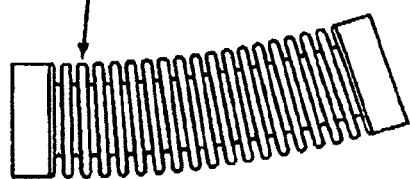
FIG. 42

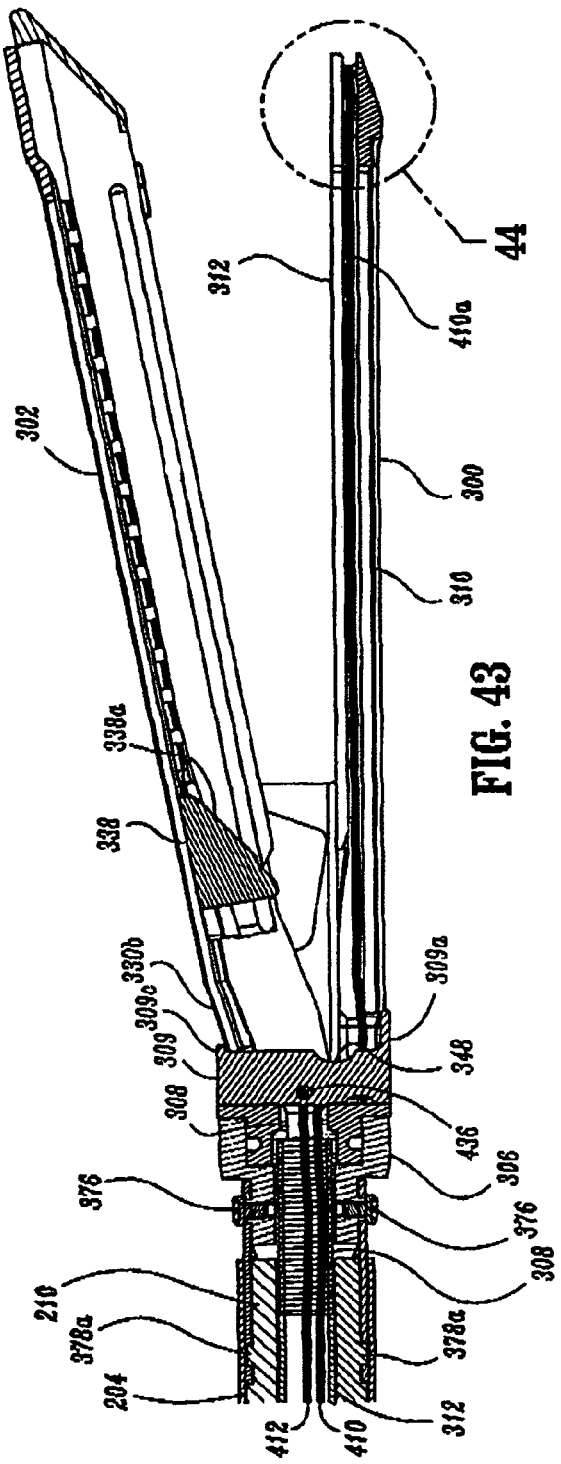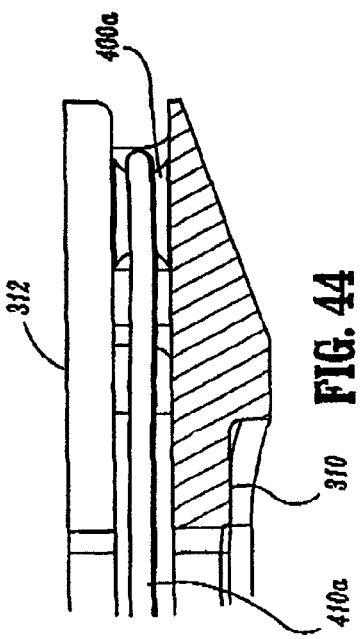
FIG. 43
FIG. 44

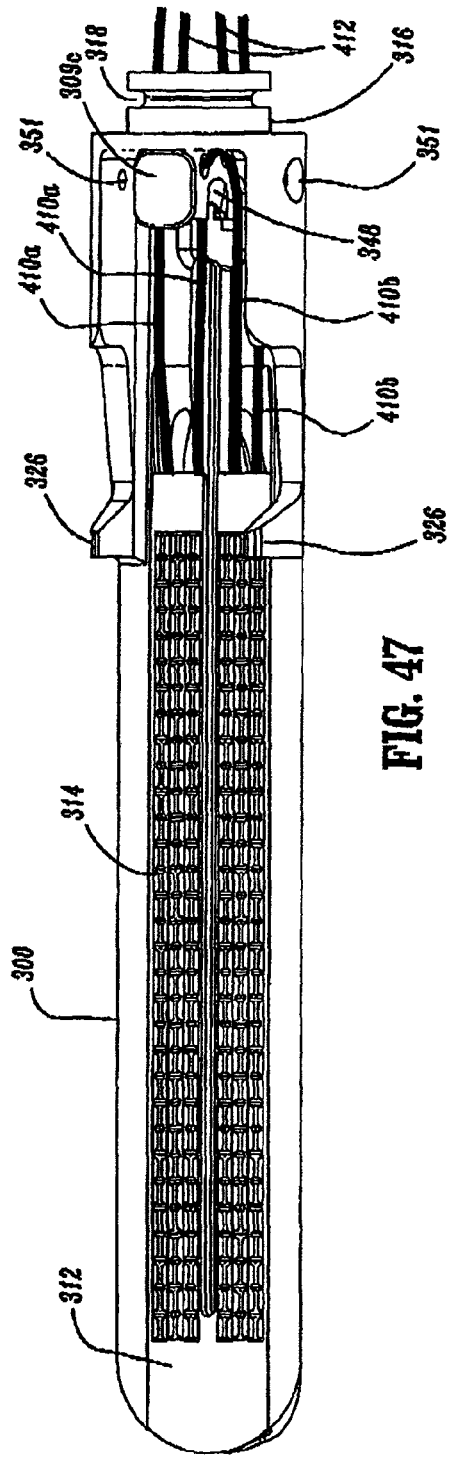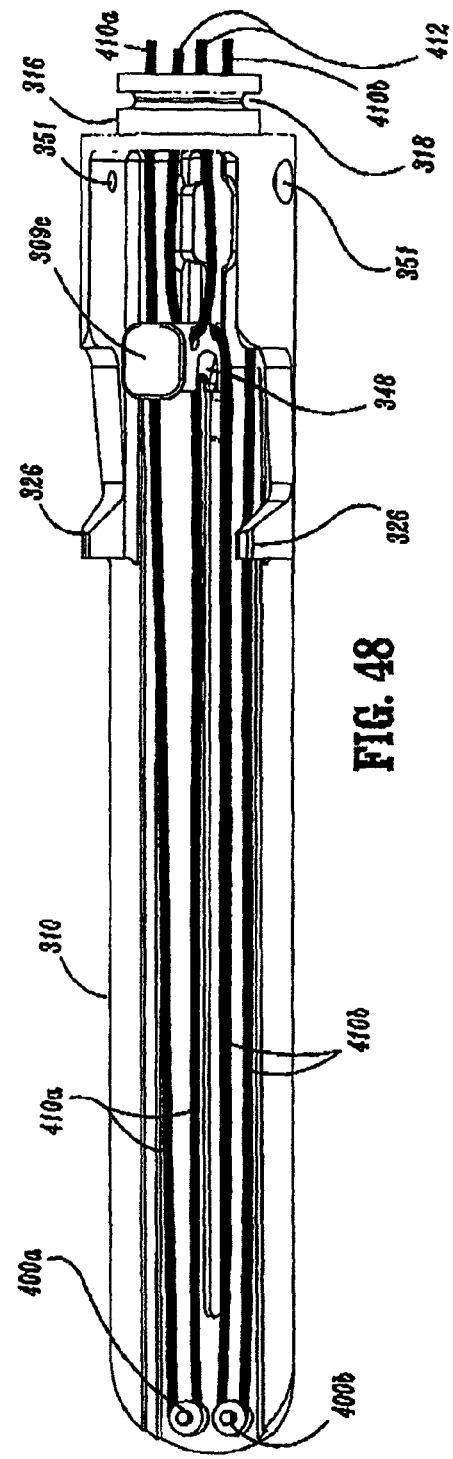

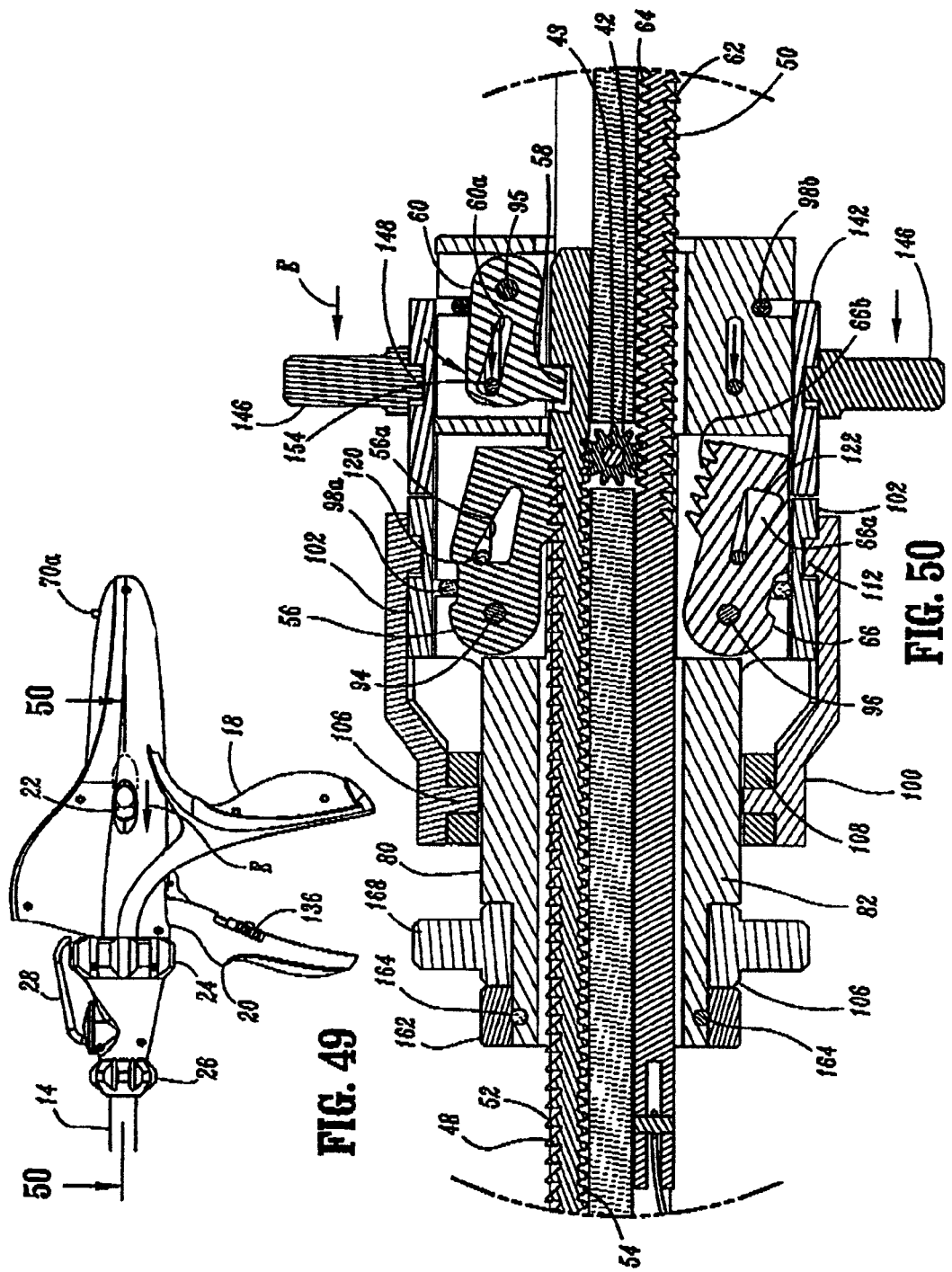

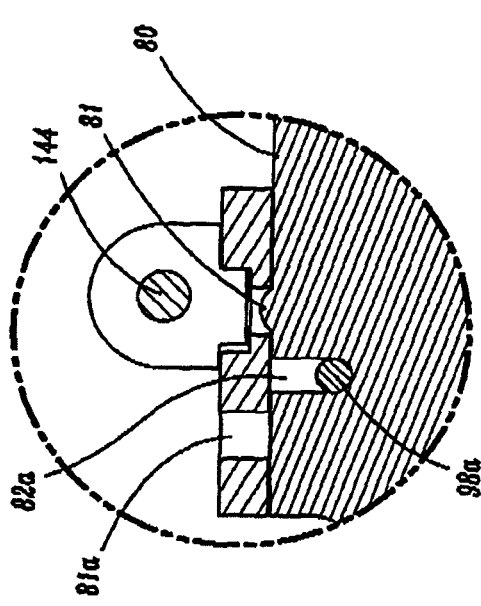
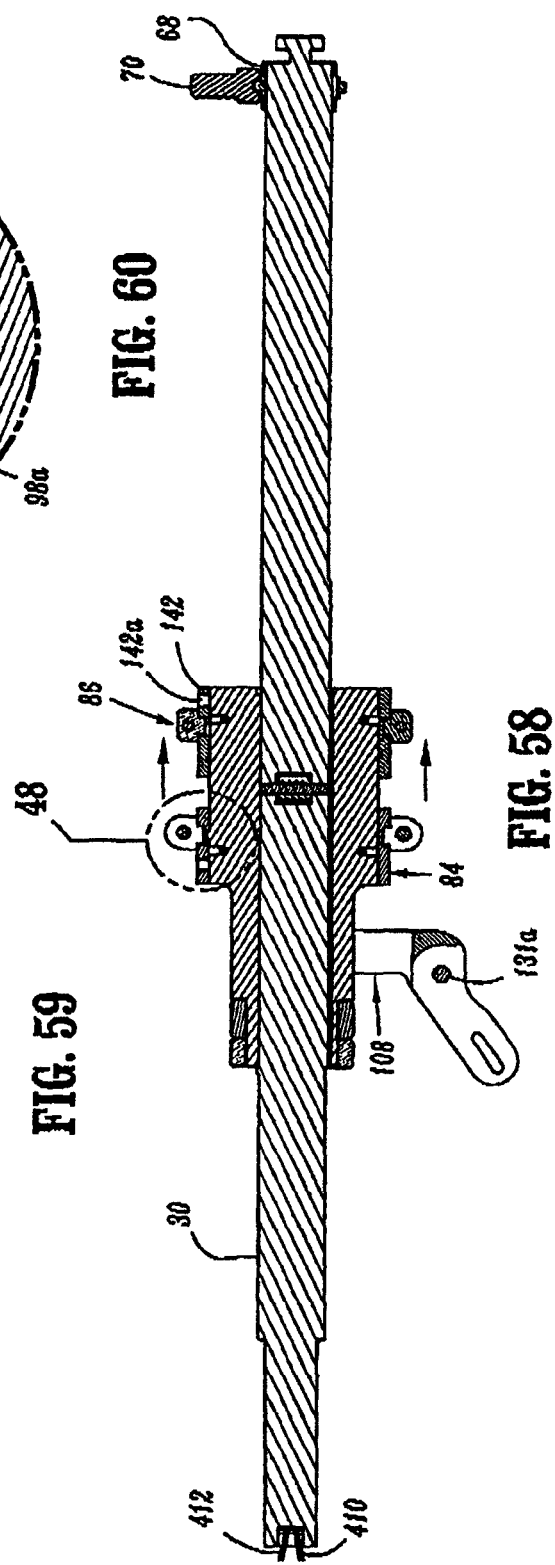

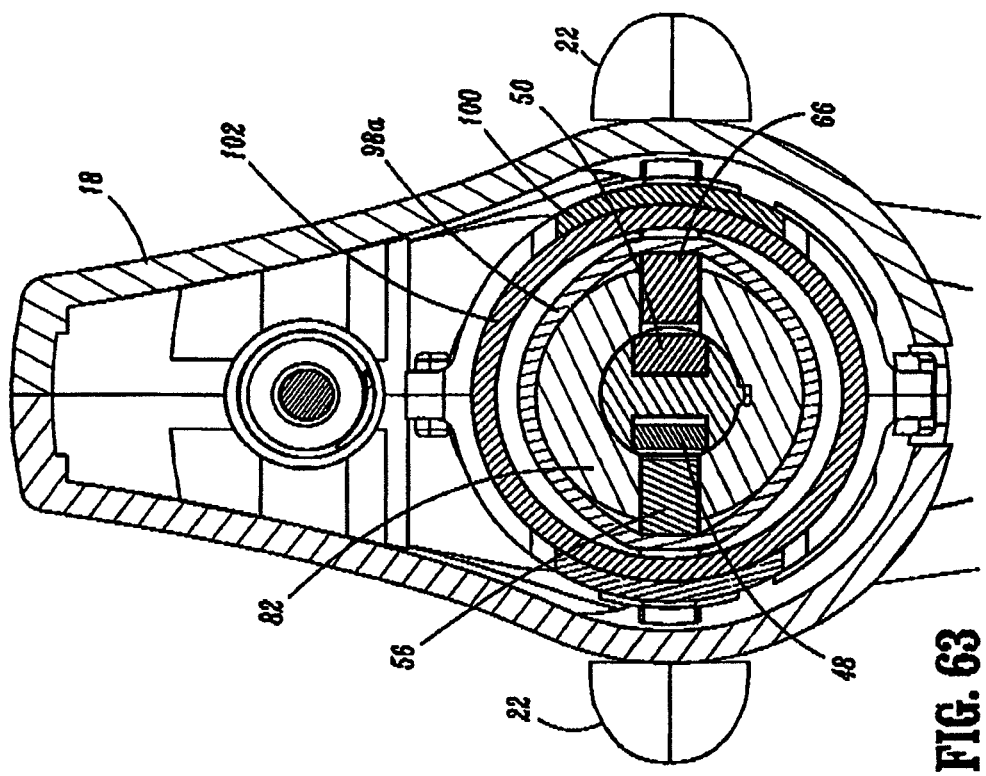
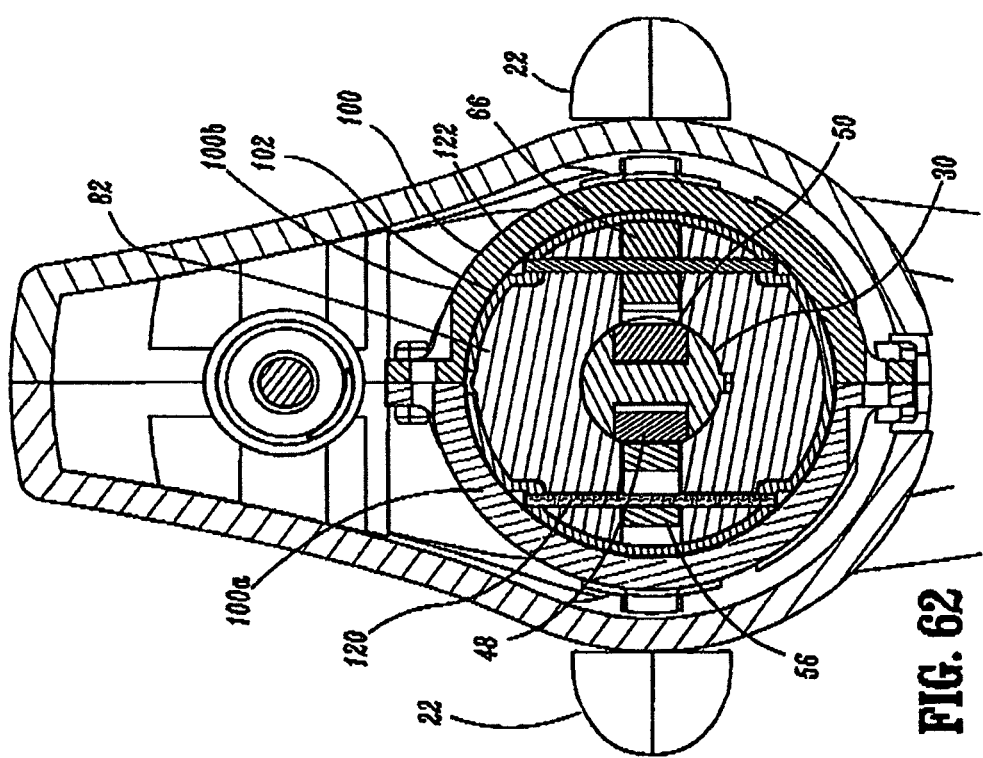

SURGICAL STAPLING DEVICE WITH INDEPENDENT TIP ROTATION

CROSS-REFERENCE TO RELATED APPLICATIONS

This application is a continuation of U.S. application Ser. No. 10/968,525 filed Oct. 18, 2004, which claims benefit of application No. 60/512,481 filed Oct. 17, 2003, and the disclosures of each of the above-identified applications are hereby incorporated by reference in their entirety.

BACKGROUND

1. Technical Field

The present application relates to a surgical stapling device and, more particularly, to an endoscopic surgical stapling device having a tool assembly and an endoscopic body portion, wherein the tool assembly is rotatable independently of the endoscopic body portion.

2. Background of Related Art

Surgical devices having a tool assembly for grasping or clamping tissue between opposing jaw structure and then joining the tissue using surgical fasteners are well known in the art. In some such devices, a knife is provided to cut the tissue which has been joined by the fasteners. The fasteners are typically in the form of surgical staples although two part fasteners are also well known.

The above-described surgical devices typically include two elongated jaw members which are movable with respect to each other to capture or clamp tissue. One of the members carries a staple cartridge which houses a plurality of staples arranged, for example, in at least two lateral rows while the other member has an anvil that defines a surface for forming staple legs as the staples are driven from the staple cartridge. Generally, the stapling operation is effected by cam members that travel longitudinally through the staple cartridge, such that the cam members engage staple pushers to sequentially eject the staples from the staple cartridge. A knife can travel between the staple rows to longitudinally cut the stapled tissue between the rows of staples. Examples of known surgical stapling devices of this type are disclosed in U.S. Pat. Nos. 5,478,003, 6,250,532 and 6,241,139 which are incorporated herein by reference in their entirety.

In endoscopic or laparoscopic procedures, surgery is performed through small incisions or through small diameter cannulas inserted through small entrance wounds in the skin. Due to the limited degree of maneuverability of a stapling device when it is positioned through the skin or a cannula, it can be difficult for a surgeon to manipulate the tool assembly of the instrument to access and/or clamp tissue. To overcome this problem, instruments having rotatable endoscopic body portions and rotatable and/or articulatable tool assemblies have been developed and are commercially available. Although these instruments provide significant improvements in the endoscopic tool art, further improvements that may decrease the time required for surgical procedures by allowing surgeons to more quickly access tissue are desired.

U.S. Pat. No. 5,478,003 ("'003 patent") discloses a surgical stapling device having a handle assembly, an elongated body portion and a fastener applying assembly. A first control mechanism is provided for rotating the elongated body and fastener applying assembly about the longitudinal axis of the elongated body portion. A second control mechanism is provided for articulating the fastener applying assembly about an axis substantially perpendicular to the longitudinal axis. A third control mechanism is provided for controlling independent rotation of the fastener applying assembly. Independent rotation of the fastener applying assembly is effected by a planetary gear assembly which drives a transmission axle and a flexible coupling. During operation of the third control mechanism, the fastener applying assembly has a tendency to lag behind operation of the control actuator. Although the stapling device disclosed in the '003 patent facilitates faster and easier access to the surgical site, a less complex more responsive surgical stapling device is desirable.

Accordingly, a continuing need exists in the art for a less complex endoscopic instrument having a tool assembly which is remotely positionable about multiple axes and is substantially directly responsive to operation of the control mechanism.

SUMMARY

In accordance with the present disclosure, a surgical stapling device is disclosed which includes a handle assembly, an endoscopic body portion and a tool assembly. The endoscopic body portion is rotatably secured to the handle assembly and defines a first longitudinal axis. The tool assembly defines a second longitudinal axis and is rotatably and pivotally supported on a distal end of the endoscopic body portion. The tool assembly is pivotal about an axis substantially perpendicular to the first longitudinal axis and rotatable about the second longitudinal axis. The surgical stapling device also includes a tool assembly rotation mechanism including a substantially rigid tube which is positioned within the endoscopic body portion and has a proximal end operably connected to a rotation knob and a distal end operably connected to a tool assembly via a flexible member. The substantially rigid tube translates rotation of the rotation knob directly to the flexible member and provides a channel for passage of firing and retraction cables for operating the tool assembly. In one embodiment, the flexible member includes a flexible bellows. In another embodiment, the flexible member includes a coil spring.

In one embodiment, the tool assembly rotation mechanism includes a first gear fixedly secured to the substantially rigid tube, a spacer tube positioned about the substantially rigid tube, a second gear rotatably supported on the spacer tube and engaged with the first gear, and a rotation knob including internal gear teeth positioned in engagement with the second gear. When the rotation knob is operated, e.g., rotated, the internal gear teeth of the rotation knob effects rotation of the second gear. Rotation of the second gear is translated into rotation of the first gear and, thus, rotation of the substantially rigid tube.

The presently disclosed surgical stapling device also includes an actuation member which is movable in relation to the tool assembly to actuate the tool assembly. The actuation member is operably connected to the handle assembly by firing and retraction cables such that movement of the operating trigger of the handle assembly effects advancement and retraction of the actuation member.

In one embodiment, the tool assembly includes a cartridge assembly for housing a plurality of staples and an anvil assembly. The anvil assembly is movable in relation to the cartridge assembly between spaced and approximated positions. It is also envisioned that the tool assembly may be other than a surgical stapling device. For example, the tool assembly may include graspers, dissectors, RF sealing devices, etc.

BRIEF DESCRIPTION OF THE DRAWINGS

Various embodiments of the presently disclosed surgical stapling device are described herein with reference to the drawings; wherein:

FIG. 2 is a side view of the surgical stapling device shown in FIG. 1;

FIG. 3 is a top view of the surgical stapling device shown in FIG. 1;

FIG. 6 is a side view of the handle assembly and proximal portion of the endoscopic body portion shown in FIG. 5;

FIG. 11A is a side perspective view from the proximal end of the firing trigger and first shift ring assembly of the surgical stapling device shown in FIG. 1;

FIG. 11B is a side perspective view from the proximal end with parts separate of the firing trigger and first shift ring assembly shown in FIG. 11A;

FIG. 18 is a side perspective view of the retraction pawl of the barrel assembly shown in FIG. 10;

FIG. 19 is a side perspective view from the proximal end of the inner ring of the first shift ring assembly of the barrel assembly shown in FIG. 10;

FIG. 20 is a side perspective view of one half-section of the outer ring of the second shift ring assembly of the barrel assembly shown in FIG. 10;

FIG. 21 is a side perspective view of one half-section of the outer ring of the first shift ring assembly of the barrel assembly shown in FIG. 10;

FIG. 27 is a cross-sectional view from the bottom of the distal end of the endoscopic body portion and the proximal end of the tool assembly with the tool assembly in a non-articulated position;

FIG. 28 is a cross-sectional view from the bottom of the distal end of the endoscopic body and the proximal end of the tool assembly with the tool assembly articulated ninety degrees;

FIG. 37 is a top perspective view from the proximal end of the anvil body portion of the tool assembly shown in FIG. 36;

FIG. 38 is a side perspective view from the proximal end of the dynamic clamping member of the tool assembly shown in FIG. 36 with the firing cable and retraction cable positioned about the dynamic clamping member;

FIG. 39 is a side perspective view from the distal end of the dynamic clamping member shown in FIG. 38;

FIG. 40 is a side perspective view of the torque transmitting member of the tool assembly shown in FIG. 36;

FIG. 41 is a side view of the torque transmitting member shown in FIG. 40;

FIG. 42 is a side view of the torque transmitting member shown in FIG. 41 in a slightly bent configuration;

FIG. 43 is a side cross-sectional view of the distal end of the endoscopic body portion and tool assembly of the surgical stapling device shown in FIG. 1 through a cam surface of the drive sled;

FIG. 44 is an enlarged view of the indicated area of detail shown in FIG. 43;

FIG. 47 is a top view of the anvil assembly of the surgical stapling device shown in FIG. 1 with the retraction and firing cables positioned about the dynamic clamping member;

FIG. 48 is a top view of the anvil assembly shown in FIG. 47 with the anvil plate removed;

FIG. 49 is a side view of the handle assembly and proximal portion of the endoscopic body portion of the surgical stapling device shown in FIG. 1 with the grasper button moved to the forward position;

FIG. 50 is an enlarged cross-sectional view taken along section lines 50-50 of FIG. 49 of the spindle and barrel assembly;

FIG. 58 is a top cross-sectional view of the spindle and barrel assembly shown in FIG. 57;

FIG. 59 is an enlarged view of the indicated area of detail shown in FIG. 57;

FIG. 60 is an enlarged view of the indicated area of detail shown in FIG. 59;

FIG. 62 is a cross-sectional view taken along section line 62-62 of FIG. 61;

FIG. 63 is a cross-sectional view taken along section line 63-63 of FIG. 61;

DETAILED DESCRIPTION OF EMBODIMENTS

Figure 1:
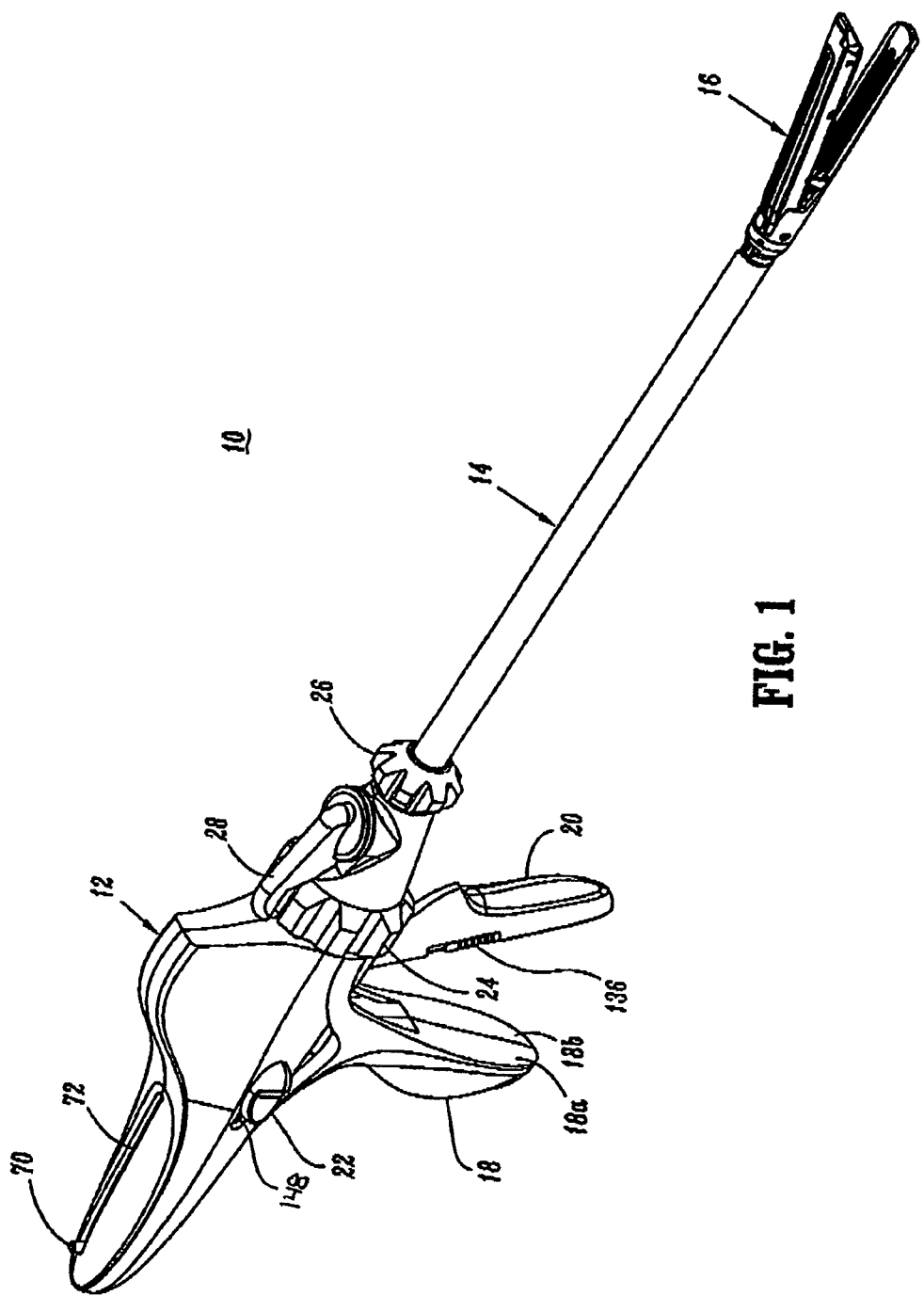
FIG. 1 is a side perspective view from the distal end of the presently disclosed surgical stapling device with the tool assembly in the open position.

Embodiments of the presently disclosed surgical stapling device will now be described in detail with reference to the drawings in which like reference numerals designate identical or corresponding elements in each of the several views.

FIGS. 1-3 illustrate one embodiment of the presently disclosed surgical stapling device shown generally as 10. Briefly, surgical stapling device 10 includes a handle assembly 12, an endoscopic body portion 14 and a tool assembly 16. Handle assembly 12 includes a stationary handle portion 18 and a firing or operating trigger 20. A grasper button 22 is movably positioned on handle assembly 12 adjacent stationary handle portion 18. A body rotation knob 24 is rotatably supported adjacent a distal end of handle assembly 12 and a tool assembly rotation knob 26 is rotatably supported adjacent the distal end of rotation knob 18. Rotation knob 24 may be formed from molded half-sections 24a and 24b which are secured together using any known fastening technique, e.g., screws 25. An articulation lever 28 is pivotally supported on rotation knob. The function of each of the knobs and buttons will be discussed in further detail below.

Referring to FIGS. 4-14, stationary handle portion 18 includes half-sections 18a and 18b (FIG. 9) which can be molded from a thermoplastic material, e.g., polycarbonate. Alternately, other known materials suitable for surgical use and having the requisite strength characteristics may be used. Handle half-sections 18a and 18b are secured together using a known fastening technique, e.g., adhesives, welding, screws, interlocking structure, etc.

Figure 8:
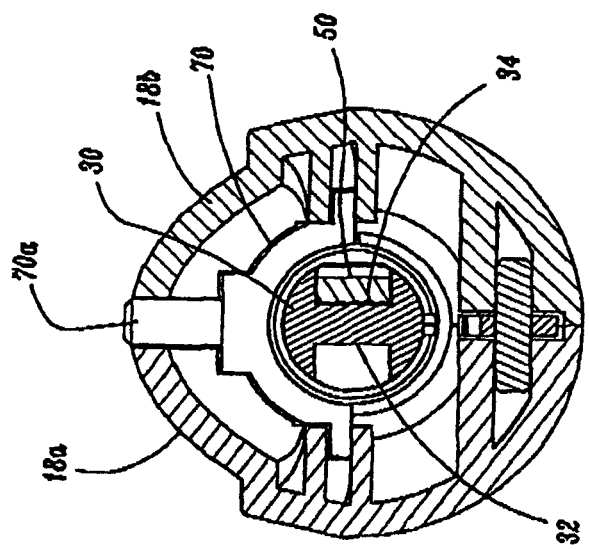
FIG. 8 is a cross-sectional view taken along section lines 8-8 of FIG. 6.
Figure 7:
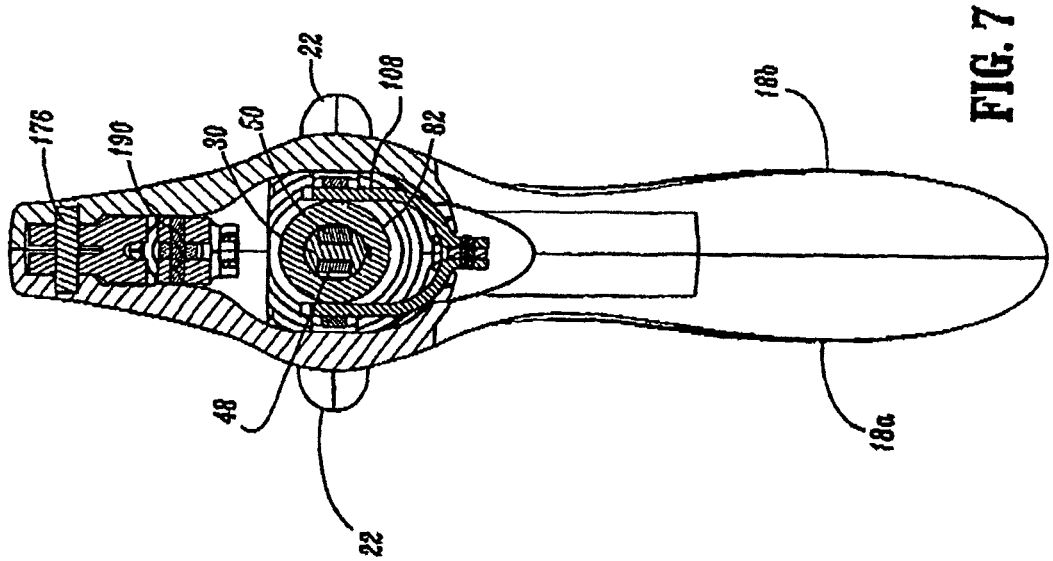
FIG. 7 is a cross-sectional view taken along section lines 7-7 of FIG. 6.

Handle assembly 12 includes an approximation and firing mechanism which includes a spindle 30 (FIG. 12) which has diametrically opposed guide tracks 32 and 34 (FIG. 8). The proximal end of spindle 30 includes an extension 36 which defines an annular slot 38. Extension 36 is rotatably received within a recess 40 (FIG. 4) formed in stationary handle portion 18 to rotatably fasten spindle 30 within stationary handle portion 18. A wall 40a defining recess 40 extends into slot 38 of spindle 30 to axially fix spindle 30 within handle portion 18. A pinion 42 is rotatably fastened about a pin 43 within a throughbore 44 (FIG. 14) formed in spindle 30. Pinion 42 includes gear teeth 46 which extend into guide tracks 32 and 34 of spindle 30.

A firing rack 48 is slidably received in guide track 32 of spindle 30 and a retraction rack 50 is slidably received in guide track 34 of spindle 30. Firing rack 48 includes gear teeth 52 and 54 formed on opposite sides of firing rack 48. Gear teeth 52 are positioned to engage teeth of an advancement and firing pawl 56 ("firing pawl") and gear teeth 54 are positioned to engage the teeth of pinion 42. The proximal end of firing rack 48 includes a cutout 58 which is dimensioned to receive an engagement member 60a of a grasper pawl 60 in a manner to be discussed in detail below. Retraction rack 50 also includes gear teeth 62 and 64 formed on opposite sides thereof. Gear teeth 62 are positioned to engage the teeth of a retraction pawl 66 and gear teeth 64 are positioned to engage teeth 46 of pinion 42. The proximal end of retraction rack 50 includes a bore for receiving a pin 68b (FIG. 11) of an indicator ring 68. Indicator ring 68 is slidably positioned about spindle 30 and is secured to and movable with retraction rack 50. In one embodiment, indicator ring 68 includes an indicator member 70 which is secured to indicator ring 68 and has a radial extension 70a which extends through and is movable within an elongated slot 72 formed in handle portion 18. The location of extension 70a along slot 72 provides a visual indication to a surgeon of the stage of operation of stapling device 10. The extension may be colored to facilitate viewing, e.g., red. Alternately, a window or transparent portion (not shown) may be provided in stationary handle portion 18 to facilitate direct viewing of the position of indicator ring 60 on spindle 30. Indicia may be provided on handle portion 18 adjacent the window or slot 72 to specify the stage of operation of the device (retracted, partially approximated, fully approximated, etc. . . . ) with reference to the position of indicator ring 68 on spindle 30. Either indicator ring 68 or indicator member 70 may include a pair of diametrically opposed wings 68a which are slidably received in guide slots 74 (FIG. 7) formed in each handle half-section 18a and 18b.

Figure 11:
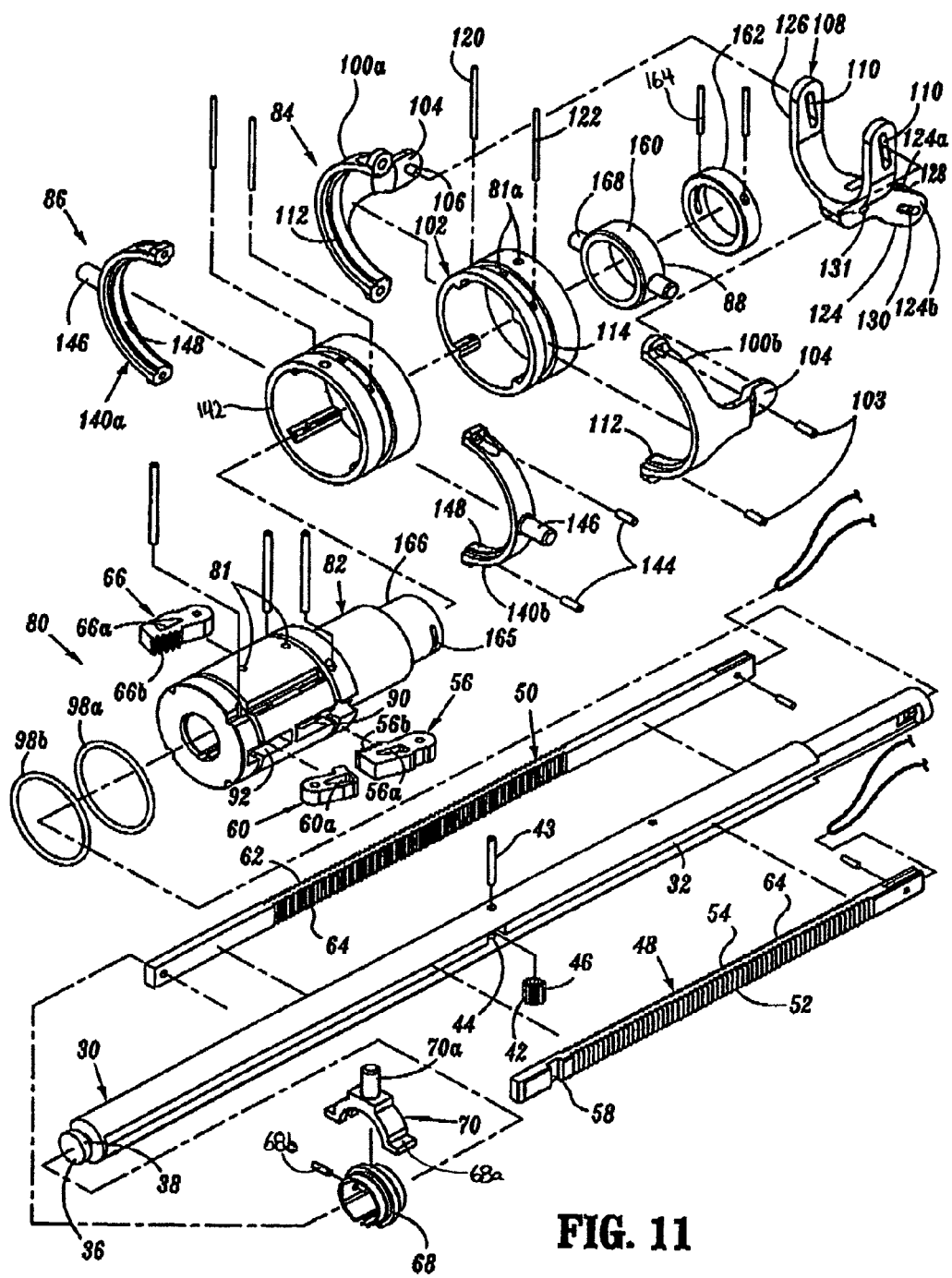
FIG. 11 is a perspective view from the distal end with parts separated of the spindle and barrel assembly shown in FIG. 10.

A barrel assembly 80 is slidably positioned about spindle 30. Barrel assembly 80 includes firing pawl 56, grasper pawl 60, retraction pawl 66, a body portion 82, first and second shift ring assemblies 84 and 86, and a trigger connector 88. Barrel assembly body portion 82 (FIGS. 16-18) includes a pair of axially spaced bores 90 and 92 (FIG. 11). Firing pawl 56 is pivotally secured within bore 90 about a pivot pin 94 which extends through barrel assembly body portion 82. Retraction pawl 66 is pivotally secured within an opposite side of throughbore 90 about a pivot pin 96 which extends through barrel assembly body portion 82. A biasing member or O-ring 98a is positioned within an annular slot 82a in body portion 82 of barrel assembly 82 about firing pawl 56 and retraction pawl 66 to urge firing pawl 56 and retraction pawl 66 into engagement with firing rack 48 and retraction rack 50, respectively. Alternately, other biasing devices, e.g., coil springs, may be used to bias the firing pawl and retraction pawl into engagement with the firing and retraction racks, respectively. Firing pawl 56 includes a cam slot 56a, and a series of teeth 56b configured to engage teeth 52 of firing rack 48. Retraction pawl 66 includes a cam slot 66a and a series of teeth 66b configured to engage teeth 62 of retraction rack 50.

Figure 61:
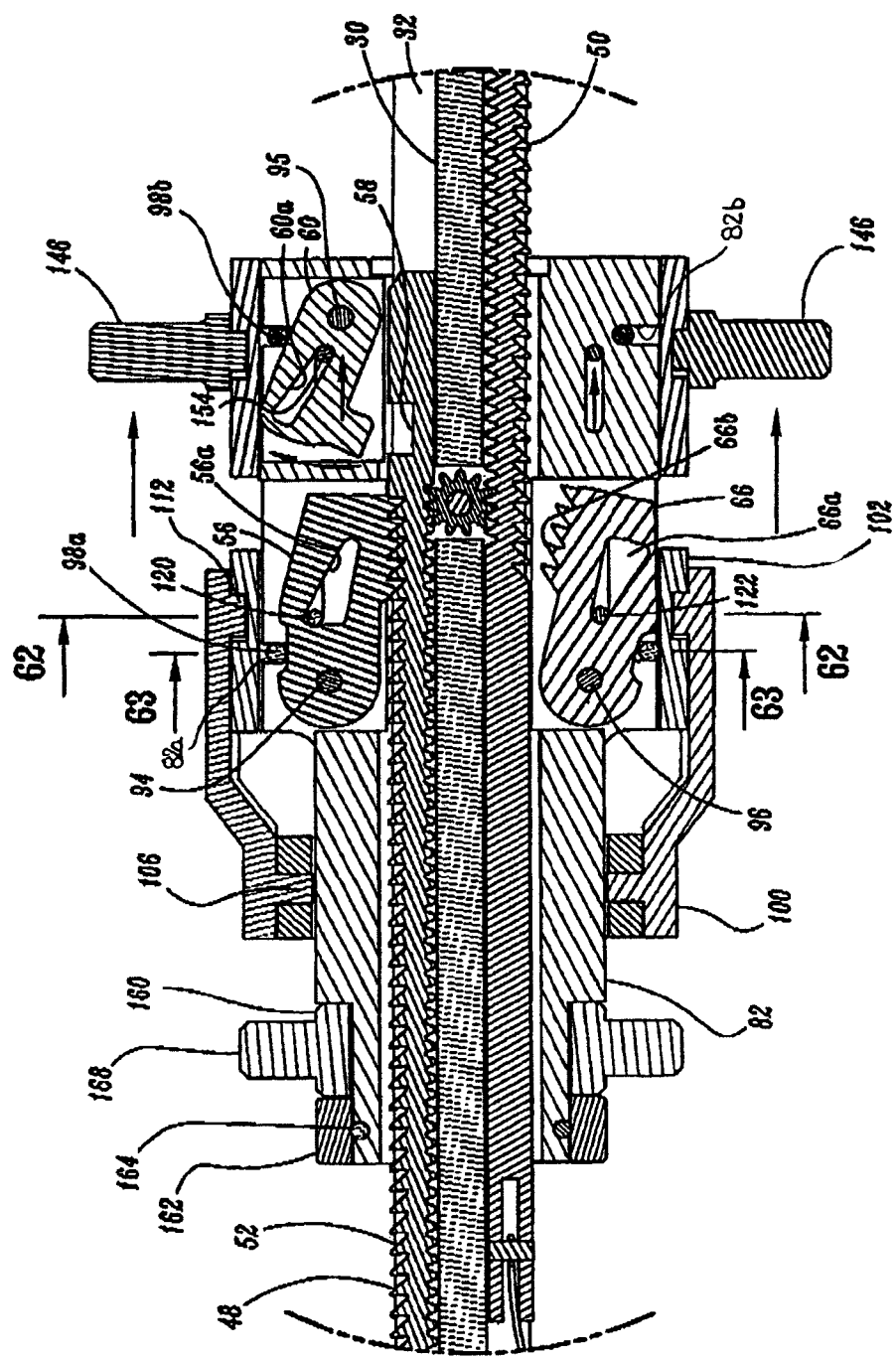
FIG. 61 is an enlarged view of the indicated area of detail shown in FIG. 57.

Grasper pawl 60 is pivotally secured in one end of throughbore 92 about a pivot pin 95 and includes a cam slot 60a. A biasing member, e.g., O-ring 98b, is positioned within an annular slot 82b (FIG. 61) in body portion 82 in engagement with grasper pawl 60 to urge engagement finger 60b of grasper pawl 60 into cutout 58 of firing rack 48. Operation of grasper pawl 60 will be discussed in further detail below.

First shift ring assembly 84 includes an outer ring 100 and an inner ring 102. In one embodiment, outer ring 100 is formed from a pair of half-sections 100a and 100b which can be fastened together using any known fastening technique, e.g., pins 103. Each half-section 100a and 100b has a finger 104 extending distally therefrom. A projection or pin 106 extends radially inwardly from each finger 104. Projections 106 may be separate from or formed integrally with fingers 104 and are dimensioned to be received within cam slots 110 formed in a lever 108 which will be discussed in further detail below. An inner surface of outer ring 100 includes an annular rib 112.

Inner ring 102 includes an outer annular groove 114 dimensioned to receive annular rib 112 of outer ring 100. Engagement between annular rib 112 and annular groove 114 prevents axial movement of outer ring 100 in relation to inner ring 102 while permitting rotation of outer ring 100 in relation to inner ring 102. A plurality of ridges 116 are formed along an inner surface of inner ring 102. Ridges 116 are slidably received in grooves 118 formed in body portion 82 of barrel assembly 80. Engagement between ridges 116 and grooves 118 rotatably fix inner ring 102 to body portion 82 while permitting axial movement of inner ring 102 in relation to body portion 82 of barrel assembly 80.

Figure 16:
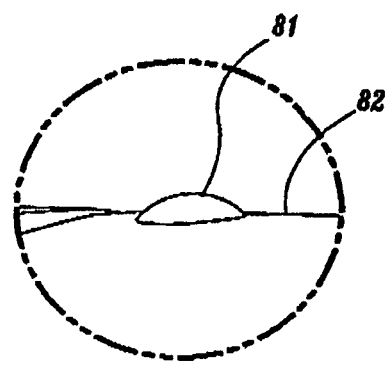
FIG. 16 is an enlarged view of the indicated area of detail shown in FIG. 17.
Figure 17:
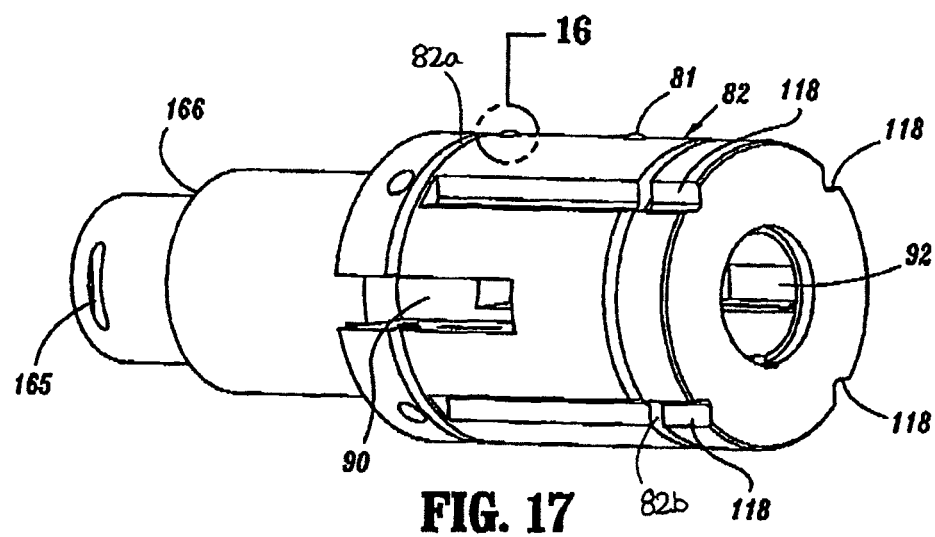
FIG. 17 is a side perspective view from the proximal end of the body portion of the barrel assembly shown in FIG. 15.

Timer ring 102 is positioned about body portion 82 of barrel assembly 80 and outer ring 100 is positioned about inner ring 102. As discussed above, inner ring 102 is axially slidable but rotatably fixed in relation to body portion 82, and inner ring 102 is axially fixed but rotatable in relation to outer tube 100. A pair of cam members, e.g., pins 120 and 122, extend from one side of inner ring 102 across an inner bore defined by inner ring 102 to the other side of inner ring 102. First cam member 120 extends through cam slot 56a formed in firing pawl 56 and second cam member 122 extends through cam slot 66a of retraction pawl 66 (See FIG. 50). When outer ring 100 is moved axially between advanced and retracted positions about body portion 82 of barrel assembly 80 by actuation of lever 108, as will be discussed in further detail below, inner ring 102 is moved therewith to effect movement of cam members 120 and 122 within cam slots 56a and 66a, respectively, of firing pawl 56 and retraction pawl 66, respectively. Cam slots 56a and 66a are configured to allow O-ring 98a to urge and position firing pawl 56 in engagement with firing rack 48 when outer ring 100 is moved by lever 108 to its advanced position and to allow O-ring 98a to position retraction pawl 66 in engagement with retraction rack 50 when outer ring 100 is moved by lever 108 to its retracted position. When outer ring 100 and thus, inner ring 102, are in their advanced position about barrel assembly 80, cam member 122 is engaged with a surface of cam slot 66a to prevent engagement of retraction pawl 66 with retraction rack 50. When outer ring 100 and inner ring 102 are in their retracted position about barrel assembly 80, cam member 120 is engaged with a surface defining cam slot 56a to prevent engagement between firing pawl 56 and firing rack 48. Referring to FIG. 16, the outer surface of body portion 82 of barrel assembly 80 includes a plurality of resilient nubs 81 which are received in openings 81a (FIG. 60) formed in inner ring 102 to retain the inner ring 102 in its advanced or retracted position.

Figure 11D:
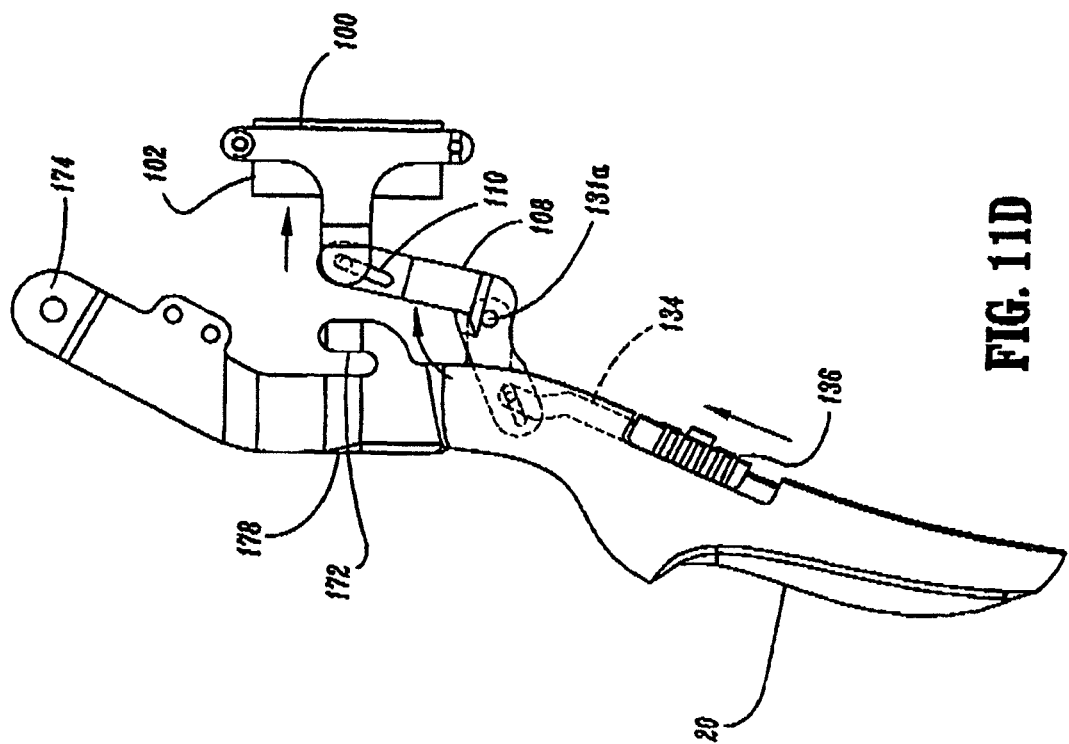
FIG. 11D is a side partial phantom view of the firing trigger and first shift ring assembly shown in FIG. 11C with the selector switch moved to move the first shift ring assembly to its retracted position.
Figure 11C:
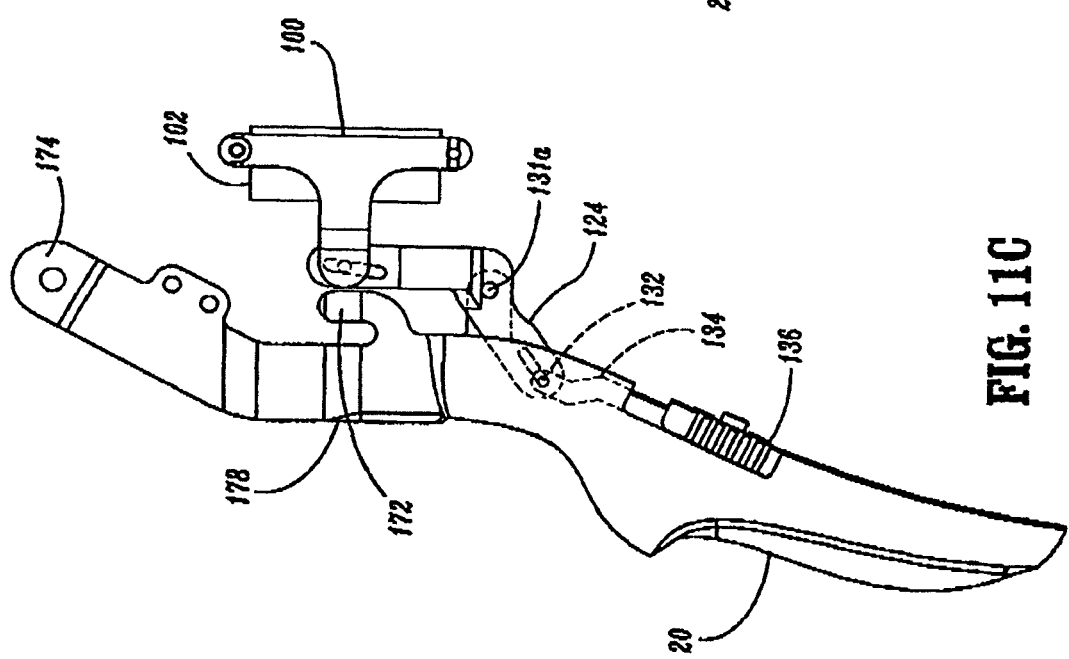
FIG. 11C is a side partial phantom view of the firing trigger and first shift ring assembly shown in FIG. 11A with the first shift ring assembly in its advanced position.
Figure 14:
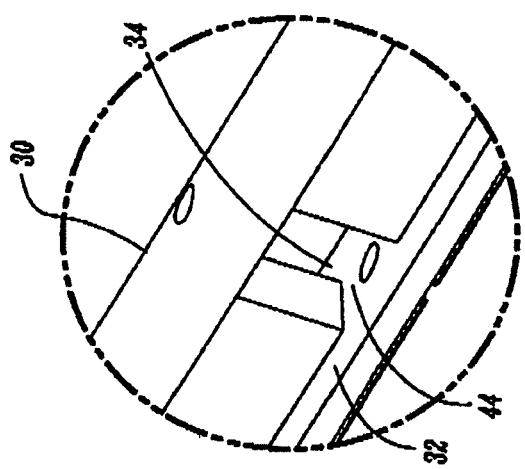
FIG. 14 is an enlarged view of the indicated area of detail shown in FIG. 12.
Figure 12:
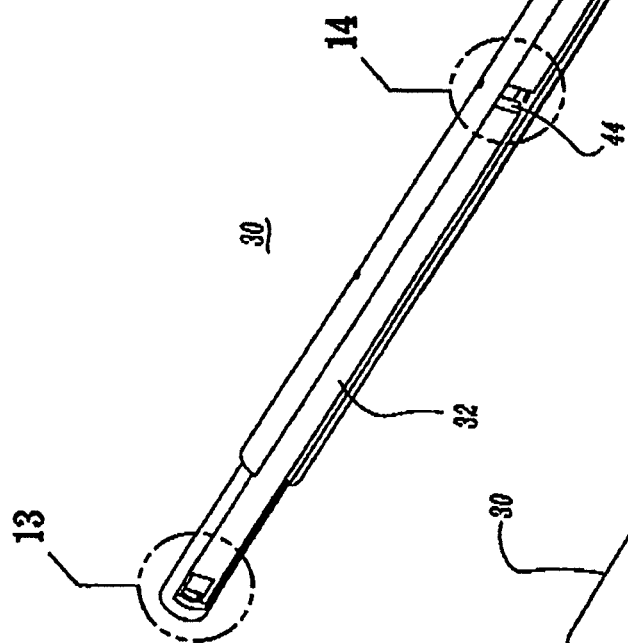
FIG. 12 is a top perspective view of the spindle shown in FIG. 11.
Figure 13:
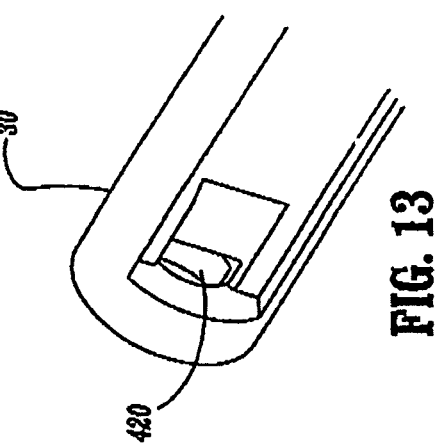
FIG. 13 is an enlarged view of the indicated area of detail shown in FIG. 12.
Figure 15:
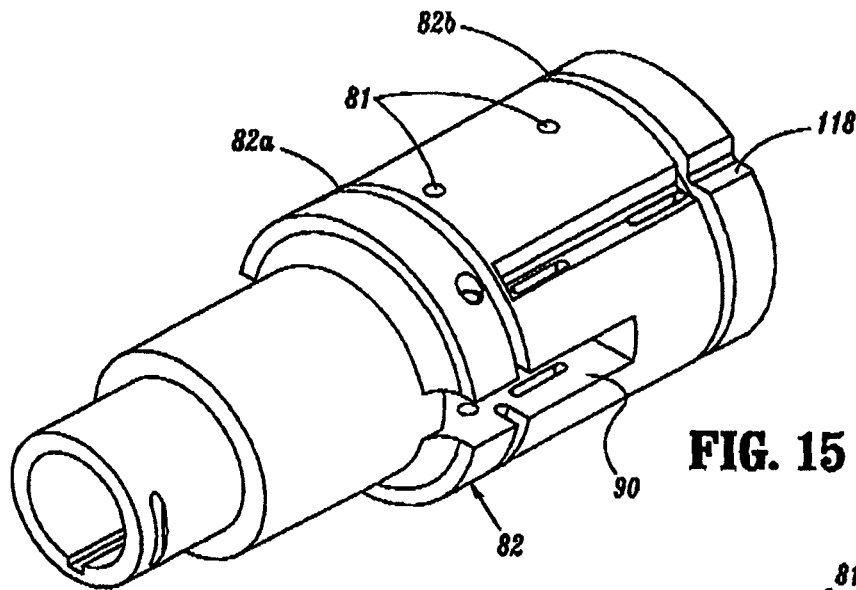
FIG. 15 is a side perspective from the distal end of the body portion of the barrel assembly shown in FIG. 11.

Referring to FIGS. 11-11D, lever 108 includes an arm 124 and a U-shaped collar 126 which is positioned partially about body portion 82 of barrel assembly 80. Cam slots 110 are formed in opposite ends of U-shaped collar 126 and slidably receive projections 106 of outer ring 100. Arm 124 of lever 108 includes a pair of spaced body members 124a and 124b which define a channel 128 therebetween (FIG. 11). Body members 124a and 124b each include an elongated slot 130 formed on one end thereof and a bore 131 formed in an opposite end thereof. Pin 132 connects arm 124 to the distal end of a link 134 and bore 131 receives a pivot pin 131a for pivotally securing lever 108 to an extension 20a formed on firing trigger 20. Link 134 is connected to or, formed monolithically with a selector switch 136 which is slidably supported on firing trigger 20. Selector switch 136 is positioned on firing trigger 20 such that it can be engaged from either side or the back of firing trigger 20.

When selector switch 136 is slid along firing trigger 20 in the direction indicated by arrow "A" in FIG. 6, lever 108 is pivoted about pivot pin 131a to move U-shaped collar 126 proximally about body portion 82 of barrel assembly 80. Movement of U-shaped collar 126 proximally effects movement of outer ring 100 about body portion 82 of barrel assembly 80 proximally, via projections 106, to move inner ring 102 of first shift ring 84 proximally from its advanced position to its retracted position. As discussed above, when inner ring 102 is moved to its retracted position, retraction pawl 66 is urged into engagement with retraction rack 50 by O-ring 98a and firing pawl 56 is pivoted from engagement with firing rack 48 against the bias of O-ring 98a by cam member 120.

Second shift ring assembly 86 includes an outer ring 140 and an inner ring 142. In one embodiment, outer ring 140 is formed from a pair of half-sections 140a and 140b which can be fastened together using known fastening techniques, e.g., pins 144. Each half-section 140a and 140b has a post 146 extending radially outwardly therefrom. Posts 146 are dimensioned to extend through respective slots 148 (FIG. 1) formed in stationary handle portion 18 and support a respective grasper button 22. An inner surface of outer ring 140 includes an annular rib 148.

Inner ring 142 includes an outer annular groove 150 dimensioned to receive annular rib 148 of outer ring 140. Engagement between annular rib 148 and annular groove 150 prevents axial movement of outer ring 140 in relation to inner ring 142 while permitting rotation of outer ring 140 in relation to inner ring 142. A plurality of ridges 152 are formed along an inner surface of inner ring 142. Ridges 152 are slidably received in grooves 118 formed in body portion 82 of barrel assembly 80. Engagement between ridges 152 and grooves 118 rotatably fix inner ring 142 to body portion 82 while permitting axial movement of inner ring 142 in relation to body portion 82.

Figure 69:
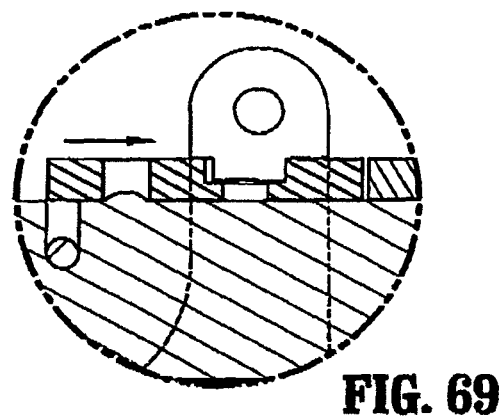
FIG. 69 is enlarged view of the indicated area of detail shown in FIG. 68.

Inner ring 142 is positioned about body portion 82 of barrel assembly 80 and outer ring 140 is positioned about inner ring 142. As discussed above, inner ring 142 is axially slidable but rotatably fixed in relation to body portion 82, and inner ring 142 is axially fixed but rotatable in relation to outer ring 140. A cam member, e.g., a rod or pin 154, extends from one side of inner ring 142 across an inner bore defined by inner ring 142 to an opposite side of inner ring 142. Cam member 154 extends through a cam slot 60a formed in grasper pawl 60. Inner ring 142 is axially movable along an outer surface of body portion 82 of barrel assembly 80 from an advanced position to a retracted position, via manual movement of grasper button 22, to move cam member 154 within cam slot 60a of grasper pawl 60. When inner ring 142 is moved to its retracted position, cam member 154 is engaged with a wall or surface defining cam slot 60a to urge grasper pawl 60 out of engagement with firing rack 48 against the bias of O-ring 98b. When inner ring 142 is in its advanced position, cam member 154, in combination with O-ring 98b, urges grasper pawl into engagement with firing rack 48. Openings 142a formed in inner ring 142 receive nubs 81 formed on barrel assembly body portion 82 to releaseably retain inner ring 142 in its respective advanced and retracted positions (FIG. 69).

Referring to FIG. 11, barrel assembly 80 also includes a trigger connector 88 which includes an annular member 160 rotatably secured about a distal end of barrel assembly body portion 82 by a cap or ring 162. Cap 162 can be secured to the distal end of barrel assembly body portion 82 by a pair of pins 164 such that annular member 160 is supported on the distal end of barrel assembly body portion 82 between cap 162 and a shoulder 166 of barrel assembly body portion 82. Pins 164 extend through grooves 165 formed in body portion 82 of barrel assembly 80. Alternately, other fastening techniques may be used to secure the cap to the barrel assembly body portion, e.g., screw threads, adhesives, welding, etc. Annular member 160 includes a pair of prongs 168 positioned and configured to engage firing trigger 20 in a manner to be described below.

Figure 5:
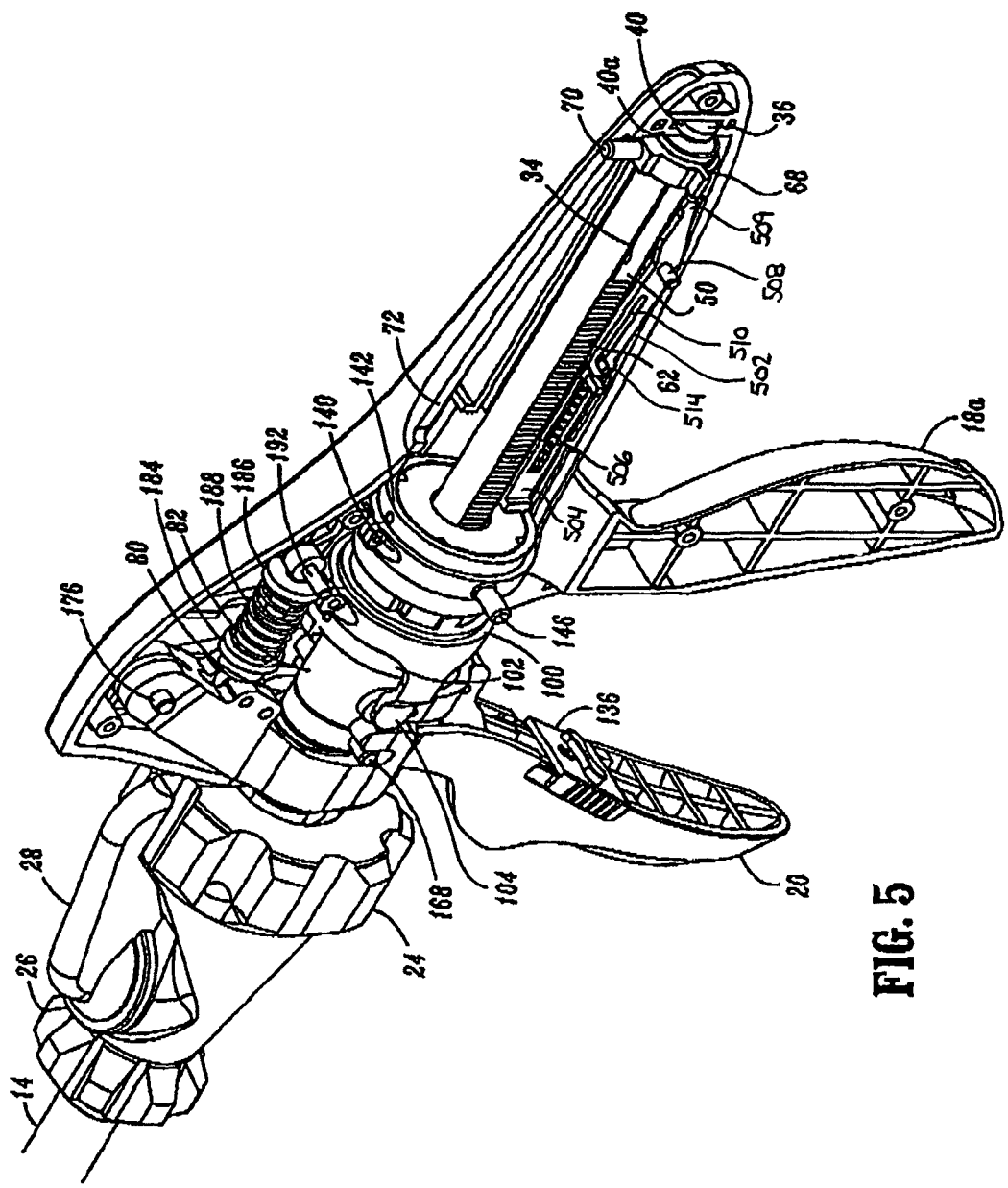
FIG. 5 is a side perspective view from above of the handle assembly and proximal portion of the endoscopic body portion with a handle half-section removed.

Referring to FIGS. 11A-11D, firing trigger 20 includes a grip portion 170, an engagement portion 172 and a pivot portion 174. Pivot portion 174 is formed at a top end of firing trigger 20 and is configured to be pivotally secured between handle half-sections 18a and 18b about a pivot member 176 (FIG. 5). Engagement portion 172 of firing trigger 20 includes a cylindrical member 178 positioned about body portion 82 of barrel assembly 80 and a pair of U-shaped hook members 180. Hook members 180 are dimensioned to slidably receive prongs 168 of annular member 160 (FIG. 11) such that pivotal movement of firing trigger 20 about pivot member 176 is translated to linear movement of barrel assembly 80 about spindle 30.

Figure 4:
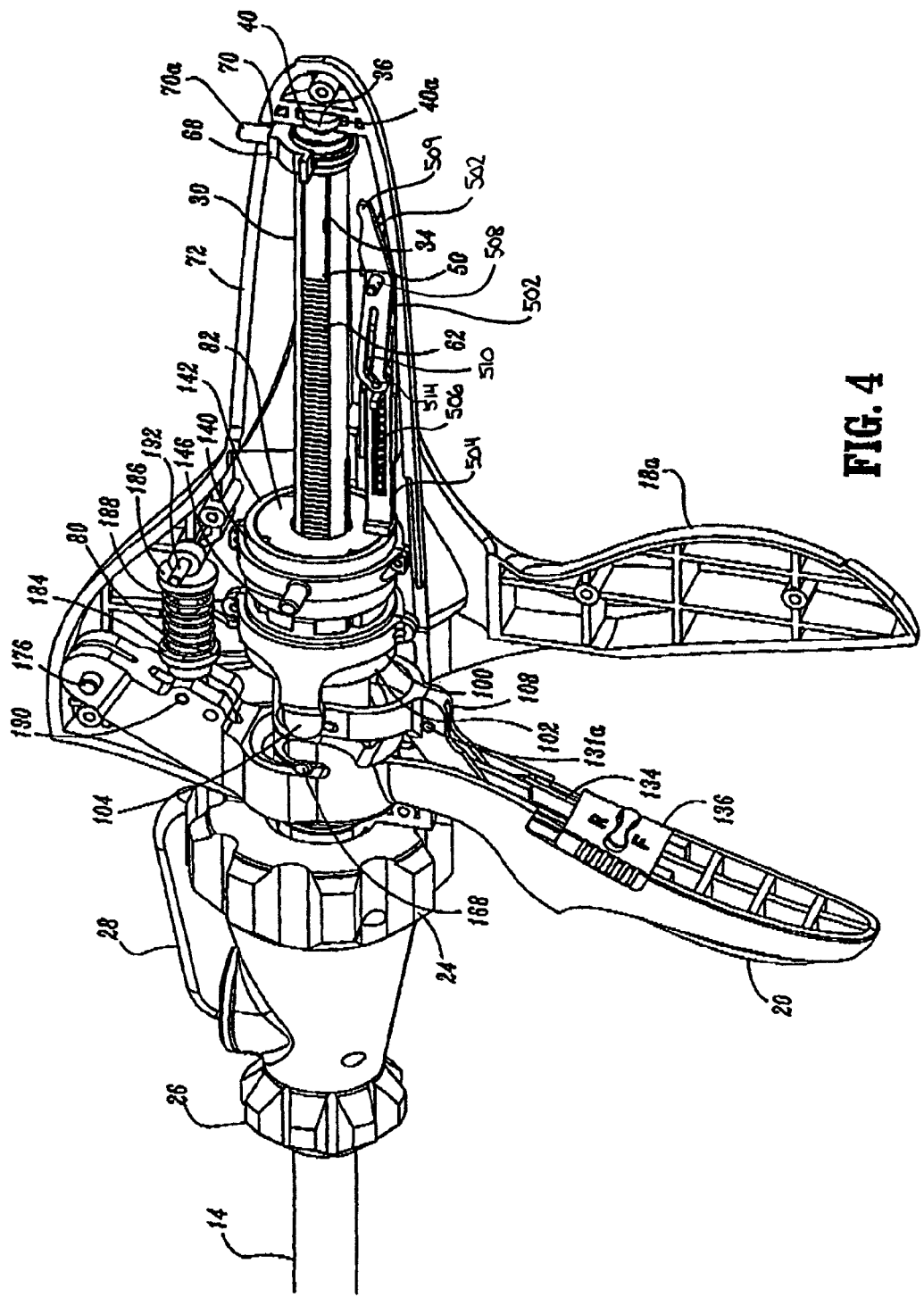
FIG. 4 is a side perspective view from the proximal end of the handle assembly and proximal portion of the endoscopic body portion with a handle half-section removed.
Figure 9:
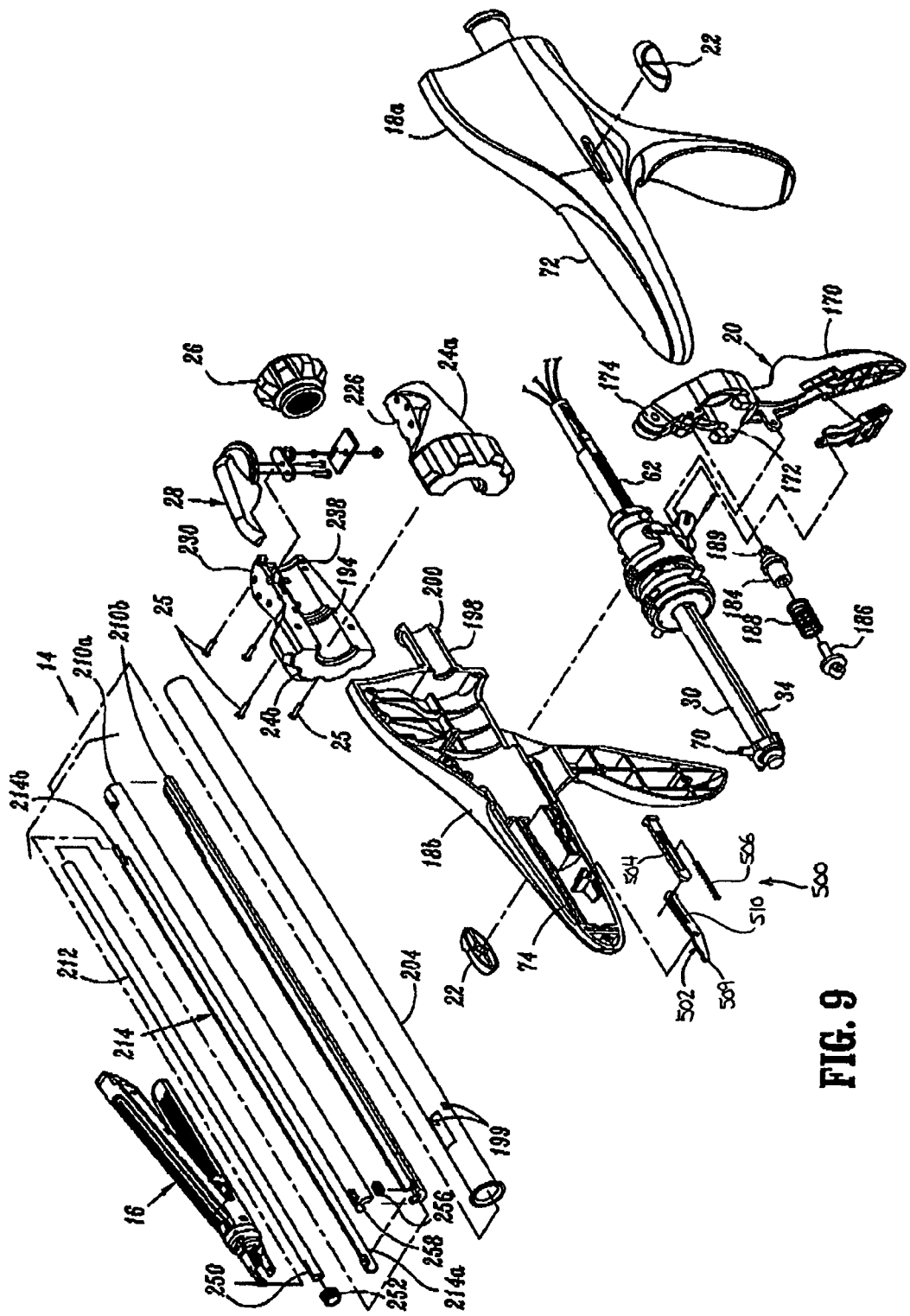
FIG. 9 is a perspective view with parts separated of the surgical stapling device shown in FIG. 1.
Figure 10:
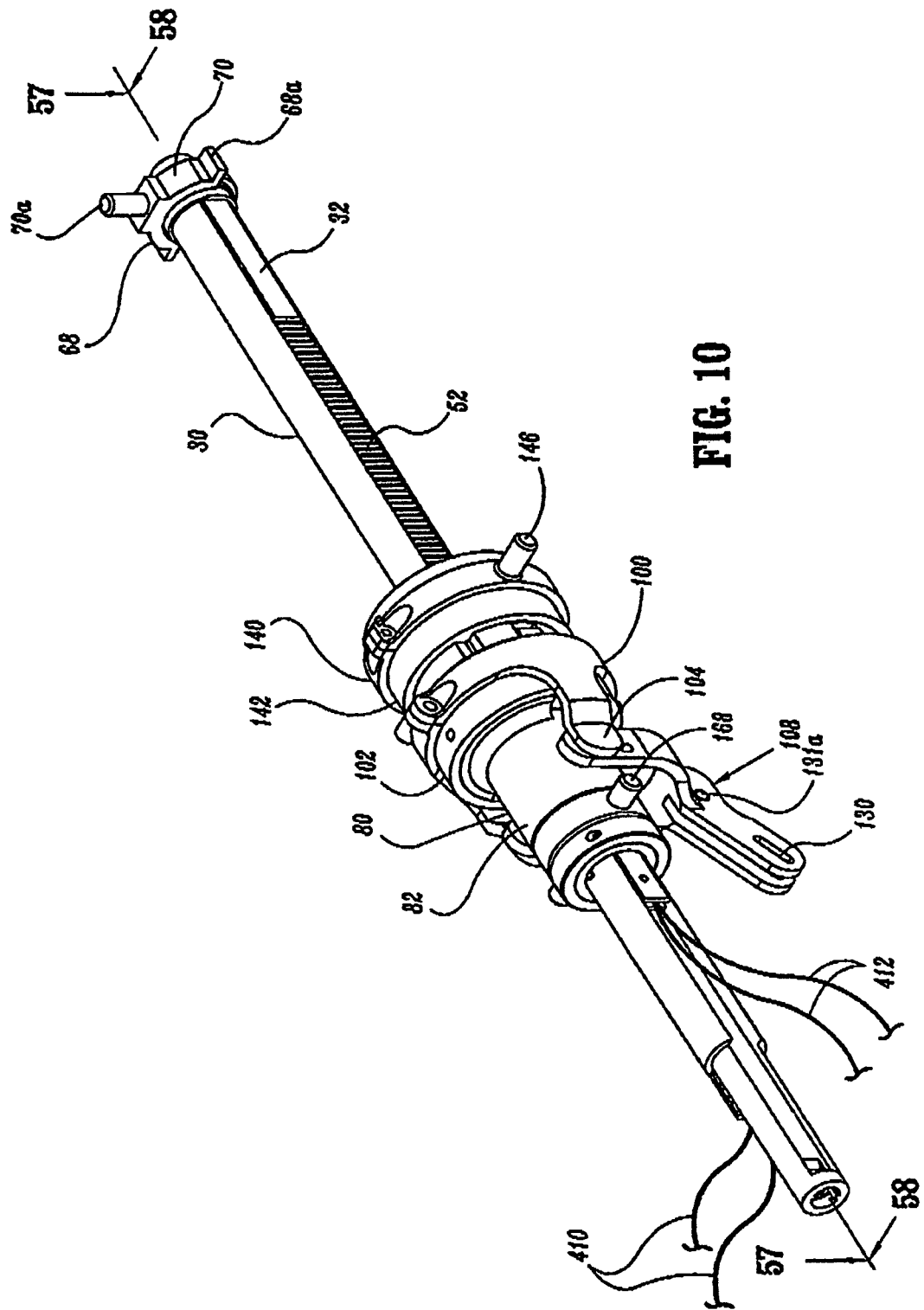
FIG. 10 is a side perspective view from the distal end of the spindle and barrel assembly of the surgical stapling device shown in FIG. 1.

Referring to FIG. 9, a biasing mechanism 182 includes a hollow cylindrical member 184, a cylindrical rod 186 telescopingly received within hollow cylindrical member 184 and a coil spring 188 positioned between cylindrical member 184 and cylindrical rod 186. Cylindrical member 184 has a first end 189 pivotally secured to firing trigger 20 about a pivot pin 190 (FIG. 4). Cylindrical rod 186 is pivotally secured between handle half-sections 18a and 18b about a pivot pin 192 (FIG. 4). Coil spring 188 is positioned between cylindrical member 184 and cylindrical rod 186 to urge member 184 and rod 186 apart and thus, urge firing trigger 20 to a non-actuated or non-compressed position.

In use, when trigger 20 is manually pivoted towards stationary handle 18 in the direction indicated by arrow "X" in FIG. 6, barrel assembly 80 is moved proximally over spindle 30 in the direction indicated by arrow "Y". If first shift ring assembly 84 is in its advanced position, i.e., positioned such that firing pawl 56 is engaged with firing rack 48, firing rack 48 is pushed proximally along guide track 32. As this occurs, pinion 42, which is engaged with firing rack 48 and retraction rack 50, will rotate and advance retraction rack 50 along guide track 34. If first shift ring assembly 84 is in its retracted position, i.e., positioned such that retraction pawl 66 is engaged with retraction rack 50, retraction rack 50 will be pushed proximally along guide track 34 as barrel assembly 80 is moved proximally by firing trigger 20 over spindle 30. As this occurs, pinion 42 is driven by movement of retraction rack 50 to advance firing rack 48 distally.

Referring to FIGS. 4-6, 9 and 55, handle assembly 12 includes a lockout mechanism 500 which includes a lever 502, a drive member 504 and a biasing member 506. Lever 502 is pivotally mounted in proximal portion of handle assembly 12 between handle half-sections 18a and 18b about a pivot member 508. A curved cam channel 510 is formed along one end of lever 502 and an abutment or stop member 509 is formed on an opposite end thereof. Drive member 504 is slidable between linear guide members 512 formed on an inner wall of handle half-sections 18a and 18b. A first end of drive member 504 is positioned adjacent barrel body portion 82. A cam member 514 formed on a second end of drive member 504 is slidably positioned in cam channel 510. A biasing member, e.g., a coil spring 506, is positioned to urge drive member 504 to a distal position.

Figure 55:
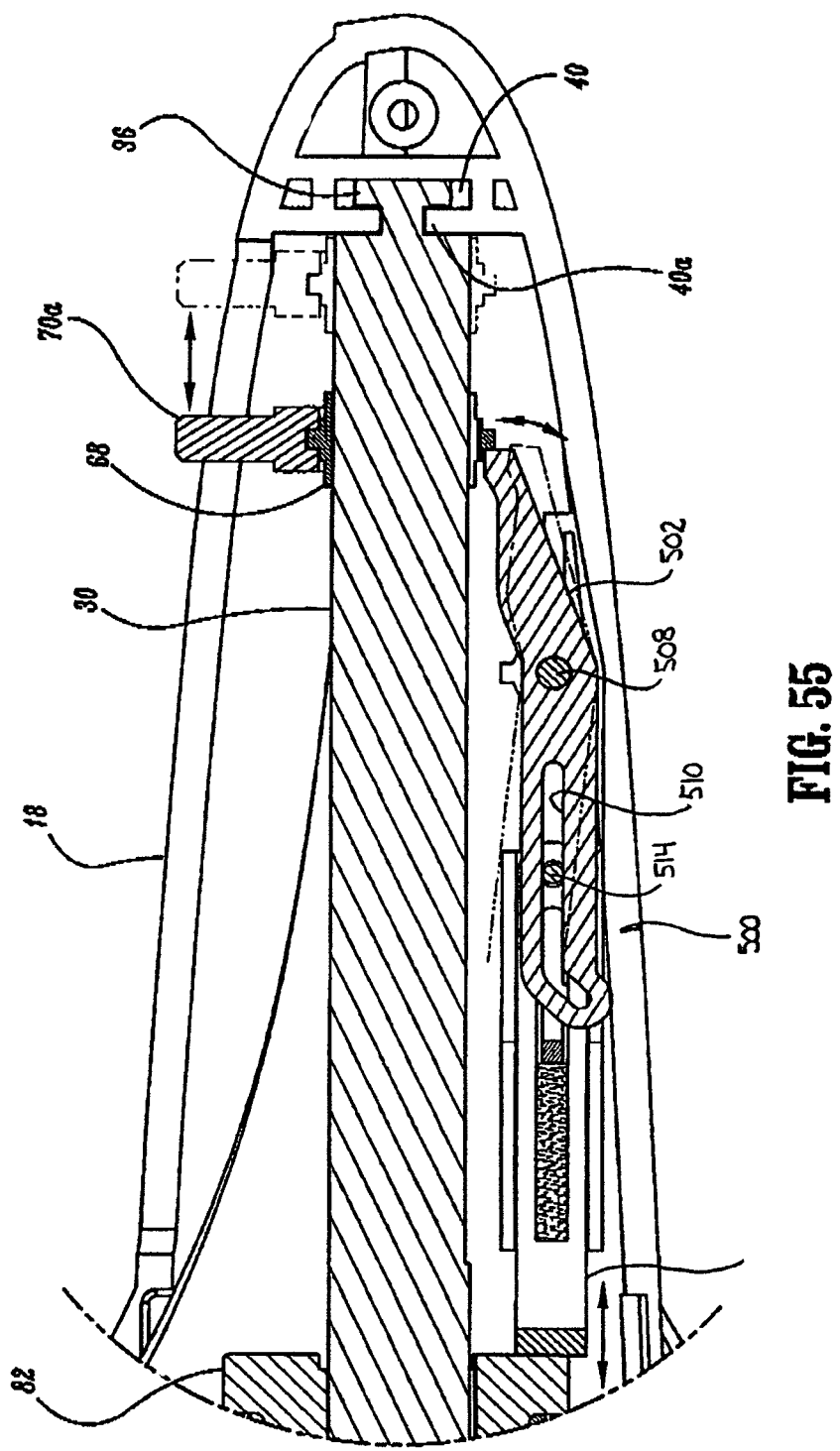
FIG. 55 is an enlarged view of the indicated area of detail shown in FIG. 51.

In use, when firing trigger 20 is compressed to drive barrel assembly 80 proximally, body portion 82 of barrel assembly 80 moves drive member 504 proximally against the bias of spring 506 to move cam member 514 through cam channel 510 of lever 502. Because drive member 504 is confined to linear movement and cam channel 510 is not linear, cam member 514 causes lever 502 to pivot about pivot member 508 such that stop member 509 is moved to a position obstructing distal movement of indicator 68 about spindle 30 (FIG. 55). When stop member 509 engages indicator 68, further compression or actuation of firing trigger 20 is prevented and firing trigger 20 must be released.

Lever 502 and cam channel 510 are positioned and configured to obstruct movement of indicator 68, and thus, prevent further actuation of the device, at a point at which tool assembly 16 has been approximated. In order to further actuate, i.e., fire, stapling device 10 after lockout mechanism 500 is engaged, firing trigger 20 must be released to return drive member 504 and lever 502 to their original positions. Since indicator 68 does not return to its original position when firing trigger 20 is released, upon further actuation of firing trigger 20, indicator 68 is able to pass by stop member 509 before it is moved to a position obstructing indicator movement.

Figure 6A:
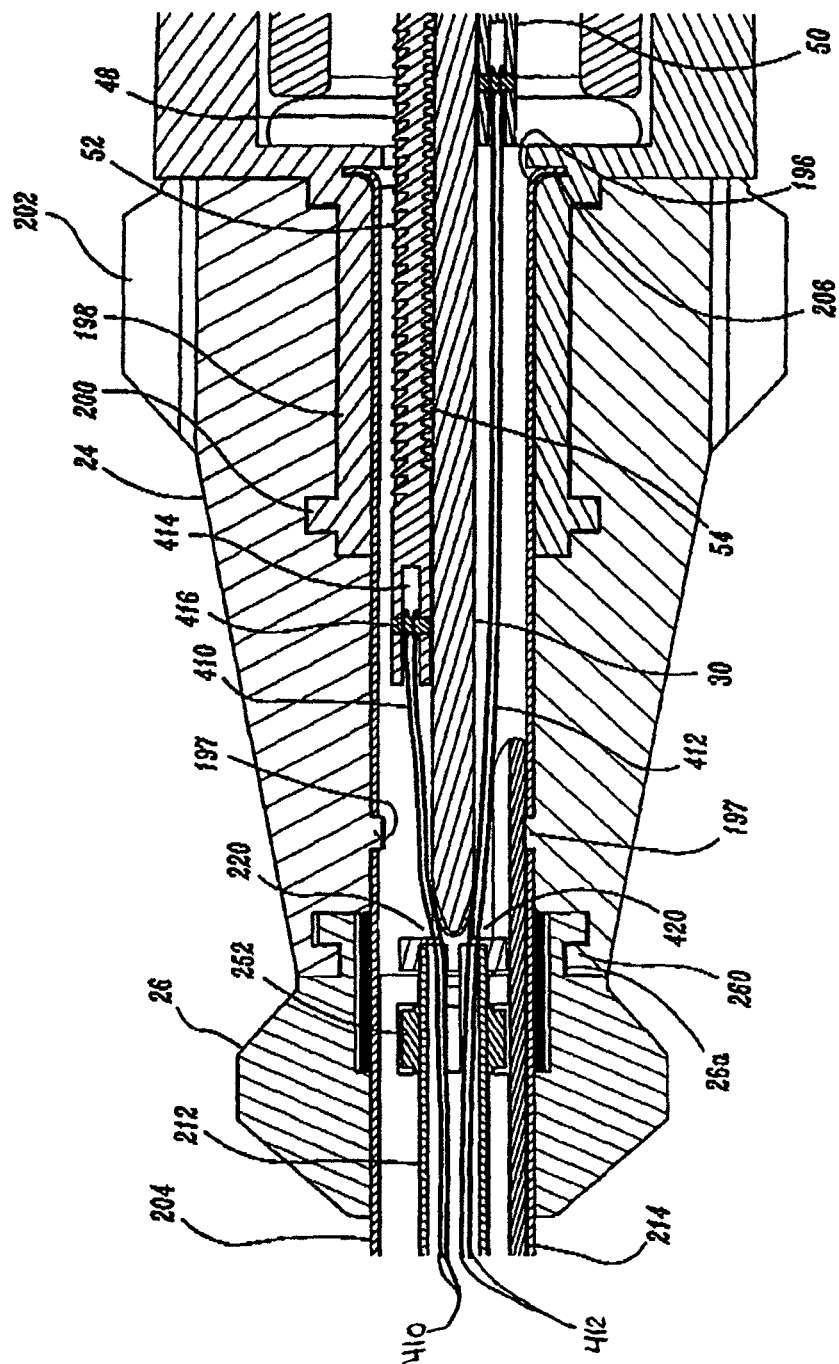
FIG. 6A is a cross-sectional view of the proximal portion of the endoscopic body portion and the distal end of the handle assembly including the tool assembly rotation knob and the body rotation knob.

Referring to FIGS. 6, 6A and 9, body rotation knob 24 can be formed from a thermoplastic material, e.g., polycarbonate, and includes half-sections 24a and 24b which together define an annular recess 194. Stationary handle portion 18, including half-sections 18a and 18b, includes a distal extension 198 having an annular flange 200. Annular flange 200 is rotatably received within annular recess 194 of body rotation knob 24 to rotatably secure and axially fix rotation knob 24 to stationary handle portion 18. A proximal portion of body rotation knob 24 includes an annular array of flutes 202 which facilitate grasping and rotation of knob 24.

The proximal end of an outer tube 204 of endoscopic body portion 14 includes an annular flange 206 which is rotatably received within an annular recess 196 formed in extension 198 of handle portion 18 (FIG. 6A). A pair of tabs 197 are formed on an inner surface of rotation knob 24 and are received in openings 199 (FIG. 9) in outer tube 204 to secure outer tube 204 to rotation knob 24. Accordingly, when body rotation knob 24 is rotated about a longitudinal axis of endoscopic body portion 14 in relation to stationary handle portion 18, rotation of outer tube 204 is also effected.

Figure 33:
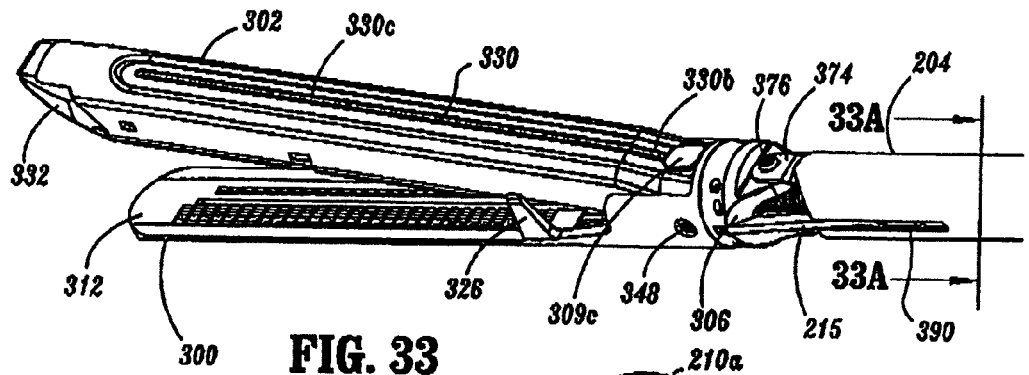
FIG. 33 is a side perspective view of the distal end of the endoscopic body portion and the tool assembly shown in FIG. 32 with the tool assembly in the non-articulated position.
Figure 33A:
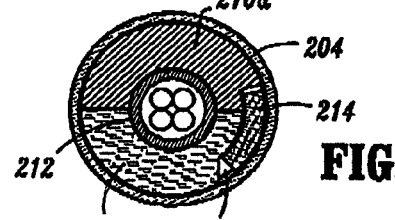
FIG. 33A is a cross-sectional view taken along section lines 33A-33A of FIG. 33.
Figure 34:
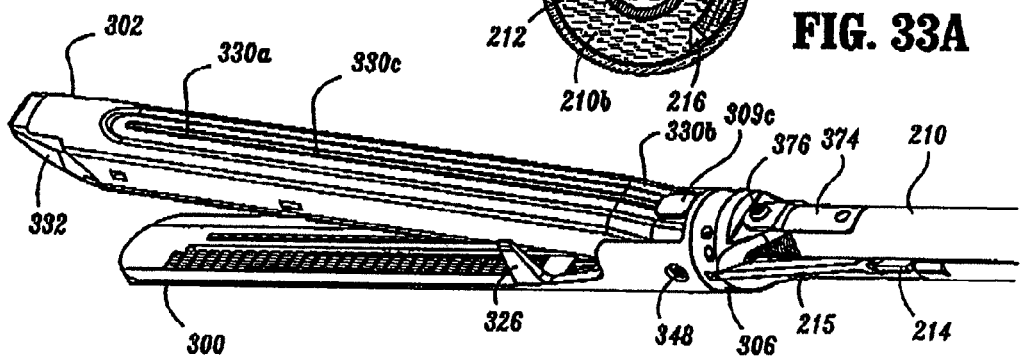
FIG. 34 is a side perspective view of the distal end of the endoscopic body portion and tool assembly shown in FIG. 33 with the outer tube removed.
Figure 35:
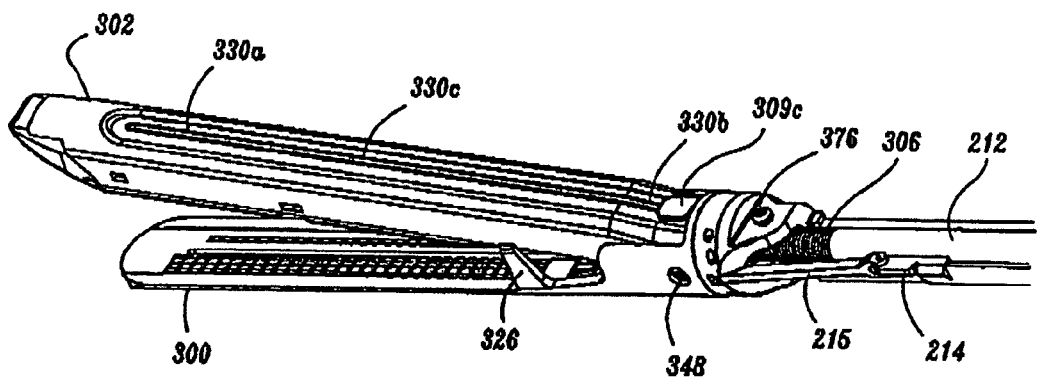
FIG. 35 is a side perspective view of the distal end of the endoscopic body portion and tool assembly shown in FIG. 34 with the spacer tube removed.

Referring to FIG. 9, endoscopic body portion 14 includes outer tube 204, a spacer tube 210 including half-sections 210a and 210b, a rotatable inner tube 212 and an arcuate articulation link 214. Articulation link 214 forms part of an articulation mechanism which will be described in detail below. Articulation link 214 has a distal end 214a connected to an articulation arm 215 (FIG. 36) and a proximal end 214b connected to other components of the articulation mechanism as will be described below. Spacer tube 210 is positioned within outer tube 204 and includes a longitudinal cutout which defines a channel 216 with outer tube 204 for slidably receiving articulation link 214 (See FIG. 33A).

Figure 23:
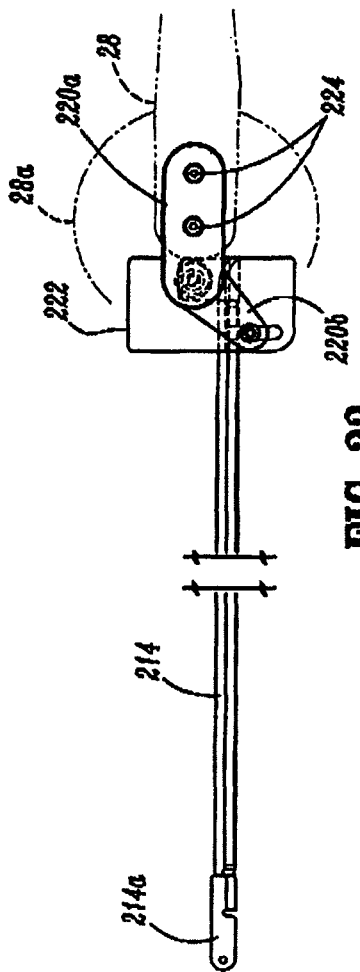
FIG. 23 is a top partial phantom view of the articulation mechanism shown in FIG. 22 in the non-articulated position.
Figure 24:
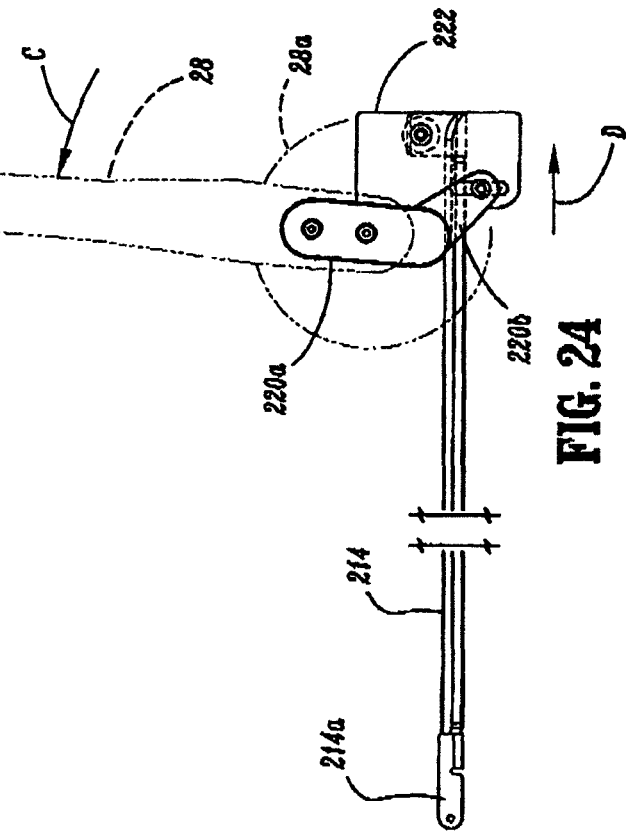
FIG. 24 is a top partial phantom view of the articulation mechanism shown in FIG. 22 in an articulated position.
Figure 22:
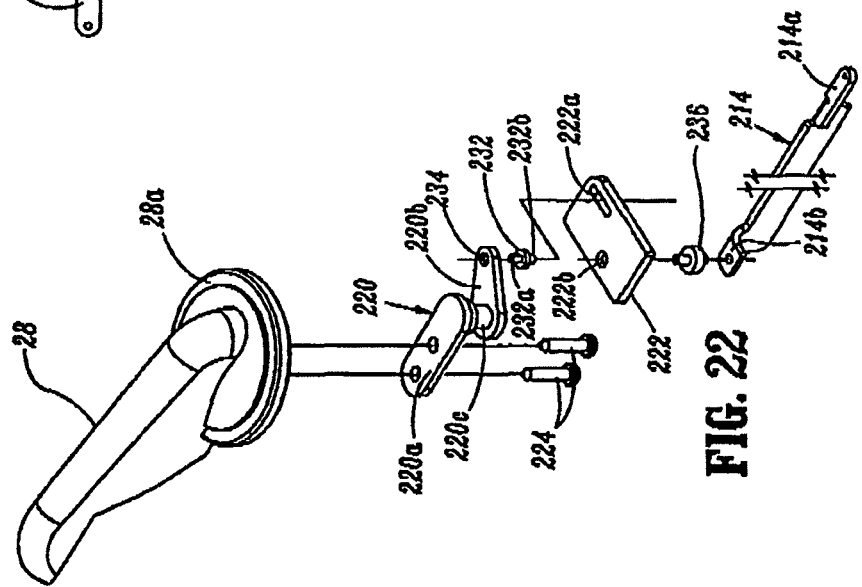
FIG. 22 is a side perspective view with parts separated of the articulation mechanism of the surgical stapling device shown in FIG. 1.

Referring to FIGS. 22-24, the articulation mechanism includes articulation lever 28, a rotatable link 220, a cam plate 222 and articulation link 214. Rotatable link 220 includes a first link member 220a, a second link member 220b and a pin or post 220c. Post 220c has a first end fixedly connected to first link member 220a and a second end fixedly connected to second link member 220b. First link member 220a is secured to a base portion 28a of lever 28 by a pair of pins 224. Post 220c extends through an opening 226 (FIG. 9) formed in body rotation knob 24 such that lever 28 and first link member 220a are rotatably positioned on a flat surface 230 of body rotation knob 24 (FIG. 9) and second link member 220b is rotatably positioned within body rotation knob 24. Second link member 220b is pivotally connected to cam plate 222 via a first connector 232. First connector 232 includes a first pin member 232a which is pivotally received within a bore 234 formed in second link member 220b and a second pin member 232b which is slidably positioned within a cam slot 222a formed in cam plate 222. A second connector 236 is rotatably connected to cam plate 222 via hole 222b and pivotally connected to the proximal end of articulation link 214b. Cam plate 222 is positioned within a recess 238 (FIG. 9) of body rotation knob 24. Recess 238 confines cam plate 222 to linear movement therein.

In use, when lever 28 is pivoted about an axis "Y" (FIG. 22) defined by post 220c of rotatable link 220 in the direction indicated by arrow "C" in FIG. 24, first and second link members 220a and 220b are pivoted about axis Y. As second link member 220b pivots, second pin member 232b of connector 232 engages a wall defining cam slot 222a of cam plate 222 to move cam plate 222 linearly in the direction indicated by arrow "D" in FIG. 24 within recess 238 of body rotation knob 24. This linear movement of cam plate 222 is translated to linear movement of articulation link 214 via second connector 236. The distal end 214a of articulation link 214 is operably connected to articulation arm 215 (FIG. 36), in a manner to be discussed in further detail below, such that linear movement of articulation link 214 effects articulation of tool assembly 16.

Figure 25:
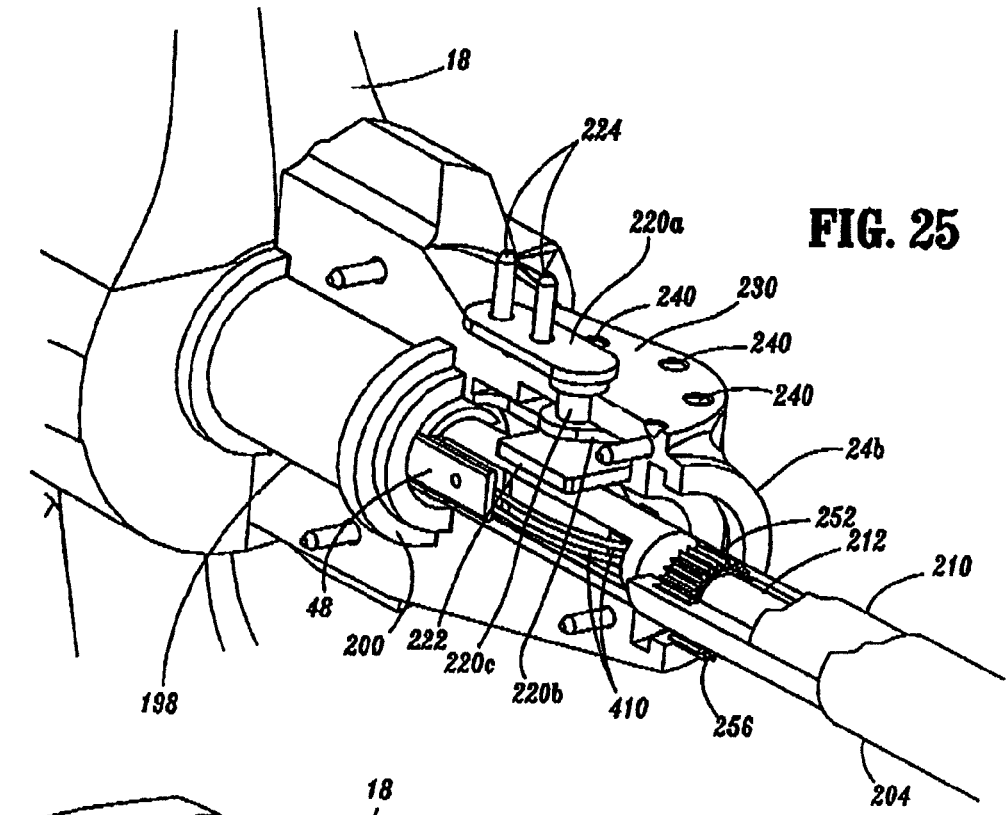
FIG. 25 is a side perspective partial cutaway view from the distal end of the proximal end of the endoscopic body portion and the distal end of the handle assembly with a half-section of the rotation knob and the articulation lever removed.
Figure 26:
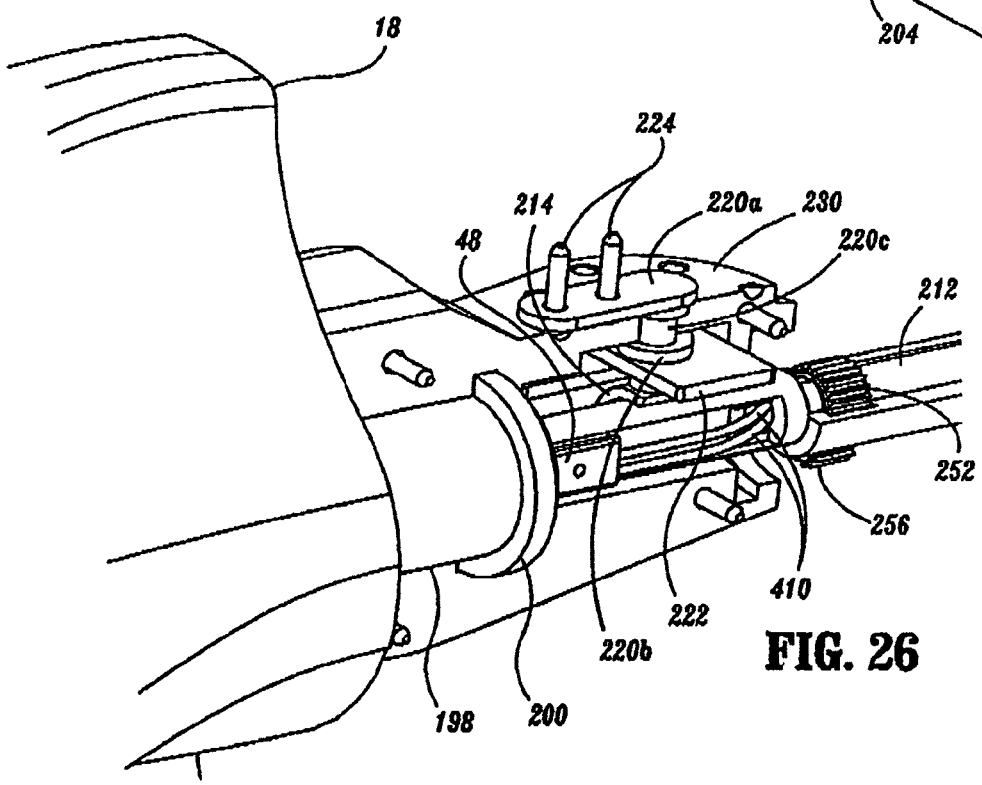
FIG. 26 is a side perspective view from the proximal end of the endoscopic body portion and the distal end of the handle assembly with the outer tube, the spacer tube and a half-section of the rotation knob and the articulation lever removed.
Figure 29:
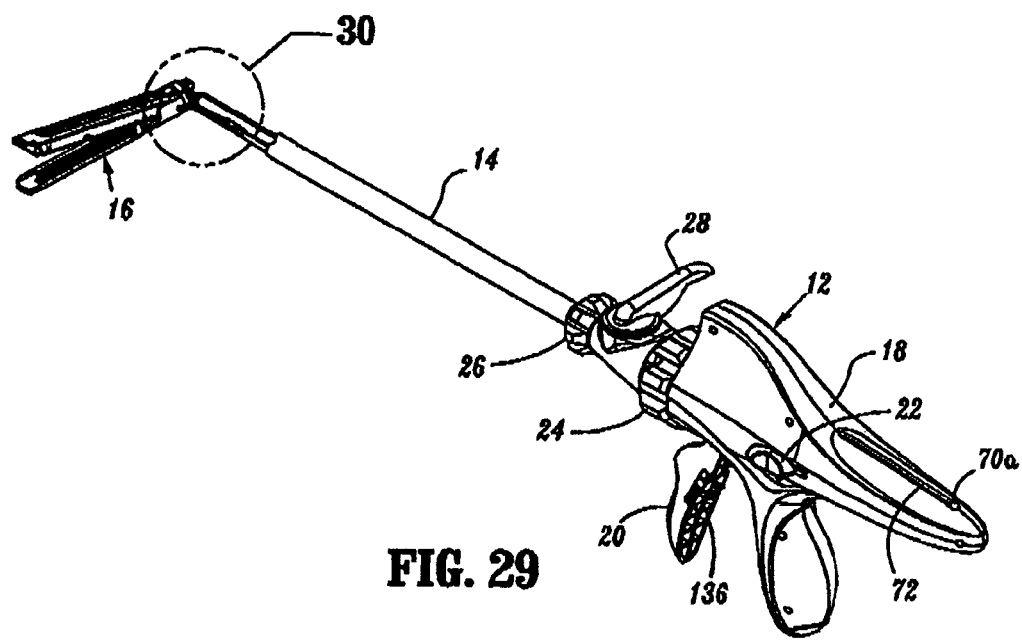
FIG. 29 is a side perspective view from the proximal end of the surgical stapling device shown in FIG. 1 with the tool assembly articulated ninety degrees and a distal portion of the outer tube of the endoscopic body portion cutaway.
Figure 30:
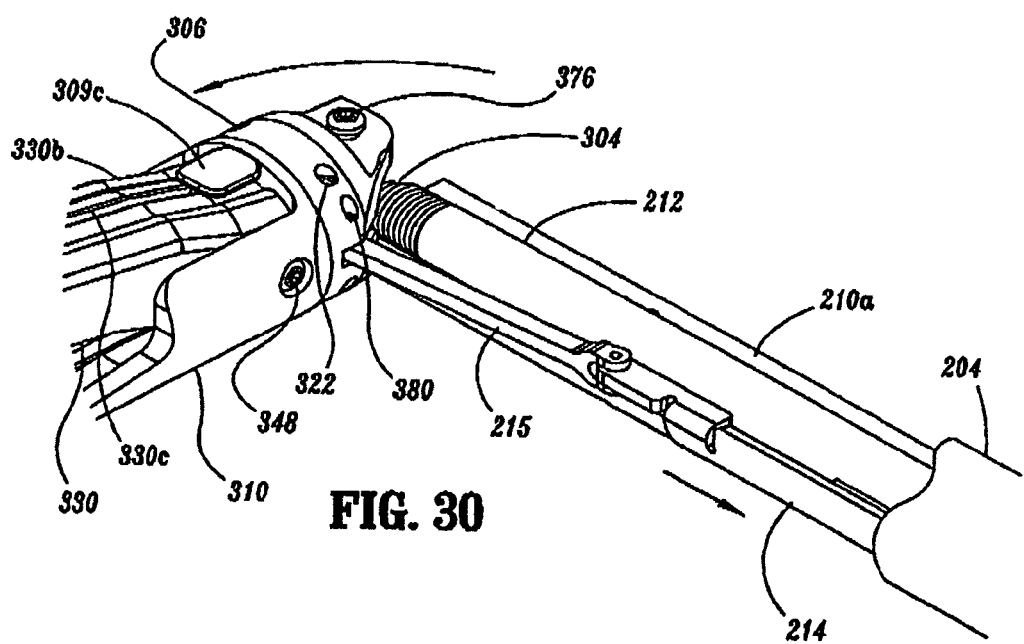
FIG. 30 is an enlarged view of the indicated area of detail shown in FIG. 29.
Figure 53:
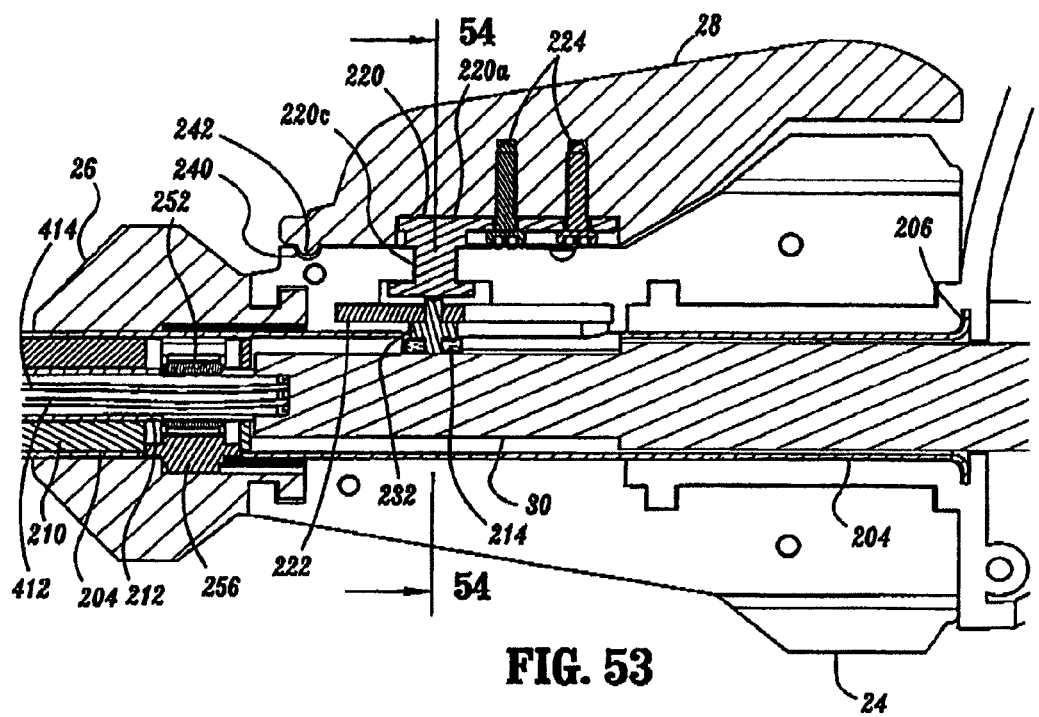
FIG. 53 is an enlarged view of the indicated area of detail shown in FIG. 51.
Figure 54:
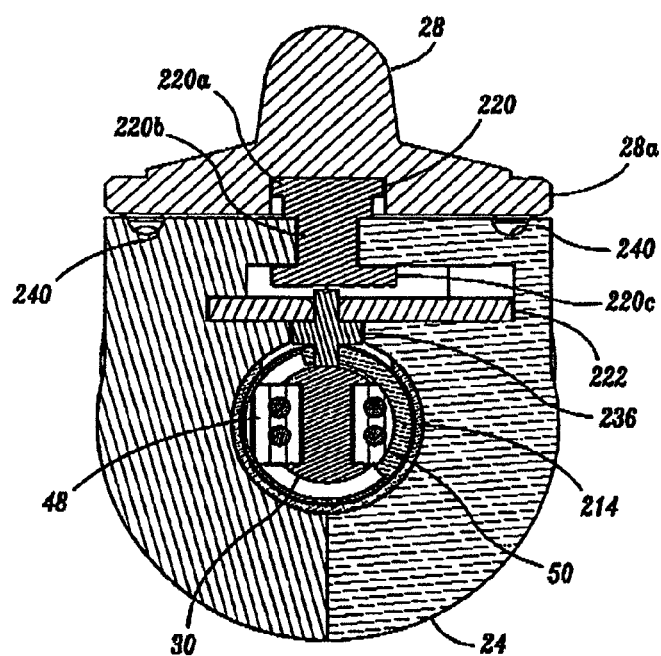
FIG. 54 is a cross-sectional view taken along section lines 54-54 of FIG. 53.

Referring to FIGS. 25 and 26, surface 230 of body rotation knob 24 can include a plurality of recesses 240 dimensioned to releasably receive an abutment 242 (FIG. 53) formed on a bottom surface of lever 28. Engagement between articulation lever abutment 242 and any one of recesses 240 retains the tool assembly at a pre-selected angle of articulation. In one embodiment, recesses 240 are provided to retain tool assembly 16 at angles of articulation of approximately 15°, 30°, 45°, 60°, 75°, and 90°. Alternately, recesses 240 may be provided to retain the tool assembly at any other desired angle(s) of articulation.

Referring to FIGS. 9 and 25-35, endoscopic body portion 14, as discussed above, includes an inner rotatable tube 212 and a spacer tube 210. A first gear 252 is non-rotatably secured to the proximal end of inner tube 212. In one embodiment, the proximal end of inner tube 212 has at least one slot 250 formed therein, and gear 252 has an inner rib 254 (FIG. 31) which is received within slot 250 to rotatably fix gear 252 to inner tube 212. Alternately, gear 252 may be secured to inner tube using other known fastening techniques, e.g., set screws, welding, brazing, crimping, etc. A second gear 256 is rotatably supported on half-section 210a of spacer tube 210 adjacent an opening 258 formed in spacer tube 210. Gear 256 extends through opening 258 and meshes with gear 252.

Figure 31:
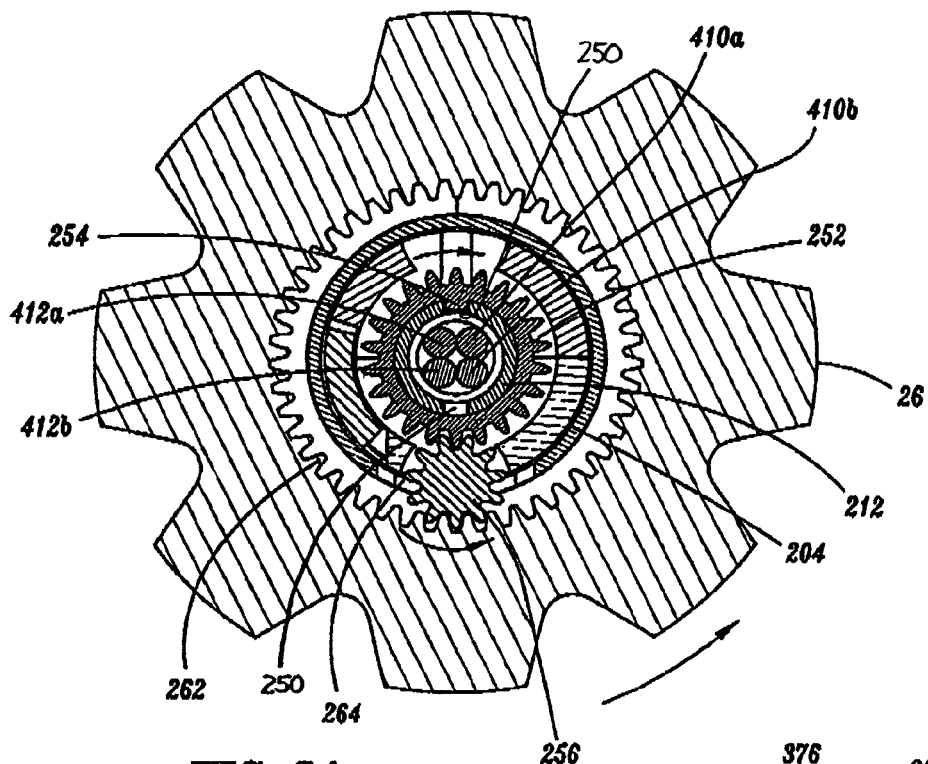
FIG. 31 is a cross-sectional view taken along section lines 31-31 of FIG. 6.
Figure 32:
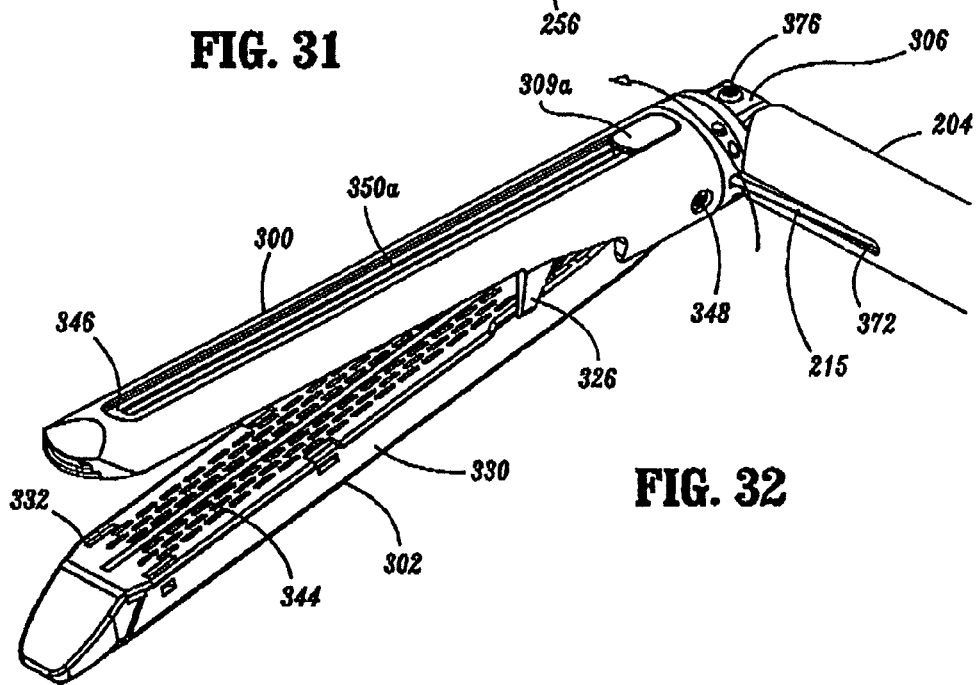
FIG. 32 is a side perspective view from the distal end of the distal end of the endoscopic body portion and the tool assembly of the surgical stapling device shown in FIG. 1 with the tool assembly articulated ninety degrees.

Referring also to FIGS. 6A and 31, tool assembly rotation knob 26 includes an annular channel 26a which is dimensioned to receive an annular rib 260 formed on body rotation knob 24 to rotatably secure knob 26 to knob 24 about outer tube 204. The internal surface of tool assembly rotation knob 26 includes gear teeth 262 which also mesh with gear 256 through an opening 264 in outer tube 204 (FIG. 31). As such, when tool assembly rotation knob 26 is rotated about outer tube 204 in relation to body rotation knob 24, gears 256 and 252 are driven or rotated. Since inner tube 212 is rotatably fixed to gear 252, inner tube 212 rotates with gear 252. The distal end of inner tube 212 is operably connected to tool assembly 16 in a manner to be discussed below such that rotation of inner tube 212 is translated into rotation of tool assembly 16.

Figure 45:
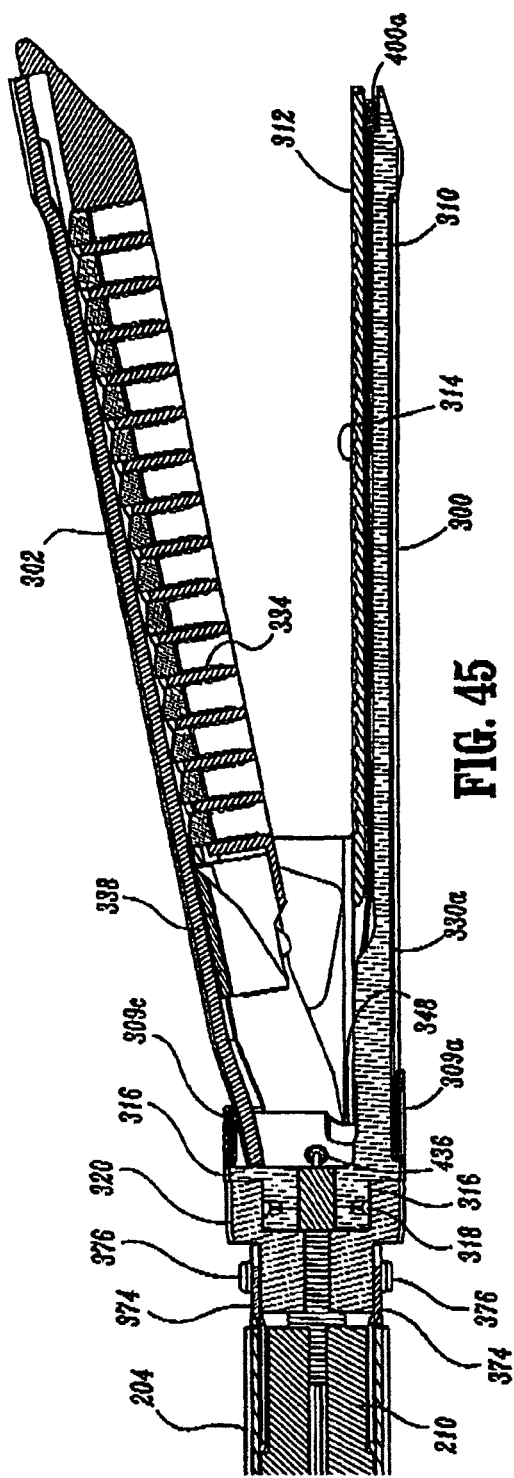
FIG. 45 is a side cross-sectional view of the distal end of the endoscopic body portion and tool assembly shown in FIG. 43 through a leg of one row of staples.

Referring to FIGS. 36-48, tool assembly 16 includes an anvil assembly 300, a cartridge assembly 302, a torque transmitting member 304, a rotation collar 306, a drive member 308 and a dynamic clamping or actuation member 309. Anvil assembly 300 includes a body portion 310 and an anvil plate 312 having a plurality of staple forming depressions 314 (FIG. 45). The proximal end of anvil body portion 310 includes a cylindrical extension 316 having an annular groove or channel 318 formed therein. Rotation collar 306 defines a cylindrical bore 320 (FIG. 36) for receiving cylindrical extension 316 of anvil body portion 310. A pair of pins 322 extend through holes 324 in rotation collar 306 and into annular channel 318 of cylindrical extension 316 of anvil body portion 310 to rotatably secure anvil body portion 310 to rotation collar 306. Anvil body portion 310 also includes a pair of spaced tissue stops 326.

Cartridge assembly 302 includes a channel support member 330, a staple cartridge 332, a plurality of staples 334, a plurality of pushers 336 associated with staples 334 and a drive sled 338. Staple cartridge 332 is supported within channel support member 330 and can include a plurality of linear rows of staple receiving pockets 340. In one embodiment, staple cartridge 332 includes six linear rows of staple receiving pockets 340 although other staple pocket configurations and patterns are envisioned. Each staple receiving pocket 340 slidably receives a staple 334 and a pusher 336 or a portion of a pusher 336. Staple cartridge 332 includes channels 342 for facilitating translation of sled 338 through staple cartridge 332. Sled 338 includes cam surfaces 338a for engaging pushers 336 and driving staples 334 from staple cartridge 332. Staple cartridge 332 also includes a central longitudinal slot 344 for allowing translation of dynamic clamping member 309 through staple cartridge 332. Sled 338 is positioned distally of clamping member 309 and is engaged and driven by clamping member 309 after the anvil and cartridge assemblies have been approximated.

Dynamic clamping member 309 includes an upper flange portion 309a, a central body portion 309b and a lower flange portion 309c. Upper flange portion 309a is positioned to slide along an upper surface of anvil body portion 310. In one embodiment, an elongated recess 346 is provided in anvil body portion 310 to accommodate upper flange portion 309a. A knife blade 348 formed in, or supported by central body portion 309b is positioned between upper and lower flange portions 309a and 309c. An elongated slot 350a is formed in anvil plate 312 to facilitate passage of dynamic clamping member 309 through anvil assembly 300. Lower flange portion 309c is positioned to translate or slide along a bottom surface 330a (FIG. 45) of channel support member 330 of cartridge assembly 302. By engaging surfaces of both the anvil assembly 300 and cartridge assembly 302, dynamic clamping member 309 limits deflection and/or bowing of the anvil and cartridge assemblies and defines a maximum tissue gap of tool assembly 16.

Figure 36:
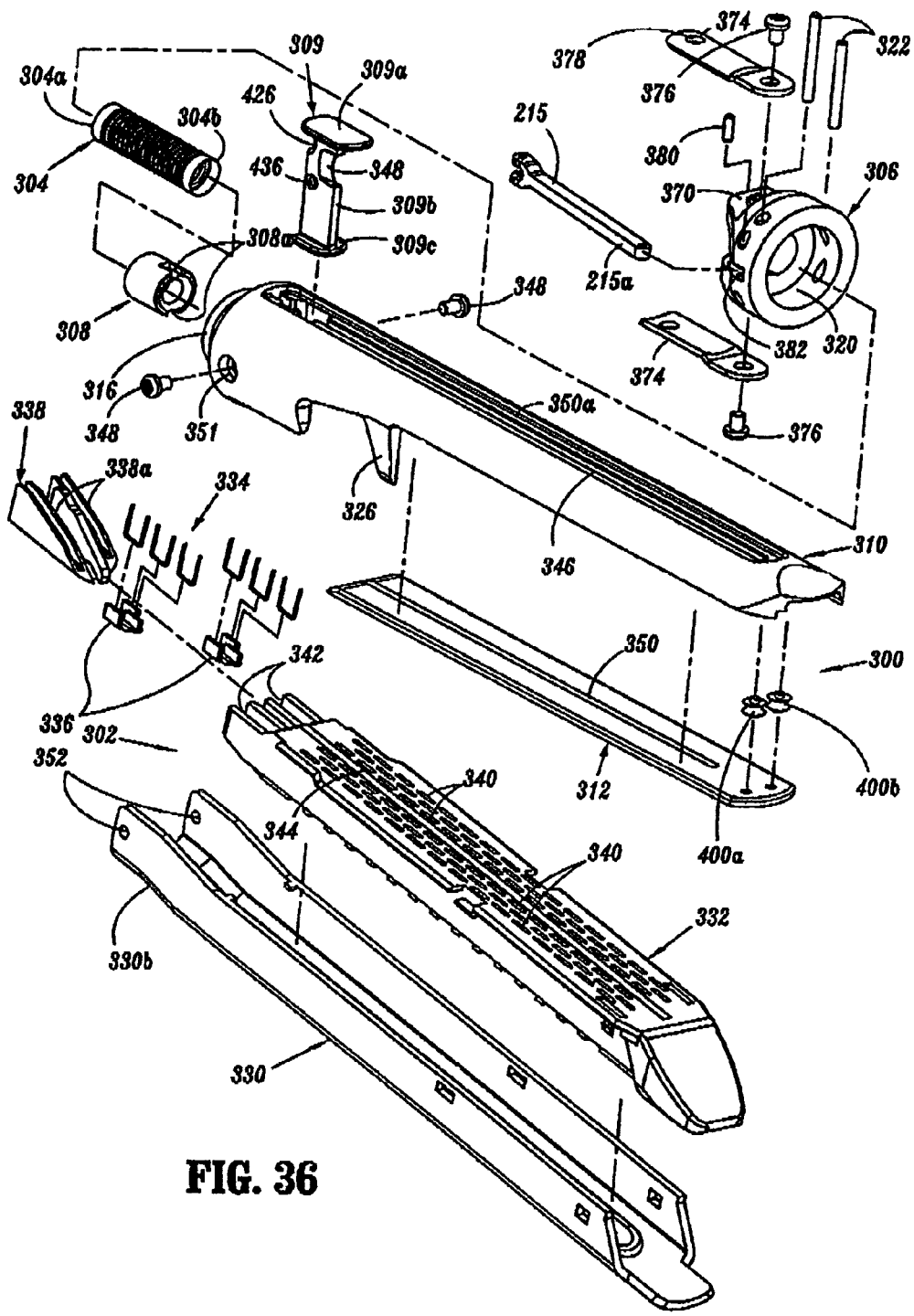
FIG. 36 is a side perspective view from the distal end with parts separated of the tool assembly and rotation collar of the surgical stapling device shown in FIG. 1.
Figure 46:
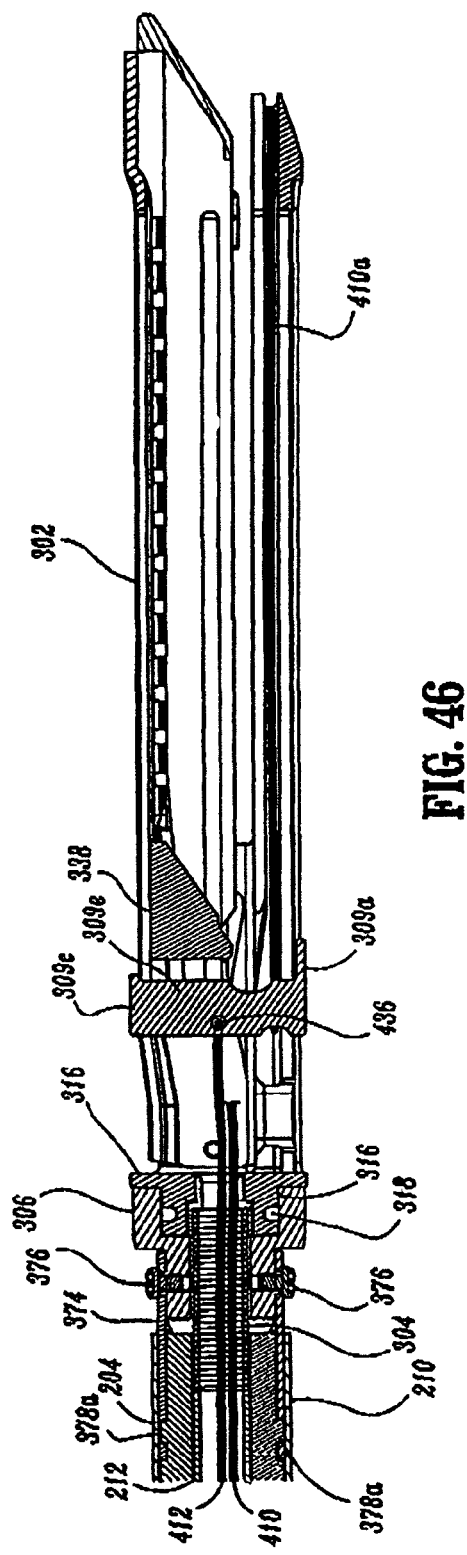
FIG. 46 is a side cross-sectional view of the distal end of the endoscopic body portion and tool assembly shown in FIG. 45 through the dynamic clamping member.
Figures 51, 52:
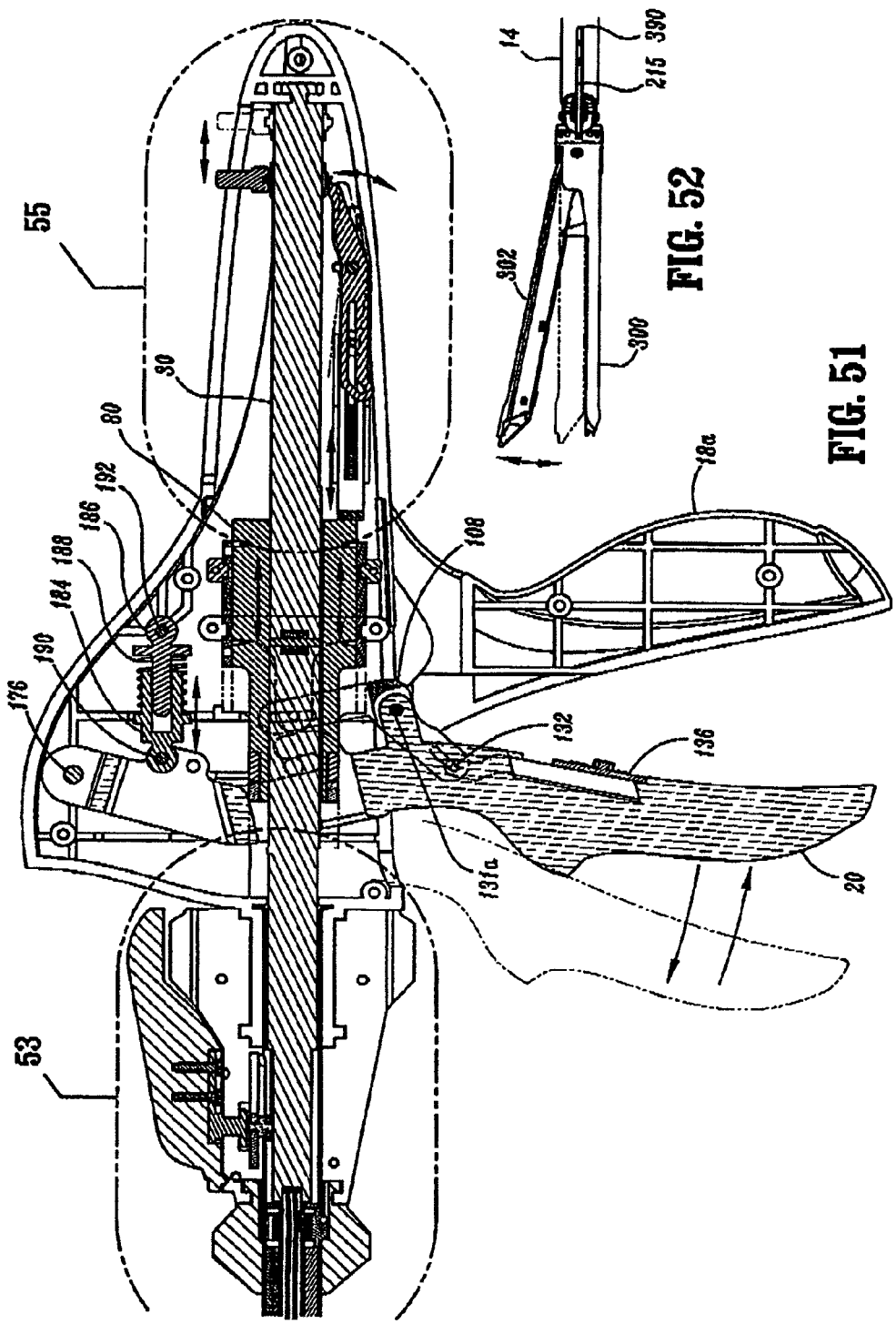
FIG. 51 is a cross-sectional view of the handle assembly and proximal portion of the endoscopic body portion shown in FIG. 49 with the firing trigger actuated in the grasper mode.
FIG. 52 is a side view of the distal end of the surgical stapling device shown in FIG. 1 with the tool assembly shown in the open position and in phantom in the closed position.

Referring to FIG. 36, cartridge assembly 302 is pivotally secured to anvil assembly 300 by pivot pins 348. Pivot pins 348 extend through openings 350 formed in anvil body portion 310 and into openings 352 formed in channel support member 330. Cartridge assembly 302 is pivotal in relation to anvil assembly 300 from an open position spaced from anvil assembly 300 (FIG. 45) to an approximated position in juxtaposed alignment with anvil assembly 300 (FIG. 46).

Referring to FIGS. 40-46, torque transmitting member 304 includes a hollow flexible member. In one embodiment, torque transmitting member 304 includes a bellows which is constructed from a flexible material capable of transmitting torque, e.g., stainless steel, Nitinol™, nickel, etc. Alternately, torque transmitting member 304 may be formed of other materials including plastics. As shown in FIGS. 27 and 28, torque transmitting member 304 may also comprise a coil spring or the like. The proximal end 304a of torque member 304 is fixedly secured to the distal end of inner tube 212 such as by welding or brazing. The distal end of torque transmitting member 304 is secured to drive member 308. Drive member 308 is positioned within a bore 360 (FIG. 37) of cylindrical extension 316 of anvil body portion 310. Drive member 308 includes a pair of cutouts 308a which engage tabs 360a formed along a wall defining bore 360. Engagement between tabs 360a and cutouts 308a rotatably fixes drive member 308 to anvil body portion 310.

In operation, when inner tube 212 is rotated by rotating tool assembly rotation knob 26 in the manner discussed above, torque transmitting member 304 is rotated to effect rotation of anvil body portion 310. Since anvil body portion 310 is rotatably mounted on rotation collar 306 and cartridge assembly 302 is pivotally supported on anvil body portion 310, rotation of anvil body portion 310 effects rotation of the entire tool assembly 316 independently of endoscopic body portion 14.

Referring to FIGS. 27-30 and 36, the proximal portion of rotation collar 306 includes a clevis 370 having screw holes 372. A pair of bracket members 374 are secured at one end to clevis 370 by pivot members 376 which allow collar 306, and thus, tool assembly 16, to pivot or articulate thereabout. The other end of each bracket member 374 includes an opening 378 which receives a projection 378a formed on spacer tube 210 (FIG. 43) to secure collar 306 and tool assembly 16 to the distal end of endoscopic body portion 14. Outer tube 204 is positioned about spacer tube 210 and bracket members 374 to prevent separation of the parts. Articulation arm 215 has a distal end 215a which is pivotally connected to rotation collar 306 by a pivot member or pin 380 at a pivot location 382 offset from the pivot axis defined by pivot members 376, i.e., the pivot axis of tool assembly 16. The proximal end 215b of articulation arm 215 is pivotally secured to articulation link 214 by a pivot pin 384.

In use, when articulation lever 28 is pivoted to move articulation link 214 linearly within outer tube 204 in the manner discussed above, articulation arm 215 is also moved, i.e., advanced or retracted. Since the distal end of articulation arm 215 is pivotally connected to rotation collar 306 at a position offset from pivot member 376, movement of articulation arm 215 effects articulation of rotation collar 306 and tool assembly 16 about the pivot axis defined by pivot member 376 (FIG. 28). A slot 390 is provided in the distal end of outer tube 304 to accommodate movement of articulation arm 215. Using this articulation mechanism, tool assembly 16 is pivotal to an angle of about 90° in relation to the longitudinal axis of the endoscopic body portion 14 of the device.

As illustrated in FIG. 28, torque transmitting member 304 is flexible such that it will bend about the pivot axis of tool assembly 16. In its bent condition, torque transmitting member 304 is still able to translate rotation of inner tube 212 to rotation of tool assembly 16.

Referring to FIG. 36, a pair of rollers 400a and 400b are secured within the anvil assembly 300 between anvil body portion 310 and anvil plate 312. Rollers 400a and 400b include a central pivot member which is rotatably received in openings 402 formed in anvil plate 312 and similar openings (not shown) formed in anvil body portion 310. Rollers 400 form turnabouts for a cable drive system for approximating the anvil and cartridge assemblies 300 and 302, respectively, and for ejecting staples from staple cartridge 332. In addition to rollers, fixed pins guideways, or the like can be employed.

Referring to FIGS. 6A and 43-48, the cable drive system of the presently disclosed stapling device 10 includes a firing cable 410 and a retraction cable 412. Firing cable 410 includes a first end 410a and a second end 410b. Each end of firing cable 410a and 410b includes a loop which is secured within a slot 414 formed in the distal end of firing rack 48 by a pin 416 (FIG. 6A). Each end of firing cable 410 extends distally from firing rack 48 through an opening 420 formed in the distal end of spindle 30 into and through inner tube 212. Referring to FIG. 48, ends 410a and 410b of firing cable 410 extend from inner tube 212, through torque transmitting member 304, drive member 308, rotation collar 306 and into anvil assembly 300. Ends 410a and 410b extend distally through spaced channels defined between anvil plate 312 and anvil body portion 310 along opposite sides of anvil assembly 300, around rollers 400a and 400b, respectively, proximally through a center channel 424 defined between anvil plate 312 and anvil body portion 310, and around dynamic clamping member 309 (FIG. 38). Dynamic clamping member 309 includes a rounded surface 426 to prevent wearing of cable 410.

In use, when firing trigger 20 is compressed towards stationary handle 18 and firing pawl 56 is engaged with firing rack 48, firing rack 48 is moved proximally in the manner discussed above. As firing rack 48 moves proximally, both ends of firing cable 410 are pulled proximally to advance dynamic clamping member 309 distally in relation to anvil and cartridge assemblies 300 and 302 to approximate the anvil and cartridge assemblies 300 and 302. Sled 338 is positioned distally of dynamic clamping member 309 and is driven through staple cartridge 332 by dynamic clamping member 309 to sequentially eject staples 334 from staple cartridge 332.

Retraction cable 412 also includes a first end 412a and a second end 412b. Each end 412a and 412b includes a loop which is secured within a slot 432 formed in the distal end of retraction rack 50 by a pin 434 (FIG. 6A). Each end of retraction cable 412 extends distally from retraction rack 50 through opening 420 in spindle 30 into and through inner tube 212. Ends 412a and 412b of retraction cable 412 extend from inner tube 212, through torque transmitting member 304, drive member 308, rotation collar 306 and cylindrical portion 316 of anvil body portion 310 to dynamic clamping member 309. A hole 436 is formed through central body 309b of dynamic clamping member 309. Cable 412 extends through hole 436 to secure cable 412 to dynamic clamping member 309 (FIG. 38).

In use, when firing trigger 20 is compressed towards stationary handle 18 and retraction pawl 66 is engaged with retraction rack 50, retraction rack 50 is moved proximally in the manner discussed above. As retraction rack 50 moves proximally, both ends of retraction cable 412 are pulled proximally to pull cable 412 and dynamic clamping member 309 proximally in relation to anvil and cartridge assemblies 300 and 302, respectively. Movement of dynamic clamping member 309 proximally allows the anvil and cartridge assemblies to move to the spaced position.

Operation of surgical stapling device 10 will now be described with reference to FIGS. 49-71. FIGS. 49-55 illustrate surgical stapling device 10 in the grasper mode. In the grasper mode, firing trigger 20 can be actuated or compressed towards stationary handle portion 18 to approximate anvil and cartridge assemblies 300 and 302. Device 10 will not fire in the grasper mode. To place stapling device 10 in the grasper mode, grasper button(s) 22 are pushed forward along stationary housing 18 in the direction indicated by arrow "E" in FIGS. 49 and 50 to move inner ring 142 of the second shift ring assembly to its advanced position. As inner ring 142 is advanced, cam member 154 moves within cam slot 60a to pivot grasper pawl 60 in the direction indicated by arrow "F" in FIG. 50 to position engagement finger 60b of grasper pawl 60 into cutout 58 of firing rack 48. This prevents device 10 from firing. When inner ring 142 of the second shift ring assembly is advanced, inner ring 142 abuts inner ring 102 of the first shift ring assembly (if the first shift ring assembly is in the retracted position) to move the first shift ring assembly including inner ring 102 to its advanced position. As discussed above, when inner ring 102 is moved to its advanced position, cam member 120 is moved within cam slot 56a of firing pawl 56 to a position which permits O-ring 98a to urge firing pawl teeth 56b into engagement with teeth 52 of firing rack 48.

When firing trigger 20 is compressed in the grasper mode, barrel assembly 80 is moved proximally about spindle 30 to move firing rack 48 proximally within guide track 32 of spindle 30. As firing rack 48 is moved proximally, firing cable 410 is pulled proximally to partially advance dynamic clamping member 309 distally in relation to anvil and cartridge assemblies 300 and 302 to approximate anvil and cartridge assemblies 300 and 302. When firing trigger 20 is released, spring 188 urges firing trigger 20 to its non-compressed position to return barrel assembly 80 to its advanced or distal-most position. Because grasper pawl finger 60b is engaged in cutout 58 of firing rack 48, firing rack 48 is moved distally with barrel assembly 82 to move dynamic clamping member 309 proximally and return anvil and cartridge assemblies 300 and 302 to the spaced position. Accordingly, firing trigger 20 can be repeatedly compressed and released to repeatedly move the anvil and cartridge assemblies between their spaced and approximated positions. The grasper made permits a surgeon to operate tool assembly as a grasper to facilitate the manipulation of tissue prior to operation of stapling device 10.

Figure 56:
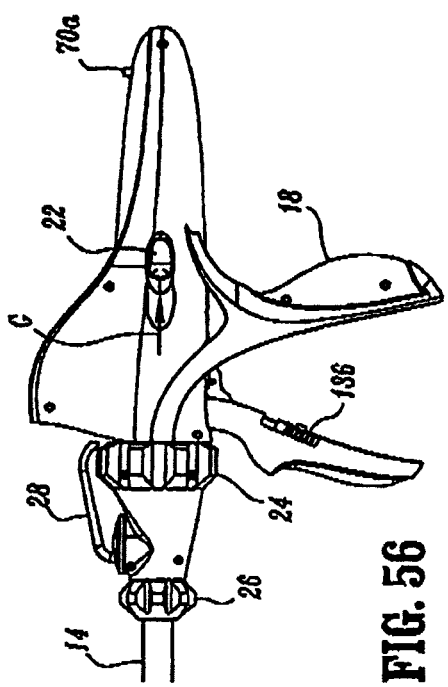
FIG. 56 is a side view of the handle assembly and proximal portion of the endoscopic body portion of the surgical stapling device with the grasper button moved to the retracted position.
Figure 57:
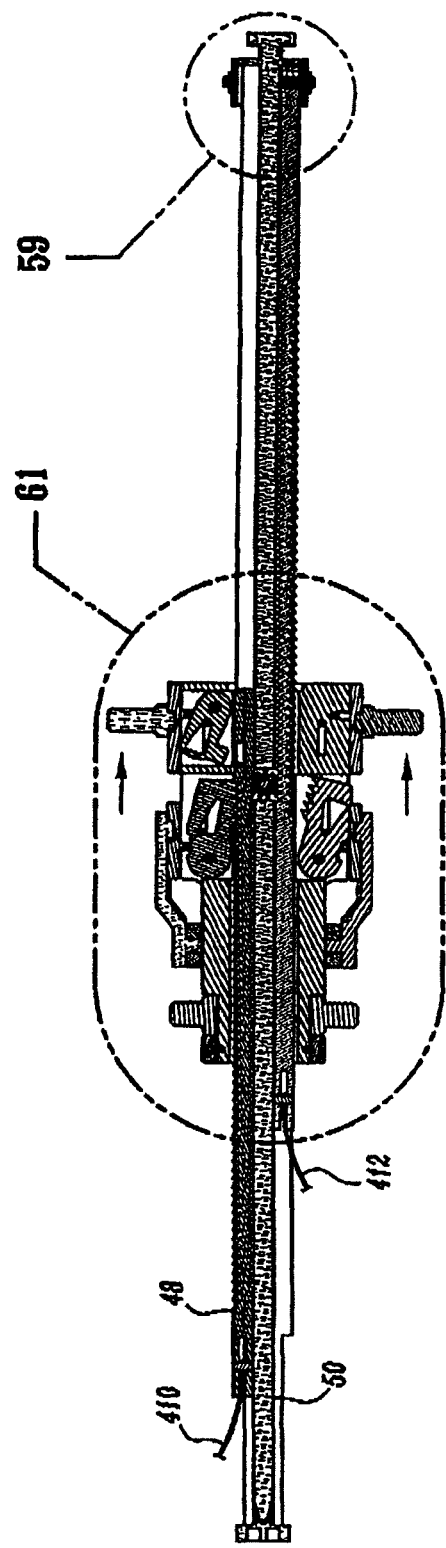
FIG. 57 is a side cross-sectional view of the spindle and barrel assembly shown in FIG. 50 with the first shift ring assembly in the advanced position.

Referring to FIGS. 56-67, stapling device 10 is put in the firing mode by manually moving grasper buttons 22 proximally, in the direction indicated by arrow "G" in FIG. 56, along stationary handle portion 18. When grasper buttons 22 are moved proximally, inner ring 142 of the second shift ring assembly is moved proximally about barrel assembly 80 to cam grasper pawl 60 out of engagement with cutout 58 in firing rack 48 (FIG. 57). Prior to actuating firing trigger 20, indicator ring 68 and extension 70, which are attached to retraction rack 50 are in the proximal-most position on spindle 30 (FIG. 58). Also, the first shift ring assembly, including inner ring 102, is retained in its advanced position by engagement between nub 81 formed on body portion 82 of barrel assembly 80 and recess 81a formed in inner ring 102.

When firing trigger 20 is actuated, barrel assembly 80 is moved proximally over spindle 30. Since firing pawl 56 is engaged with firing rack 48, firing rack 48 is also moved proximally along spindle guide track 32. As firing rack 48 is moved proximally, pinion 30, which is engaged with teeth 54 of firing rack 48 and teeth 64 of retraction rack 50, drives retraction rack 50 distally within spindle guide track 34. As firing rack 48 is moved proximally, firing cable 410 is moved proximally to pull dynamic clamping member 309 distally in relation to anvil and cartridge assemblies 300 and 302. Each actuation stroke of firing trigger 20 advances dynamic clamping member 309 a predetermined amount, e.g., 15 mm. Accordingly, multiple actuation strokes of firing trigger 20 may be required to advance dynamic clamping member 309 a distance sufficient to approximate the anvil and cartridge assemblies and to sequentially eject all of staples 334 from staple cartridge 332.

Figure 64:
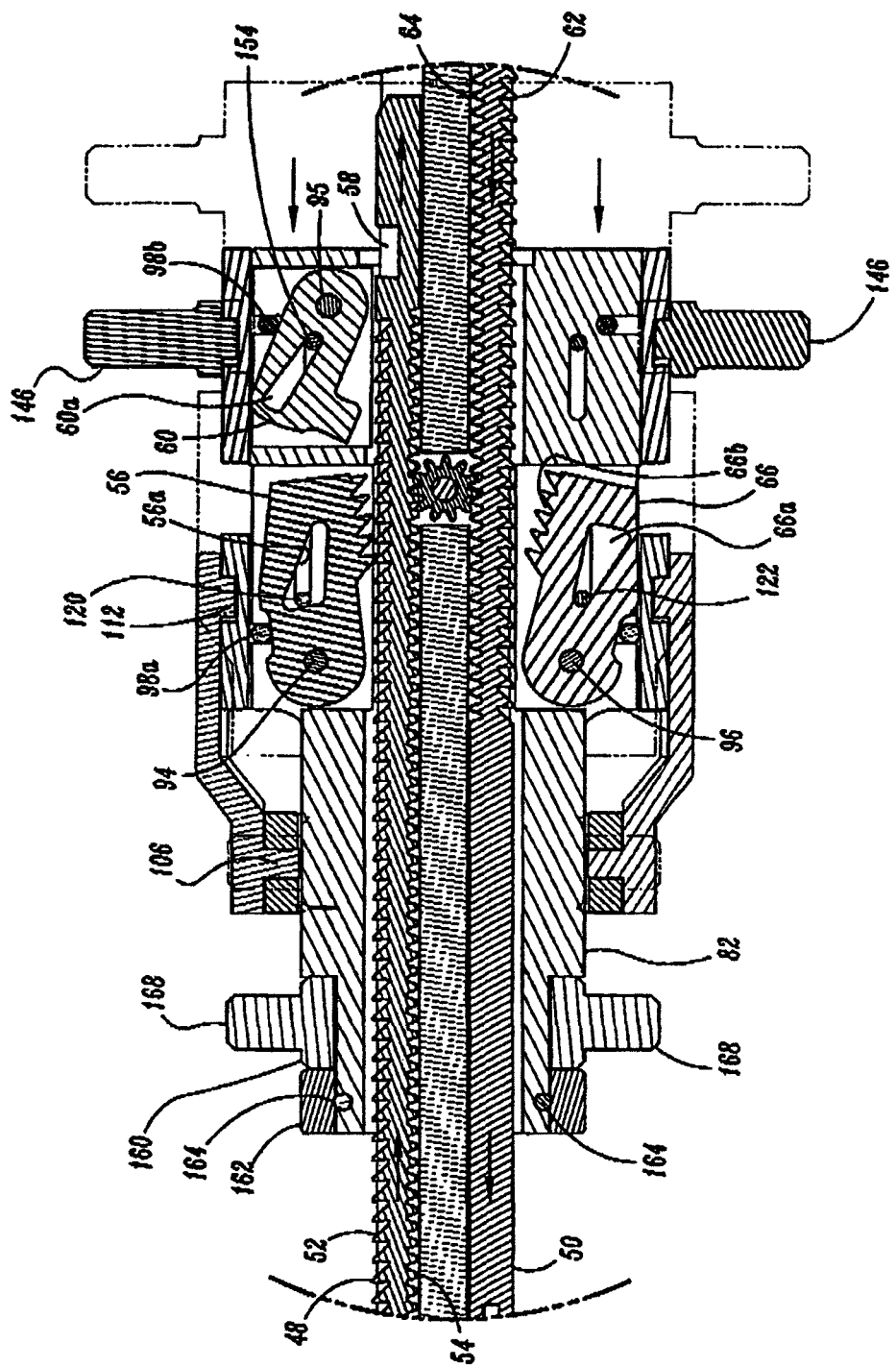
FIG. 64 is a side cross-sectional view of the spindle and barrel assembly shown in FIG. 61 during movement of the firing trigger to the non-compressed position and movement of the barrel assembly distally about the spindle.
Figure 65:
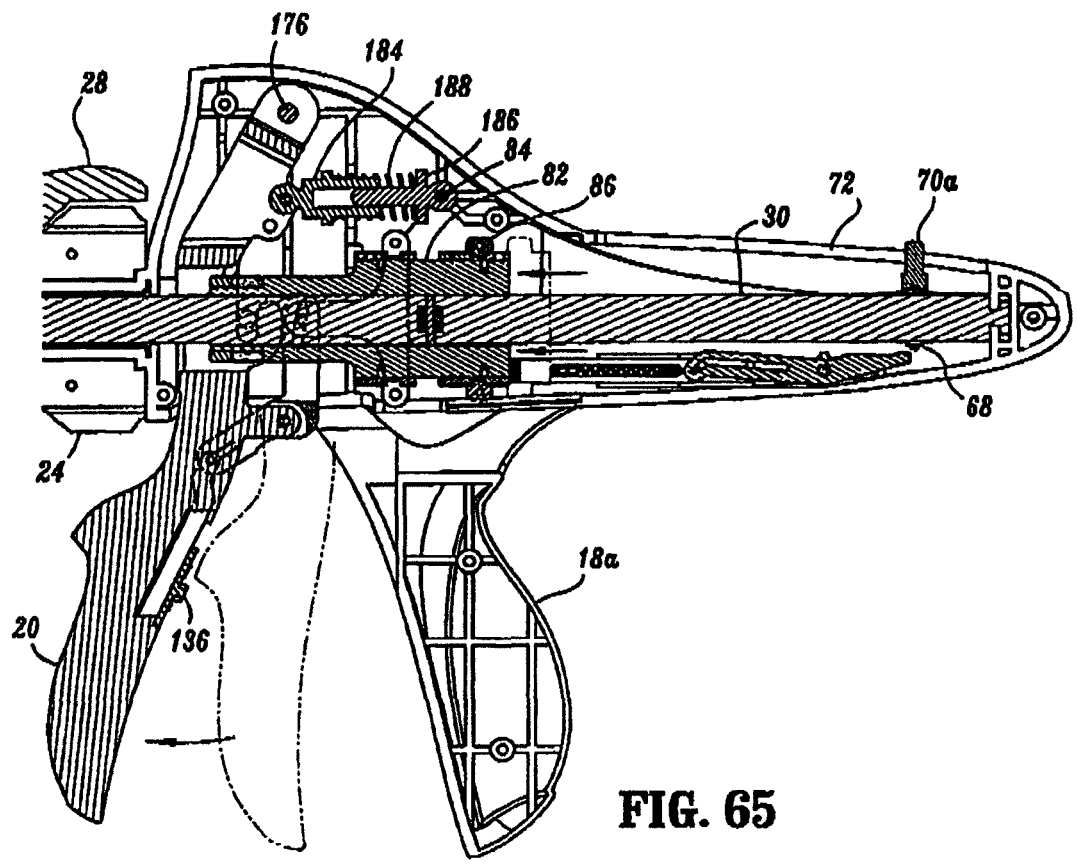
FIG. 65 is a side cross-sectional view of the handle assembly of the surgical stapling device shown in FIG. 1 with the first shift ring assembly in the advanced position, and the firing trigger moved through one actuation stroke returned to the non-compressed position.
Figure 66:
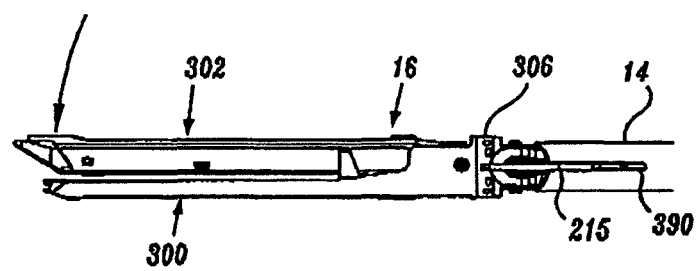
FIG. 66 is a side view of the tool assembly shown in FIG. 52 moved to the closed position.
Figure 67:
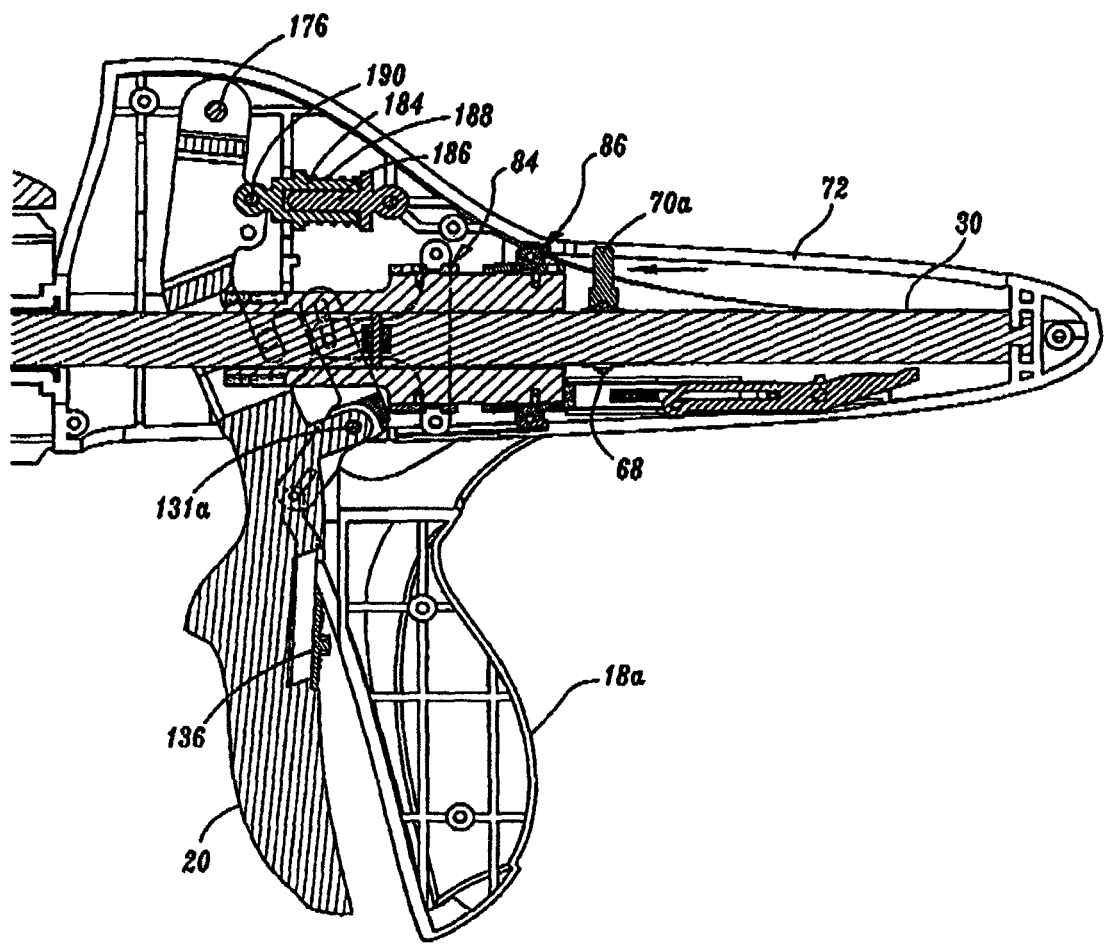
FIG. 67 is a side cross-sectional view of the handle assembly shown in FIG. 65 after the device has been fired with the indicator member in the fully advanced position.
Figure 68:
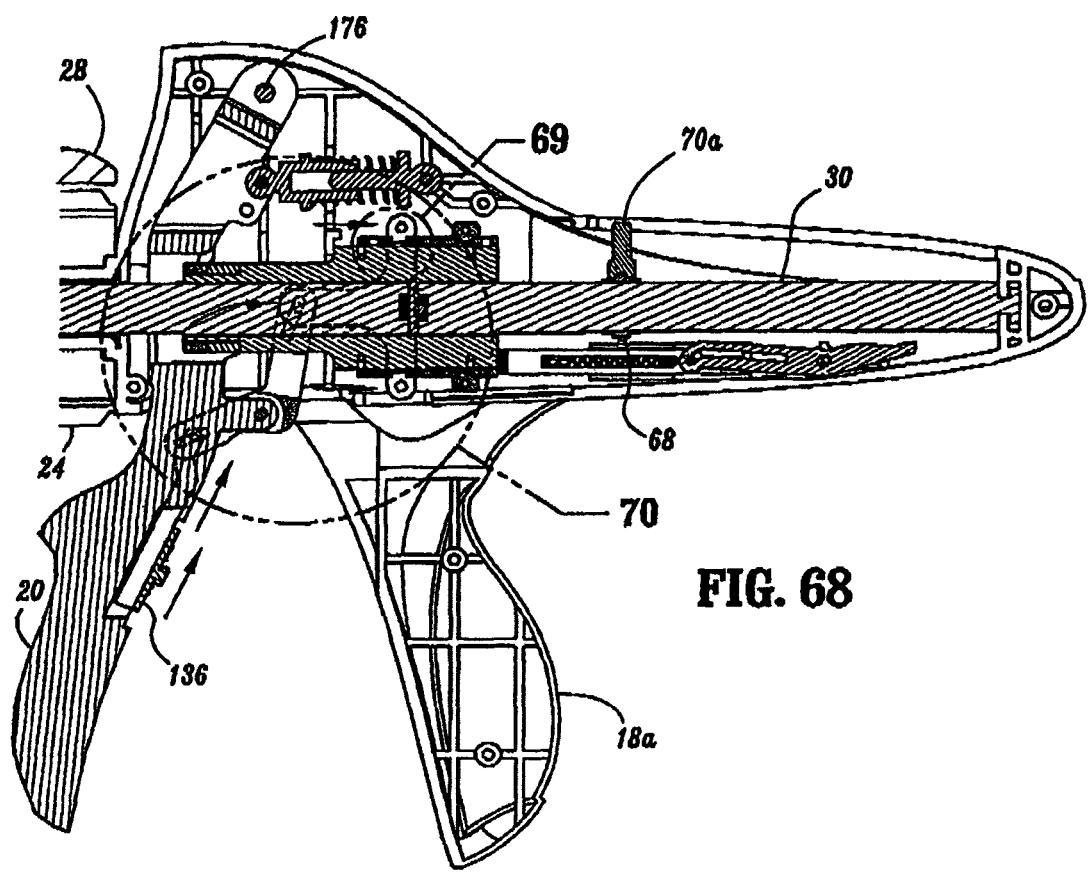
FIG. 68 is a side cross-sectional view of the handle assembly shown in FIG. 67 with the selector switch moved to move the first shift ring assembly to its retracted position.

Referring to FIG. 64, when firing trigger 20 is released after each actuation stroke, because of the angle of teeth 56b of firing pawl 56, firing pawl 56 will ratchet over firing rack 48 as spring 188 (FIG. 65) returns firing trigger 20 and barrel assembly 80 to the unactuated position.

Figure 70:
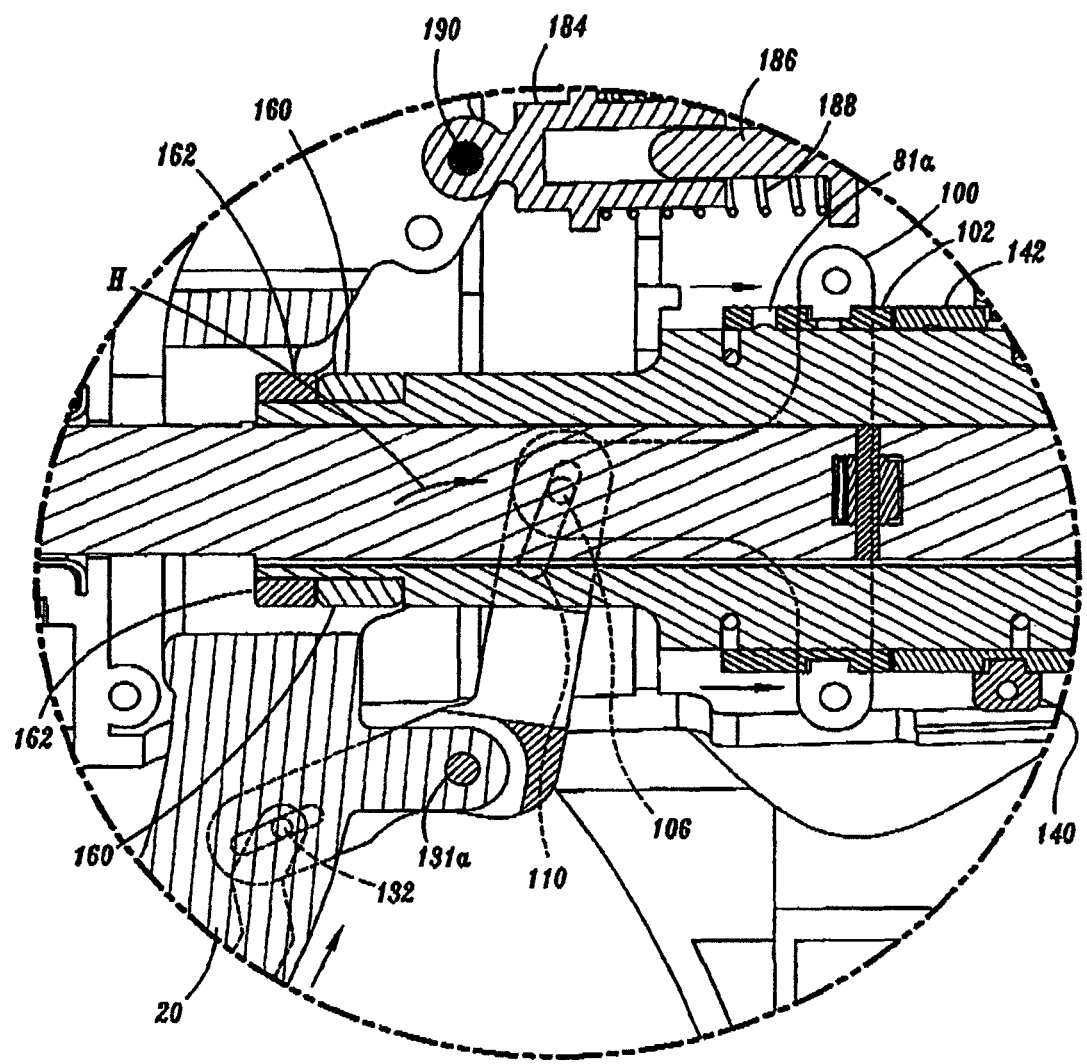
FIG. 70 is an enlarged view of the indicated area of detail shown in FIG. 68.
Figure 71:
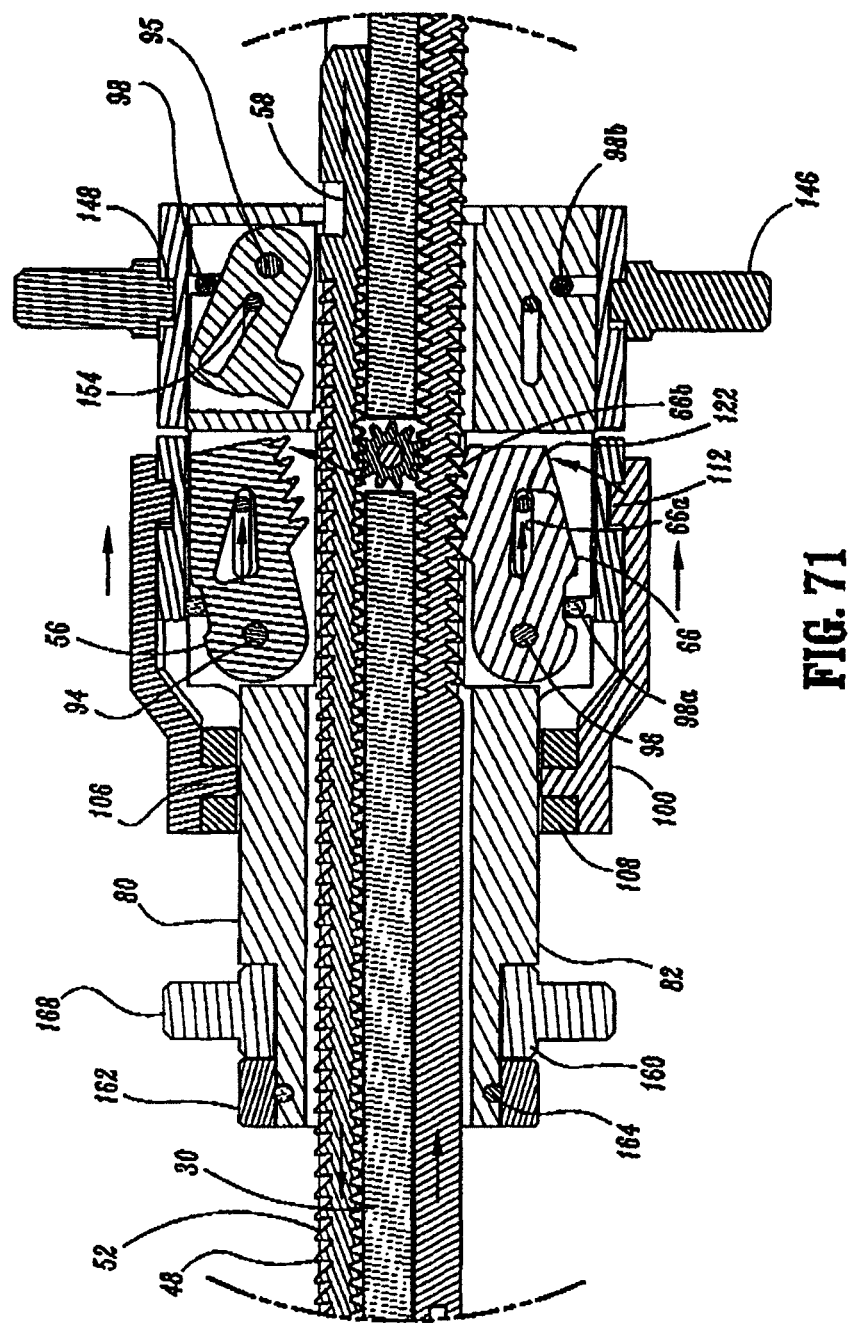
FIG. 71 is an enlarged side cross-sectional view of the spindle and barrel assembly shown in FIG. 68 with the retraction pawl engaged in the retraction rack.

Referring to FIGS. 68-71, in order to retract dynamic clamping member 309 to be able to move the anvil and cartridge assemblies to their spaced position, shift lever 136 is pushed upwardly on firing trigger 20 to pivot lever 108 about pivot member 131a in the direction indicated by arrow "H" in FIG. 70. This will move the first shift ring assembly including inner ring 102 to the retracted position. As discussed above, when inner ring 102 is in the retracted position, cam member 120 urges firing pawl 56 to a position disengaged from firing rack 48 and cam 122 is moved to a position within cam slot 66a of retraction pawl 66 to allow O-ring 98a to urge retraction pawl teeth 66b into engagement with retraction rack 50.

When firing trigger 20 is compressed or moved through an actuation stroke, barrel assembly 80 is moved proximally about spindle 30. Since retraction pawl 66 is engaged with retraction rack 50, retraction rack 50 is moved proximally along guide track 34. Movement of retraction rack 50 proximally rotates pinion 42 to drive firing rack 48 distally along guide track 32. As discussed above, when firing trigger 20 is released, spring 188 urges firing trigger 20 back to its non-compressed position to move barrel assembly 80 to its original non-fired position. Retraction pawl 66 ratchets over gear teeth when barrel assembly 80 moves to its original position. Firing trigger 20 may have to be moved through multiple actuation strokes to fully retract dynamic clamping member 309 and move anvil and cartridge assemblies 300 and 302 to their open position. As retraction rack 50 is moved proximally, retraction cable 412 is pulled proximally to pull dynamic clamping member 309 proximally in relation to anvil and cartridge assemblies 300 and 302 to move the anvil and cartridge assemblies to their open position.

It will be understood that various modifications may be made to the embodiments disclosed herein. For example, although the handle assembly is disclosed to include a double ratchet assembly to both advance and retract the clamping member, other handle assemblies may also be used, e.g., handle assemblies which include manual pull return mechanisms may be employed such as disclosed in U.S. Pat. No. 6,241,139, which is incorporated herein in its entirety by reference. Therefore, the above description should not be construed as limiting, but merely as exemplifications of preferred embodiments. Those skilled in the art will envision other modifications within the scope and spirit of the claims appended hereto.

What is claimed is:

1. A surgical device comprising:
a handle assembly;
an elongate body portion extending distally from the handle assembly and defining a first longitudinal axis, the body portion being rotatable in relation to the handle assembly about the first longitudinal axis;
a tool assembly defining a second longitudinal axis and being rotatably and pivotally supported on a distal end of the body portion, the tool assembly being pivotal about a pivot axis substantially transverse to the first longitudinal axis of the body portion and rotatable about the second longitudinal axis;
an actuation member associated with the tool assembly, the actuation member being operatively connected to the handle assembly and movable to actuate the tool assembly;
an outer tube having an opening; and
a control mechanism configured to effect independent rotation of the tool assembly, the control mechanism including a hollow tube positioned within the body portion, the hollow tube including a distal end connected to the tool assembly, and a rotation knob configured to activate the control mechanism, the control mechanism having an outer ring gear, a first internal pinion gear, and a second internal pinion gear, the first internal pinion gear meshing with the outer ring gear, the first internal pinion gear being disposed in the opening of the outer tube, and the second internal pinion gear meshing with the first internal pinion gear, the second internal pinion gear being connected to the hollow tube.

2. A surgical device according to claim 1, wherein the hollow tube includes a proximal end operably connected to the rotation knob.

3. A surgical device according to claim 1, wherein the tool assembly includes a cartridge assembly having a plurality of staples supported therein and an anvil assembly, the anvil assembly being movable in relation to the cartridge assembly between spaced and approximated positions.

4. A surgical device according to claim 3, wherein the staples of the cartridge assembly are arranged in a plurality of linear rows.

5. A surgical device according to claim 4, further including a drive sled positioned adjacent to the actuation member, and a knife blade supported by the actuation member.

6. A surgical device according to claim 1, wherein the handle assembly includes an operating trigger operably connected to the actuation member.

7. A surgical device according to claim 6, wherein the operating trigger is connected to the actuation member by a flexible firing cable.

8. A surgical device according to claim 7, wherein the flexible firing cable extends through the hollow tube of the control mechanism.

9. A surgical device according to claim 8, further comprising a torque-transmitting flexible member connected to the hollow tube and the tool assembly.

10. A surgical device according to claim 9, wherein the flexible firing cable extends through the torque-transmitting flexible member.

11. A surgical device according to claim 1, further comprising a flexible retraction cable, the flexible retraction cable being operable in tension to move the actuation member.

12. A surgical device comprising:
a handle assembly;
an elongate body portion extending distally from the handle assembly and defining a first longitudinal axis, the body portion being rotatable in relation to the handle assembly about the first longitudinal axis;
a tool assembly defining a second longitudinal axis and being rotatably and pivotally supported on a distal end of the body portion, the tool assembly being pivotal about a pivot axis substantially transverse to the first longitudinal axis of the body portion and rotatable about the second longitudinal axis, the tool assembly including a drive member which drives a rotational movement of the tool assembly about the second longitudinal axis;
an actuation member associated with the tool assembly, the actuation member being operatively connected to the handle assembly and movable to actuate the tool assembly;
an outer tube having an opening; and
a control mechanism configured to effect independent rotation of the tool assembly, the control mechanism including:
a hollow tube positioned within the body portion, the hollow tube including a distal end operatively connected to the tool assembly;
a wheel defining a ring gear configured to activate the control mechanism;
a first internal pinion gear configured to mesh with the ring gear and being disposed in the opening of the outer tube; and a second internal pinion gear configured to mesh with the first internal pinion gear, the second internal pinion gear being connected to the hollow tube; and a torque-transmitting flexible member connected to the hollow tube and the tool assembly, wherein the proximal end of the torque-transmitting flexible member is fixedly secured to the distal end of the hollow tube and the distal end of the torque-transmitting flexible member is fixedly secured to the tool assembly.

13. A surgical device according to claim 12, wherein the tool assembly includes a cartridge assembly having a plurality of staples supported therein and an anvil assembly, the anvil assembly being movable in relation to the cartridge assembly between spaced and approximated positions.

14. A surgical device according to claim 13, wherein the staples of the cartridge assembly are arranged in a plurality of linear rows.

15. A surgical device according to claim 14, further including a drive sled positioned adjacent to the actuation member, and a knife blade supported by the actuation member.

16. A surgical device according to claim 12, wherein the handle assembly includes an operating trigger operably connected to the actuation member.

17. A surgical device according to claim 16, wherein the operating trigger is connected to the actuation member by a flexible firing cable.

18. A surgical device according to claim 17, wherein the flexible firing cable extends through the hollow tube of the tool assembly rotation mechanism.

19. A surgical device according to claim 12, further comprising a flexible retraction cable, the flexible firing cable being operable in tension to move the actuation member.

\* \* \* \* \*